US005160737A

United States Patent [19]
Friedman et al.

[11] Patent Number: 5,160,737
[45] Date of Patent: Nov. 3, 1992

[54] LIQUID POLYMER COMPOSITION, AND METHOD OF USE

[75] Inventors: Michael Friedman; Amnon Sintov, both of Jerusalem, Israel

[73] Assignees: Perio Products Ltd.; Yissum Research Development Company, Israel

[21] Appl. No.: 522,117

[22] Filed: Mar. 28, 1990

Related U.S. Application Data

[63] Continuation-in-part of Ser. No. 432,667, Nov. 7, 1989, abandoned, which is a continuation-in-part of Ser. No. 189,918, May 3, 1988, abandoned, Ser. No. 304,091, Jan. 31, 1989, abandoned, Ser. No. 304,092, Jan. 31, 1989, abandoned, and Ser. No. 369,223, Jun. 21, 1989, abandoned.

[51] Int. Cl.$^5$ ............................................. A61K 9/08
[52] U.S. Cl. .................................. 424/401; 424/49; 424/52; 424/54; 514/900; 514/901; 514/902
[58] Field of Search ............... 424/49, 54, 52, 401; 514/900, 901, 902

[56] References Cited

U.S. PATENT DOCUMENTS

| | | | |
|---|---|---|---|
| 2,984,639 | 5/1961 | Stamberger et al. | 525/329.6 |
| 3,846,542 | 11/1974 | Gross | 424/81 |
| 3,925,895 | 12/1975 | Kliment et al. | 433/224 |
| 3,956,480 | 5/1976 | Dichter et al. | 424/54 |
| 4,011,309 | 3/1977 | Lutz | 424/49 |
| 4,539,199 | 9/1985 | Orbán et al. | 424/456 |
| 4,554,156 | 11/1985 | Fischer et al. | 424/81 |
| 4,645,662 | 2/1987 | Nakashima et al. | 424/52 |
| 4,683,134 | 7/1987 | Palinczar | 424/59 |
| 4,701,320 | 10/1987 | Hasegawa et al. | 424/54 |
| 4,751,072 | 6/1988 | Kim | 424/49 |
| 4,775,525 | 10/1988 | Peria | 424/58 |
| 4,876,092 | 10/1989 | Mizobuchi et al. | 424/435 |
| 4,911,922 | 3/1990 | Matsuhara et al. | 424/81 |
| 4,963,347 | 10/1990 | Humphries et al. | 424/49 |

FOREIGN PATENT DOCUMENTS

| | | |
|---|---|---|
| 66707/86 | 12/1986 | Australia. |
| 79557/87 | 10/1987 | Australia. |
| 0140766-A2 | 5/1985 | European Pat. Off.. |
| 140766 | 5/1985 | European Pat. Off.. |
| 0184389 | 6/1986 | European Pat. Off.. |
| 0265228 | 4/1988 | European Pat. Off.. |
| 63-60924 | 3/1988 | Japan. |
| 1294173 | 10/1972 | United Kingdom. |
| 1324798 | 7/1973 | United Kingdom. |
| 1431211 | 4/1976 | United Kingdom. |
| 2128087A | 4/1984 | United Kingdom. |

OTHER PUBLICATIONS

Standards Sheet (Info L/S-7a/e) Eudragit TM L/S.
Technical Application Pamphlet (Info L/S-13/e) Eudragit TM L/S.
Eudragit TM RL and RS: Application in the Production of Pharmaceutical Preparations.
Manufacturer's Listing of the Different Types of Eudragit TM, Manuf. Röhm Pharma GmbH Weiterstad.
European Search Report for Application No. 90306775.9.
Chafi et al., *Drug Dev. Indus. Pharm.* 15(4):629–648 (1989).
Chang et al., *Drug Dev. Indus. Pharm.* 15(3):361–372 (1989).
Thoennes et al., *Drug Dev. Indus. Pharm.* 15(2):165-185 (1989).
Goto et al., *J. Microencapsulation* 5(4):343-360 (1988).

*Primary Examiner*—Thurman K. Page
*Assistant Examiner*—Robert H. Harrison
*Attorney, Agent, or Firm*—Sterne, Kessler, Goldstein & Fox

[57] ABSTRACT

The invention relates to a liquid methacrylic acid copolymer composition that contains a release adjusting agent and a pharmacological agent. The composition forms a solid film upon drying, and is capable of accomplishing the sustained release of the pharmacological agent such as to permit its use in the treatment or prevention of dental or dermatological conditions.

18 Claims, 30 Drawing Sheets

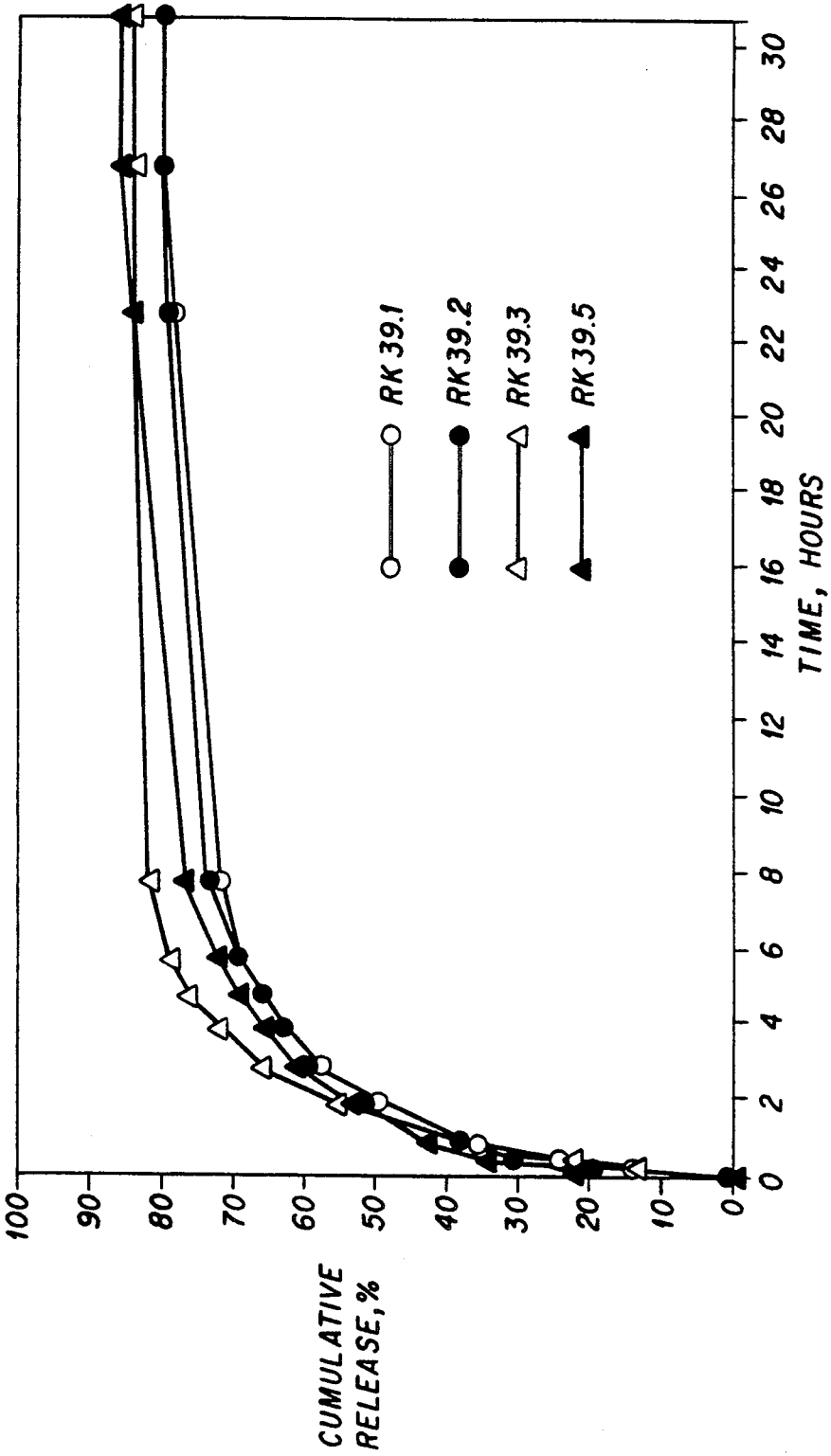

LIQUID POLYMER COMPOSITION, AND METHOD OF USE

CROSS REFERENCE TO RELATED APPLICATIONS

This application is a continuation-in-part of U.S. application Ser. No. 07/432,667, abandoned filed Nov. 7, 1989, which is a continuation-in-part of U.S. patent application Ser. Nos. 07/189,918 (filed May, 3, 1988), abandoned, 07/304,091 (filed Jan. 31, 1989), 07/304,092 (filed Jan. 31, 1989), abandoned, and 07/369,223 (filed Jun. 21, 1989) abandoned, which applications are all incorporated herein by reference.

FIELD OF THE INVENTION

The invention is directed to a liquid polymer composition which may be used in the treatment or prevention of dental or dermatological conditions such as fungal, bacterial, or viral infection, tooth hypersensitivity etc. The composition provides a sustained release of an active agent which may be an antiseptic, an antibiotic, a viricidal agent, or any other pharmacological agent.

BACKGROUND OF THE INVENTION

I. Dental Conditions

A. Prevention of Plaque Formation, Caries, and Periodontal Disease

The relationship between bacterial plaque and the development of periodontal disease and caries has been thoroughly established (Axelsson, P., et al., *J.Clin. Perio.* 5:133-151 (1978)). Periodontal disease is a major problem in humans, especially in adults 40 years of age or older, in the mentally retarded, and in the handicapped. For the latter two groups in particular this is due to an inability to properly care for the teeth. Periodontal disease is also widespread among animals, especially housepets. It has also been clearly shown that the bacterial flora of the gingival crevice is important in the etiology of periodontal disease (Slots, J., *J. Clin. Perio.* 6:351-382 (1979)). Therefore, treatment of periodontal and caries diseases is directed to controlling this flora.

The most widely used approach to data has been mechanical cleaning methods such as tooth brushing. Although this method has proved to be fairly successful in treating individuals, there is still a high recurrence rate. There is also the problem of motivating people to good oral hygiene habits that they will maintain throughout their lives.

Although systemic administration of antibiotics has been shown to be a useful method of controlling the subgingival flora, discontinuation of therapy will result in the return of the potential pathogens to the pockets (Genco, R.J., *J. Perio.* 52:545-558 (1981)). Long-term antibiotic therapy has been used, but the potential dangers associated with this form of treatment, which include the development of resistant strains and superimposed infections, do not warrant its serious consideration.

Antibacterial agents such as chlorhexidine and quaternary ammonium salts in the form of mouth rinses, dentifrices, solutions and gels have not proven to be successful in preventing periodontal disease (see, for example, Ciancio, S.G., et al., *Pharm. Therap. Dent.* 3:1-6 (1978)), as these agents are unable to affect the subgingival flora when administered in these forms (Goodson, J.M., et al., *J. Clin. Perio.* 6:83-92 (1979)). In addition, reported side effects of chlorhexidine, including staining and altered taste sensation, have resulted in limited usage. Attempts to reduce the staining and bitter taste by using dilute solutions and flavoring agents, respectively, have been only partially successful.

Sustained release has been reported to be achieved by embedding chlorhexidine in an ethyl cellulose polymer to form a film (Friedman, M., et al., *J. Perio. Res.* 17:323-328 (1982); Friedman, M., et al., *IADR Prog. and Abstr.* 59:No. 905 (1980)). This dosage form was used in the local treatment of periodontal disease (Soskolne, W.A., et al., *J. Perio. Res.* 18:330-336 (1983)) and in the treatment of plaque prevention in patients wearing orthodontic appliances (Friedman, M., et al., *J. Dent. Res.* 64:1319-1321 (1985)). A drawback to this plaque preventative system was that although plaque accumulation was decreased by the application of a film composed of chlorhexidine embedded in an ethyl cellulose polymer, the effectiveness of the system in decreasing plaque accumulation was present only for a period of four days subsequent to administration of the film. Friedman, M., et al., (*J. Dent. Res.* 64:1319-1321 (1985)), concluded that "clearly the conditions in the oral cavity and the formulation used do not, at present, facilitate such prolonged prevention of plaque accumulation." These authors also suggested that by altering the film components and method of preparation it might be possible in clinical use to sustain the necessary level of antibacterial agent release for longer periods. No suggestion was made in this publication as to how this could be accomplished.

Other antibacterial preparations for plaque prevention have been disclosed. Gaffar (U.S. Pat. No. 4,339,430) discloses an antibacterial oral composition containing an agent such as bisbiguanidohexanes or quaternary ammonium salts, and an additive which reduces staining of dental surfaces such as copolymers of glutamic acid, tyrosine, and alanine. This preparation was reported to be applied as a mouthwash or as a toothpaste.

Wahmi (U.S. Pat. No. 4,374,824) disclosed dentifrices for cleaning and preserving teeth. Disclosed were compositions comprising ginger, magnesium silicate, sodium chloride, catechu, alum, seed and shell of sweet almond, pyrethrum, gum mastic, and tobacco. It was reported that gum mastic was added to the composition to assist in the prevention of tooth decay. The disclosed compositions were intended to be in the form of toothpaste or tooth powders. This patent does not disclose the possible long-term anti-plaque effect of the compositions; further, application of the disclosed compositions two to three times per day is required for anti-plaque activity.

Mastic has been used previously for other dental purposes. U.S. Pat. No. 4,668,188 (Wolfenson, G.B.) discloses the use of a curable mastic in the production of an oral impression tray for making impressions of teeth and jaw structures. Mastics have been used in the production of dental molds (U.S. Pat. No. 4,500,288, Von Weissenfluh, H.) and as an adhesive to secure dental articulators (U.S. Pat. Nos. 4,548,581 and 4,382,787, Hoffman, R.E.). U.S. Pat. Nos. 4,532,126 and 4,428,927 (Ebert, W.R., et al.) disclose chewable, filled, one-piece soft elastic gelatin capsules, made chewable by a masticatory substance, such as a synthetic mastic.

U.S. Pat. No. 4,459,277 (Kosti, C.M.) relates to novel anti-plaque compositions for use in evaluating oral hygiene practices. In brief, the patent discloses a water-insoluble, water-immiscible dye emulsified in fine droplets or rupturable capsules. The patent discloses the use of mastic resin as well as alginates, and other gums as an insoluble media for dye dispersion. In particular, sodium carboxymethylcellulose is disclosed. Also disclosed is the possibility of incorporating antibacterial agents such as stannous fluoride into the compositions. Significantly, the Kosti patent is concerned with diagnostic rather than therapeutic applications. The patent fails to suggest compositions exhibiting long-term plaque preventive activity.

U.S. Pat. No. 3,956,480 (Dichter et al.) discloses the use of an anionic polymer to sorb a cationic germicidal polymer to a tooth surface.

A topical, sustained-release form of an antibacterial agent could help prevent the above-discussed side effects. Such a dosage form would be able to release the drug at a lower therapeutic level over a long period of time and thus might prevent the bitter taste and tooth staining.

B. Treatment of Tooth Hypersensitivity

Dental hypersensitivity, especially that arising from dentin and cementum hypersensitivity, is a frequently encountered problem in dentistry and a very troublesome clinical complaint. Hypersensitivity may occur wherever the dentin or cementum of a tooth is exposed by attrition or abrasion, or when the tooth's fine root surface is exposed by periodontal disease. In about 12% of erupted teeth, there is a developmental lack of protective covering of cementum at the cementoenamel junction. As a result, when the exposed dentin is subjected to mechanical, thermal, chemical or osmotic stimuli, the sensory nerves of the teeth become excited and a very painful response results. For example, people with hypersensitive teeth find it very painful to orally ingest certain forms of nourishment, such as liquids or foods that are hot or cold, sweet, hypertonic or contain citric acid. Everyday stimuli such as brushing the teeth may also be painful.

Many attempts have been made to control hypersensitivity of the teeth. For example, U.S. Pat. No. 3,863,006 (Hodosh, M.) describes the use of potassium, lithium or sodium nitrate; U.S. Pat. No. 4,751,072 and U.S. Pat. No. 4,631,185 (both to Kim, S.) describe the use of potassium bicarbonate and potassium chloride; U.S. Pat. No. 4,710,372 and U.S. Pat. No. 4,634,589 (both to Scheller, H.U.) describe the use of hydroxyapatite or fluorapatite; U.S. Pat. No. 4,057,621 Pashley, D.H., et al.) describes the use of an alkali metal or ammonium oxalate; U.S. Pat. No. 4,415,549 (Shah, N.B.) describes the use of strontium EDTA, fluoride and ammonium glycyrrhizzinate; and, GB patent No. 990957 (Rosenthal, M.W.) describes the use of strontium for the control of hypersensitivity. The use of strontium ions to treat hypersensitivity was also disclosed in U.S. Pat. Nos. 3,122,483, 3,988,434 and 4,224,310.

However, although clinically the most effective for reducing tooth hypersensitivity, the use of strontium salts for the treatment of hypersensitivity is disliked by patients due to the tendency of strontium salts to leave an unacceptably salty taste or metallic taste in the mouth, even when used in a toothpaste form. Another major disadvantage of strontium dentifrice is the long period of time of application which is required to achieve the clinical effect.

A topical, sustained-release form of an agent capable of controlling dental hypersensitivity could help prevent undesirable taste side effects and still treat the hypersensitive condition. Such a dosage form would be able to release the agent controlling the hypersensitivity at a lower therapeutic level over a long period of time, for example, for weeks. Sustained localized release of the hypersensitivity agent, targeted directly to the hypersensitive site, would also solve the problem of the prolonged time and application currently required to obtain clinical effectiveness with strontium.

C. Root Canal Sterilization

A major concern in root canal dental procedures is the possibility of infection due to the introduction or cross-infection of bacteria, etc. into the affected region. Various surgical and endodontic methods have been developed in order to minimize the risk of infection (Miserendino, L.J., *Oral Surg. Oral Med. Oral Pathol.* 66:615–619 (1988); Mondragon, E.J., *Pract. Odontol.* 8:16–22 (1987); Hermsen, K.P. et al., *Gen. Dent.* 35:355–356 (1987); Levy, G. et al., *Zahnarzt* 30:441–442, 447–450 (1986); Chivian, N., *Dent. Clin. North Amer.* 28:637–649 (1984); Linke, H.A. et al., *Oral Surg. Oral Med. Oral Pathol.* 55:73–77 (1983); Agarwal, S.K. et al., *J. Indian Dent. Assoc.* 54:323–326 (1982), which references are incorporated herein by reference). Camphorated parachlorophenol (CPK) is an antibacterial agent used to treat bacterial contamination in the root canal. The usual treatment involves dipping an absorbent point or gauze into a CPK solution and placing it in the root canal. The absorbent point remains in the root canal until the next visit to the dentist. The primary disadvantage of the current treatment is the limited exposure time of the active material which may lead to re-infection of the root canal.

II. Fungal Infections

Microfungi can be classified as yeasts and filamentous fungi. Microfungi are capable of causing a variety of diseases in the oral cavity and the surrounding area. Mycotic diseases may arise as part of a systemic microfungal infection or may be derived from an independent infection which establishes in the oral cavity. Oral mycoses and their treatment are an important problem in oral medicine and have been reviewed in Kostiala, I. et al., *Acta Odontol. Scand.* 37:87–101 (1987), incorporated herein by reference.

Many factors can predispose a patient to an opportunistic microfungal infection in the oral cavity. For example, general debilitation or poor oral hygiene are predisposing factors. Patients who are being treated with antibiotics, steroids, or cytostatic therapy, patients with AIDS, diabetes mellitus or other immunodeficiency or hormonal diseases, patients with malignant tumors or a hematogenous disorder are a high risk for opportunistic fungal infections. In addition, certain age groups such as infants, the elderly, and pregnant women are at a higher risk of oral fungal infections.

Mechanical trauma from an ill-fitted prosthesis is also a major cause of oral microfungal infections. One report estimated that Candida was involved in 60% of the cases of "denture sore mouth" (denture stomatitis) in the elderly (Budtz-Jörgensen, E. et al., *Community Dent. Oral Epidemiol.* 3:115 (1975)). Denture stomatitis appears to be a manifestation of a cell-mediated hypersensitivity reaction to the microfungal infection.

It is important to treat oral mycotic infections as soon as possible. Untreated infections may become the foci for systemic dissemination of the yeast or fungus, with potentially fatal result in severely compromised patients. For example, disseminated candidiasis is the second most common opportunistic infection in patients with AIDS (Odds, F.C., *CRC Crit. Rev. Microbiol.* 15:1-5 (1987)).

The most important species of microfungi which have been implicated as being involved in superficial or deep mycotic infections in the oral cavity include *Candida albicans, C. tropicalis, C. stellatoidea, C. pseudotropicalis, C. parapsilosis, C. guilliermondii, C. krusei*, and *C. vixwanathii*, all of which have been implicated in candidiasis; *Torulopsis glabrata* which is the cause of torulpsidosis; *Geotrichum candidum*, which is the cause of geotrichosis; *Rhizopus, Mucor, Absidia*, and *Basidiobolus* which are the cause of aspergillosis, *Cryptococcus neoformans*, the cause of cryptococcosis; *Blastomyces dermatitidis*, the cause of blastomycosis; *Paracoccidioides brasiliensis*, the cause of paracoccidioidoymcosis; *Sporothrix schenkii*, the cause of sporotrichosis; *Rhinosporidium seeberi*, the cause of rhinosporidoisis; *Histoplasma capsulatum*, the cause of histoplasmosis; *Histoplasma duboisii*, the cause of African histoplasmosis, *Coccidiodes immities*, the cause of coccidioidoymcosis, *Trichophyton mentagrophytes, T. rubrum, T. tonsurans*, and *T. violaceum*, the causes of dermatophytosis; and, *Rhinocladiella* or *Phialophora*, and *Cladosporium*, the causes of chromomycosis.

The Candida species is the most virulent of the fungi which infect the oral mucosa. Pathogenic Candida species are aerobic yeasts that can also grow anaerobically. *C. albicans*, the Candida species most often responsible for infections of the oral cavity, grows in two morphological forms: either as a budding yeast, or as a continuously extending hyphae which extends into tissue. In the oral cavity, Candida may cause a variety of disorders based on localization of the infection such as pulpitis, gingivitis, tonsillitis, cheilitis, glossitis, stommatitis, pharyngitis, laryngitis and sinusitis.

Oral candidiasis has been classified into different categories based on the clinical and histopathological manifestations of the infection (Lehner, T., in *Clinical Aspects of immunology*, P.G.H. Gell, et al., eds., 3rd edition, Blackwell Scientific Publications, Oxford, 1975, pp. 1387-1427).

Acute pseudomembranous candidiasis, or thrush, primarily affects children or patients with debilitating diseases (Crawson, R.A., *Dent. Res.* 15:361-364 (1965). *C. albicans* is a major causative agent of thrush in the newborn.

The clinical signs which usually appear first are creamy-white, soft, nonkeratotic plaques which appear on the mucosa of the tongue, cheeks, gum and pharynx. The plaque is easily rubbed off, leaving an inflamed mucosa underneath. There may be no subjective symptoms until the plaque spreads to the pharynx, larynx or esophagus, where it may cause dysphaghia, soreness and dryness of the tongue, a sore throat or symptoms of cheilitis.

Acute atrophic candidiasis is a form of thrush which is consistently painful, and which is through to arise as a consequence of the shedding of the fungal plaque from its site of attachment to the tissue. It can be found on the dorsum linguae, or associated with angular cheilitis and inflammation of cheeks and lips.

Chronic atrophic candidiasis, or denture stomatitis is the term given to Candida-based infections of the denture-bearing tissues. *Torulopsis glabrata* is also associated with some forms of denture stomatitis.

Chronic mucocutaneous candidiasis refers to four different types of candidiasis which are resistant to treatment and which are associated with patients with a herterogeneous pattern of immunodeficiencies. These types of candidiasis include chronic oral hyperplastic candidiasis, which predominately affects adult males between the ages of 30 and 70; chronic localized mucocutaneous candidiasis, which starts in childhood as an intractable oral Candida infection and later manifests itself as lesions in the nails, and skin of the fingers and toes; chronic localized mucocutaneous candidiasis with granuloma which primarily affects young girls, starting in the mouth but later manifesting itself as horny masses of the face, scalp and upper respiratory tract; and, chronic localized mucocutaneous chadidosis with endocrine disorder, also found most frequently in young girls, and associated with lesions of the tongue, cheek, oral commissures and nails.

The establishment of a mycotic infection in the oral cavity presents a serious health problem to the host which must be treated and contained. Treatment of mycotic diseases is directed to controlling this flora.

The most widely used approach to data to control microfungi in the oral cavity has been mechanical cleaning methods such as brushing the teeth. Although this method has proved to be fairly successful in treating individuals, there is still a high recurrence rate. There is also the problem of motivating people to good oral hygiene habits that they will maintain throughout their lives.

Systemic administration of antimycotics per os or intravenously has been used to control mycotic infections, however, discontinuation of therapy often results in the return of the pathogens to the oral cavity. Long-term systemic antimycotic therapy in doses high enough to control oral infections are undesirable for treatment of oral infections because the potential dangers and side-effects associated with this form of treatment include the development of resistant strains and superimposed infections, gastrointestinal irritation, liver damage and neurological symptoms, among others.

Ridgway, F. et al., U.S. Pat. No. 4,725,440, describes a soft, anti-fungal drug-containing pastille or troche which is free of rough edges and will not adhere to oral mucosa, but which only releases anti-fungal medications within the 15-90 minutes while it dissolves in the mouth.

Cyr et al., U.S. Pat. No. 3,312,594 describes long lasting troches or pastilles for the treatment of oral lesions which include an anhydrous adhesive based on pectin, gelatin and carboxymethylcellulose and which, when wetted, adhere to the oral mucous membranes. However, the Cyr formulation was not well-tolerated by patients (Ridgway, F. et al., U.S. Pat. No. 4,725,440).

Antifungal agents have also been used in the form of mouth rinses, dentifrices, solutions and gels but have not proven to be completely successful in preventing fungal infections. A main problem with these techniques is that the antifungal drug does not remain in the oral cavity long enough at efficacious levels.

Another serious problem with antifungal drugs is that they are by necessity directed towards controlling an infection by a eukaryotic fungal cell in a eukaryotic host. As a result, drugs effective against the fungus also tend to be toxic to the host. Thus is it important to develop methods which permit the localized, sustained application of the toxic drug in a manner and dosage which is efficacious but which minimizes toxicity the host. Especially, it is important to develop methods which use low doses of the drug.

III. Dermatological Conditions

A dermatological disease or condition is one which affects the skin. Such conditions may reflect either the reaction of the immune system to a particular antigen or allergen, as is the case in rashes associated with allergic contact dermatitis (such as a reaction to poison ivy, poison oak, bee venom, etc.). Other dermatological conditions are caused by a variety of inflammatory causes (such as exfoliative dermatitis, eczematous dermatitis, pustules, psoriasis, urticaria, erythema multiforme syndrome, purpura, etc.). Yet other dermatological conditions may reflect bacterial infection (such as insect bites, impetigo, acne vulgaris, Lyme disease lesions, etc), fungal infection (such as ringworm, tinea versicolor, cutaneous candidiasis, molluscum contagiosum, etc.) or viral infection (such as warts, herpes simplex or zoster lesions, chicken pox lesions, rubella macules or papules, etc.).

Yet another type of dermatological condition of concern to the present invention are burns, and especially sunburn.

IV. Summary

The background art thus fails to identify any compositions of matter comprising a sustained-release carrier which can be used in conjunction with a bacteriocidal agent, for use as a sustained plaque preventative by humans and other animals, under conditions in which the agents have no deleterious medical side effects, and do not cause staining of the teeth.

The background art also fails to identify any compositions of matter comprising an effective anti-hypersensitivity agent together with a long term sustained release carrier capable of providing efficacious levels of the anti-hypersensitivity agent, for use as a hypersensitivity preventative by humans and other animals, under conditions in which the anti-hypersensitivity agents have no undesirable side effects such as changes in taste sensations.

A topical, sustained-release form of an antifungal agent, could help maintain a locally efficacious level of the antifungal drug in the oral cavity and prevent these side effects. Such a dosage form might also prevent undesirable systemic side effects by releasing the drug at a lower therapeutic level over a long period of time in a localized manner.

A need therefore exists for a composition comprising a sustained release carrier which could be used in conjunction with an antifungal, antibiotic, antiseptic, antiviral or other pharmacological agent, for use in the sustained release of such agent(s) in the prevention or therapy of dental, dermatological (and other) conditions of humans and other animals. It is particularly desirable that the antibacterial agent should be released from the composition, not only in a sustained fashion, but over a sufficiently long period of time so as not to require excessive application of the composition.

SUMMARY OF THE INVENTION

With the above-described needs in mind, the present inventors set out to find a composition which could be adapted to accomplish the sustained release of a pharmacological agent such as to permit its use in the treatment or prevention of dental or dermatological conditions.

When attempting to use dental or dermatological agents in a liquid polymer composition consisting of methacrylic acid copolymer, two principal problems are encountered: (1) the hydrophilic nature of the copolymer causes rapid disintegration of the film, and in parallel, causes rapid release of the active agent; and (2) some agents may interact with the copolymer making it hydrophobic in nature, thus almost totally preventing release of the active agent from the film and slowing the disintegration process (i.e., nondegradable film).

These problems have prevented the use of such a polymer as a matrix for the controlled release of drugs to treat dental or dermatological conditions.

The invention has, for the first time, solved these problems and, for the first time, allowed dental and dermatological agents to be provided to a subject in a controlled or sustained release manner in conjunction with acrylic polymers.

Of particular concern to the present invention are oral conditions, including both conditions that are directly related to dental and periodontal disease (such as plaque, dental caries, periodontal disease, root canal infections, tooth extractions, tooth hypersensitivity, etc.) and conditions that are not directly related to dental and periodontal disease (such as oral candidiosis, pizza burns, tumors, aphthous ulcers, abscesses, denture stomatitis, halitosis, etc.), and including dental esthetics (tooth whitening, etc).

The dermatological conditions of concern to the present invention include fungal infections, bacterial infections, viral infections, burns, insect bites, impetigo, tumors, etc.

Of additional concern in the present invention is a composition and method of controlling the delivery of bone growth factors or alternatively of providing an occlusive membrane over a damage bone and/or tissue, thereby enhancing the regenerative process.

In detail, the invention provides a sustained-release liquid polymer composition which comprises:

(a) a sustained release acrylic polymer;
(b) a release adjusting agent (herein termed a "RAA"); and
(c) a pharmacological agent;

in a pharmaceutically acceptable vehicle, wherein the sustained release acrylic polymer is selected from the group consisting of EUDRAGIT L, EUDRAGIT S, EUDRAGIT RL, and EUDRAGIT RS.

The invention further concerns the embodiment of the above-described composition wherein the pharmacological agent is selected from the group consisting of: an antibiotic, an antiseptic, an anti-fungal agent, an antiviral agent, a bone and/or tissue growth factor, an antitumor agent, an anti-inflammatory agent and a hypersensitivity agent.

The invention also concerns the embodiment of the above-described composition wherein the pharmacological agent is a bacteriocidal quaternary ammonium salt such as cetylpyridinium chloride or benzalkonium chloride or other bacteriocidal agent such as camphorated p-Chlorophenol (CPK).

The invention also concerns the embodiment of the above-described composition wherein the pharmacological agent is a hypersensitivity agent (for example, a strontium salt such as strontium chloride or strontium citrate), a potassium salt (such as potassium chloride, potassium hydrogen tartrate, or potassium nitrate), a fluoride (such as stannous fluoride), or oxylates (such as potassium hydrogen oxylates).

The invention also concerns the embodiment of the above-described composition wherein the pharmaceutically acceptable vehicle comprises an agent selected from the group consisting of water; ethyl alcohol; and ethyl alcohol and water.

The invention also concerns the embodiment of the above-described composition which additionally contains a plasticizer, or polyethylene glycol or dibutyl phthalate.

The invention also concerns the embodiment of the above-described composition where the release adjusting agent is selected from the group consisting of: a cross-linking agent, a polysaccharide, a lipid, a polyhydroxy compound, a protein such as Byco E or Byco C and an amino acid (for example, arginine or lysine), or a combination of the above release adjusting agents.

The invention also provides a method of oral plaque prevention comprising topical application of the aforementioned liquid polymer composition to the teeth or gingival tissues of an animal or human.

The invention also provides a method of treating oral infection comprising topical application of the aforementioned liquid polymer composition to the oral cavity of an animal or human.

The invention also provides a method of treating tooth hypersensitivity comprising topical application of the aforementioned liquid polymer composition to the teeth or gingival tissues of an animal or human.

The invention also provides a method of achieving root canal sterilization comprising topical application of the aforementioned liquid polymer composition to the teeth or gingival tissues of an animal or human.

The invention also provides a method of treating a dermatological disease or condition comprising topical application of the aforementioned liquid polymer composition to the skin of an animal or human.

The invention also provides a method of treating a dermatological disease or condition comprising topical application of the aforementioned liquid polymer composition to a mucosal tissue of an animal or human.

The invention also provides an absorbent point, gauze, or film in combination with a controlled-release composition containing a liquid polymer and an active agent, especially CPK.

BRIEF DESCRIPTION OF THE FIGURES

FIG. 25 shows the effect of $CaCl_2$ on the in vitro release of chlorophenol from polymer-coated paper tissues.

DETAILED DESCRIPTION OF THE PREFERRED EMBODIMENTS

Figure 1:
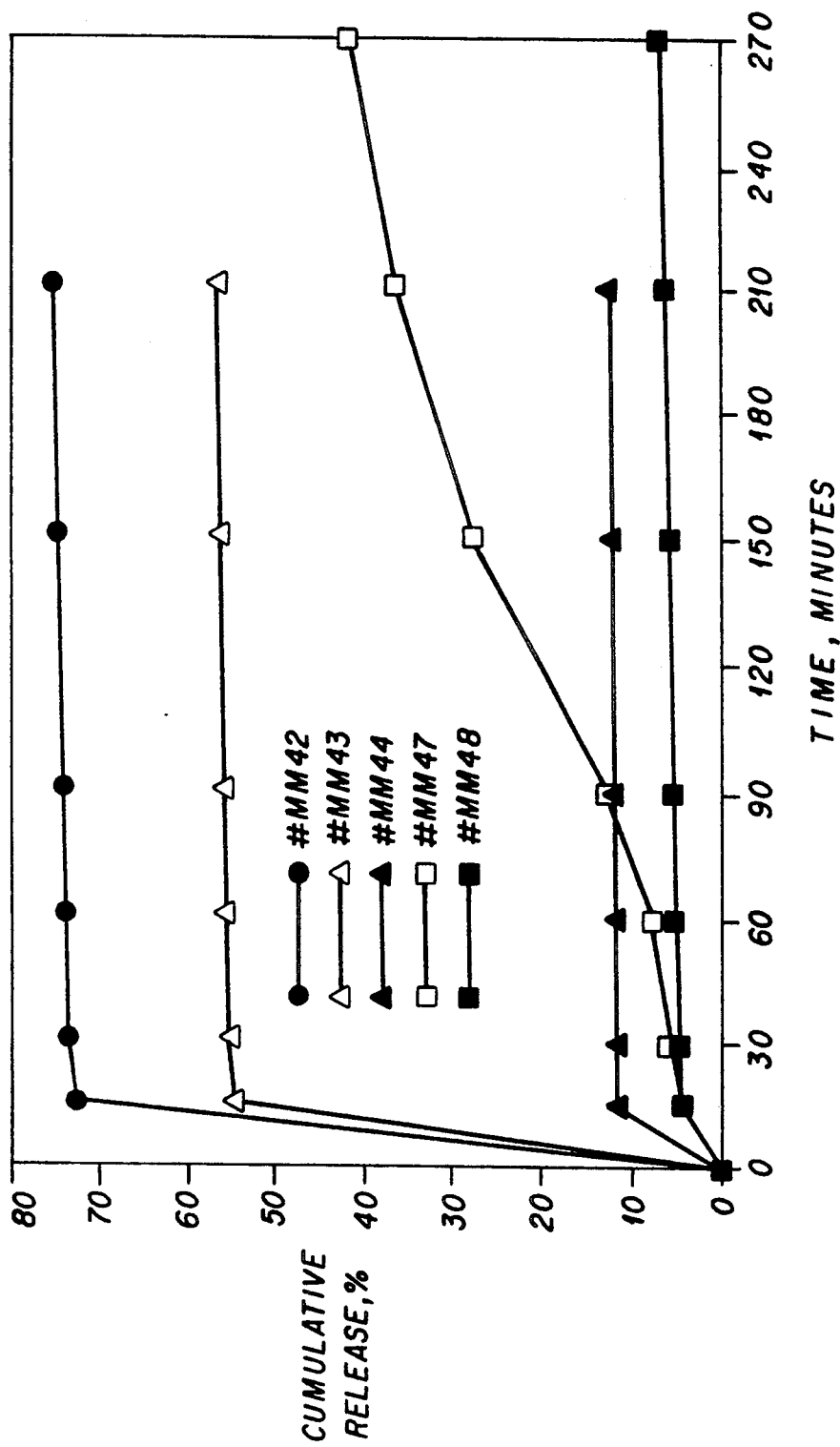
FIG. 1 shows the cumulative release percentage of cetylpyridinium chloride (CPC) from the films produced by the drying of 5 liquid polymer compositions.

The following names are used in this application and are trademarks: EUDRAGIT TM, Byco TM, Teflon TM, UVIKON TM, Kimwipes TM, Teflon TM, Tween 80 TM, and Dentsply TM.

I. The General Nature of the Liquid Polymer Composition

The present invention concerns a composition comprising a non-biodegradable, liquid polymer (referred to as a "varnish" in U.S. patent application Ser. No. 07/369,223). The composition may be designed to be degradable or non-degradable. By a composition which is degradable but non-biodegradable is meant a composition which is slowly solublized but which is resistant to enzymatic degradation in vivo. By a composition which is non-degradable is meant a composition which is neither soluble nor biodegradable.

The invention is derived, in part, from the inventors' discovery that the properties of liquid polymethacrylate polymers, and especially of EUDRAGIT, can be altered to allow for their use as in oral and dental compositions. Specifically, the invention is derived, in part, from the inventors' discovery that such polymers can be altered to be less hydrophilic and more hydrophobic. Further, the invention is derived, in part, from the inventors' discovery that such polymers may be altered to provide a controlled, sustained-release of an active agent by the inclusion of a release adjusting agent. As a result of these alterations, the rate of release of active agents is controlled in a manner desirable for oral and dental use. Compositions containing such polymers may therefore be used to provide efficacious levels of a dental or dermatological agent to a subject in need of such treatment.

In a preferred embodiment, the liquid polymer composition of the invention further contains one or more desired "pharmacological agents" whose sustained release is desired. Such agents may include an anti-fungal, antibiotic, antiseptic, antiviral, anti-inflammatory, anti-tumor, or other pharmacological agent, bone growth factors, tissue growth factors, a metal salt or other agent to treat tooth hypersensitivity, or, in general, any agent suitable for treating a dental and/or dermatological condition.

In a preferred embodiment, the release adjusting agent is selected from (1) a cross-linking agent, (2) a polysaccharide, (3) a lipid, (4) a polyhydroxy compound, (5) a protein such as Byco E or Byco C, (6) an amino acid, or (7) a combination of the above release adjusting agents.

The agent(s) is embedded in a sustained release carrier composed of a polymer. Suitable polymers include an acrylic polymer, a hydrophilic acrylic polymer, a hydrophobic acrylic polymer, or a combination of such acrylic polymers, in a pharmaceutically acceptable vehicle.

The carrier may optionally, and preferably, contain one or more agents such as a plasticizer (such as polyethylene glycol, dibutyl phthalate, etc.).

In additional, the composition may contain an adhesive polymer (such as gum mastic, etc.), or a flavorant, and/or a coloring agent. It is additionally possible to include anti-inflammatory agents, analgesics, and anesthetics into the composition so as to relieve or prevent inflammation, lessen pain, etc.

The compositions of concern to the present invention are termed "liquid polymer" compositions. Such compositions are liquids which (by polymerization, evaporation, etc.) become solidified to produce a film. In accordance with the present invention, such films have the capacity to release a desired pharmacological agent, and thereby provide treatment for, or prevent, a particular disease or condition. The solidified films are capable of releasing the pharmacological agent over a substantial period of time (i.e., hours or months, depending upon the composition). Thus, such films are sustained release devices.

The "liquid polymer" composition of the present invention is a composition which is preferably topically applied to a surface such as a tooth, to skin, to a mucous membrane (oral, vaginal, rectal, etc.), and the like, as by brush, spray, etc., and which dries as a film adhering to that surface, in a manner which resists removal under normal conditions, such as eating or brushing, for applications to the teeth and oral mucosa, or normal washing and abrasion, when applied to skin. Alternatively, the composition may be applied to bandages, dressings, gauze, brushes, implants, etc. and permitted to dry into a film in advance of its administration to a patient. Although the solidified liquid polymer composition is referred to as a "film," it is to be understood that the thickness of the film may be varied or increased by multiple applications of the liquid polymer. Thus, for example, it is possible to produce a "film" which can fill wounds, cuts, abscesses, tooth sockets, etc.

The release adjusting agent ("RAA") is an agent whose presence in the liquid polymer composition serves to adjust the release rate of the pharmacological agent. As indicated above, it may be a cross-linking agent (such as glutaraldehyde, citric acid, lysine, aspartic acid, glutaric acid, etc.), or a polysaccharide (such as dextran, etc.), or a lipid (such as sodium docusate, etc.), or a polyhydroxy compound (such as polyethylene glycol, glycerol, propylene glycol), or a protein such as Byco E or Byco C.

For use in the treatment of tooth hypersensitivity, a preferred RAA is sodium citrate which is used to control the release of strontium from the dried film; the concentration of sodium citrate in the film controls the release rate of the strontium. Sodium docusate is an alternative RAA for tooth hypersensitivity uses of the liquid polymer composition of the present invention. RAA are preferably provided to those liquid polymer compositions which are to be used for dermatological uses as a means for compensating for the lack of humidity in the skin.

By "oral cavity" is meant the mouth and the surrounding esophageal area. Therefore, for example, the oral cavity includes the tongue, gums, palate, throat teeth, tonsils and periodontal tissue.

By "sustained-release" is meant the continuous release of an active substance at efficacious levels for a prolonged period of time, such as for one hour or longer for the case of plaque prevention, or as much as 2–4 weeks or longer for other purposes. The release of the active substance may be constant or pulsed, as long as efficacious levels of the active substance are provided to the surrounding milieu for the desired period of time.

The pharmacological agents of the liquid polymer compositions of the present invention include any of a wide variety of antibacterial agents, antifungal agents, and antiviral agents, as well as agents for root canal sterilization, antisepsis, or for the treatment of tooth hypersensitivity. As used herein, the term "antibacterial agent" includes both bacteriocidal and bacteriostatic agents. Such agents are, as indicated above, effective in the treatment or prevention of oral or dermatological diseases and conditions. An agent is said to be effective in the treatment of a disease or condition, if its administration to a patient exhibiting the disease or condition results in a decrease in the severity or duration of the disease or condition. Likewise, an agent is said to be effective in the prevention of a disease or condition, if its administration to a patient at risk for the disease or condition results in a decrease in such risk.

By an "effective" or "efficacious" level is meant a level or concentration of a drug or other active agent which is high enough to be effective in treating the condition the drug was designed to treat. The particular formulation of the liquid polymer composition will, thus, determine the particular use for which it is suitable.

Of particular interest to the present invention are liquid polymer compositions containing anti-fungal, antibacterial, or anti-viral agents, or growth promoting agents for bone and/or tissue. When used for oral or dermatological purposes, any topically applicable or systemically tolerated antiseptic or antibiotic may be empolyed. Suitable agents are described in *Goodman and Gilman's The Pharmacological Basis of Therapeutics*, A.G. Gilman et al. (eds.), Macmillan Publ. Co., N.Y. (1985), which reference is incorporated herein by reference).

A variety of antifungal agents are suitable for the present invention. Preferred are the polyene antifungals, especially nystatin and amphotericin B. Examples of other antifungal agents applicable to the methods of the invention include 5-fluorocytosine and imidazole- and triazole-derivative antifungal agents, especially naftifine, terbinafine, tolnaftate, tolciclate, isoconazole, sulconazole, miconazole, clotrimazole, econazole, bifonazole, oxiconazole, tioconazole, ketoconazole, miconazole nitrate, itraconazole, fluconazole, and terconazole, all known to the art. See, for example, Kostiala, I. et al., *Acta Odontol. Scand.* 37;87–101 (1979). Additional anti-fungal agents which may be employed include amphotericin B, nystatin, flucytosine, griseofulvin, hydroxystilbamine isethionate, derivatives of undecylenic, benzoic, propionic, caprylic or salicylic acid, ciclopirox olamine, haloprogin, hexylresourcinol and its derivatives (such as acrisorcin, etc.), natamycin, carbolfushin, resorcinol, sulfur, aminacrine hydrochloride, gentian violet, iodine, iodoquinol and clioquinol, etc.

In another embodiment, combinations of more than one antifungal agent are used in the composition of the invention. Combinations of antifungal agents can for the purpose of providing treatment or protection against a broad spectrum of microfungal species, or for the purpose of attacking a specific microfungal species with drugs acting through different modes of action. Combination of antifungal agents may also allow a lower dose of a given antifungal agent to synergistically act with a lower dose of another antifungal agent in a manner which is efficacious in combination but not separately.

Examples of suitable antibacterial agents which may be employed in accordance with the present invention include the pencillins and ampicillins, clindamycin, erythromycin, tetracycline, vancomycin, chloramphenicol, trimethoprim, aminoglycosides (such as gentamycin, streptomycin, neomycin, kanamycin, etc.), polymyxin B, etc.

Examples of suitable antiviral agents which may be employed in accordance with the present invention include acyclovir, idoxuridine, salicylic acid and its derivatives, amantadine, ribavirin, interferons, etc.

In addition to the above-described agents, non-specific disinfectants and antiseptics may be employed in the liquid polymer compositions of the invention. Such agents may be used for the treatment of oral or dermatological diseases and conditions if their administration can be tolerated by the patient without unacceptable side effects. Examples of suitable disinfectants include chlorhexidine (and especially chlorhhexidine digluconate), chlorine and chlorofors, iodine and iodophors, silver compounds (such as silver nitrate, silver sulfadiazine, etc.) mercury compounds (such as merbromin, thimerosol, mercuric chloride, ammoniated mercury, etc.), zinc compounds (especially zinc oxide), nitrofurazone, phenols, anthralin, benzoyl peroxide, hydrogen peroxide, quaternary ammonium compounds, etc. Cetylpyridinium chloride and benzalkonium chloride are preferred agents.

The liquid polymer compositions of the present invention may alternatively contain photo-absorbing agents (such as para-aminobenzoic acid and the like) such that they may be used in the prevention of sunburn. Likewise, they may contain cosmetic agents (such as anti-wrinkle agents, moisturizing agents, etc), such that they may be used as cosmetics.

A "hypersensitivity agent" is an agent which is capable of treating tooth hypersensitivity when provided in an effective amount to a recipient in need of such treatment. Any of a variety of anti-hypersensitivity agents are suitable for the present invention.

The liquid polymer compositions of the present invention may contain only a single pharmacological agent, or they may have any number of agents; such multiple agents may be of the same type (for example, all being anti-fungal agents), or they may be of different types (for example, an antibacterial agent and an anti-fungal agent). Any combination of agents may be employed.

II. The Polymer of the Liquid Polymer Compositions

The sustained release of the above-described agents is, in accordance with the present invention, preferably accomplished by embedding the agent in an acrylic polymer, or a hydrophilic acrylic polymer, or a hydrophobic acrylic polymer or a combination of such acrylic polymers, in the presence of a release adjusting agent, to form a liquid polymer composition which is compatible with tissues in the oral cavity and with dermatological use.

Polymers of special interest to the present invention include hydrophilic polymers such as polymethacrylates containing more than 50% methacrylic acid monomers, relatively hydrophilic polymers such as polymethacrylics containing quaternary amine groups, and combinations of such hydrophilic and hydrophobic polymers in various ratios.

EUDRAGIT is a non-biodegradable, polymethacrylate polymer (Roehm Pharma GmbH, Darmstadt, Federal Republic of Germany) which may be formulated to disintegrate or dissolve in water, saliva, etc. EUDRAGIT exists in four forms: S, L, RS and RL (*Drugs and the Pharmaceutical Sciences* vol. 36, McGinity, J.W.

(ed.), Marcel Dekker, Inc., N.Y. (1989); Chafi, N. et al., *Drug Dev. Ind. Pharm.* 15:629-648 (1989); Chang, R.K., et al., *Drug. Dev. Ind. Pharm.* 15:361-372 (1989); Thoennes, C.J. et al., *Drug. Dev. Ind. Pharm.* 15:165-186 (1989); Silva, J.F.P.D. et al., *Folha Med.* 97:253-257 (1988); Larroche, C. et al., *Enzyme Microb. Technol.* 11:106-112 (1989); Rachmilewitz, D. et al., *Brit. Med. J.* 298:82-86 (1989); Goto, S. et al., *J. Microencapsul.* 5:343:360 (1988); which references are incorporated herein by reference).

EUDRAGIT RL and RS are water insoluble copolymers synthesized from acrylic and methacrylic acid esters with a low content of quaternary ammonium groups. These polymers form non-degradable or non-disintegrating films. If more hydrophilic polymer is added to the film, such as EUDISPERT ® (Dittgen, M. et al., *Pharmazie* 41:883-884 (1987); Kristl, J. et al., *Acta Pharm. Technol.* 33:140-144 (1987), which references are incorporated herein by reference ), EUDRAGIT S or EUDGRAGIT L, a different sort of film can be formed which could disintegrate.

EUDRAGIT L (or S) and EUDISPERT are anionic co-polymers based on methacrylic acid and methyl methacrylate. EUDISPERT L is soluble in buffer solutions above pH 6.0. Due to the fact that EUDISPERT is a polycarboxylic acid salt which could react with cationic drugs, it is not preferable to prepare films from liquid polymers containing EUDISPERT polymer alone. EUDISPERT was used successfully as an additive, however, for altering drug release from films. EUDRAGIT L, in contrast, formed nice and homogeneous films which degraded in phosphate buffer pH 6.8.

EUDRAGIT L is a methacrylic acid type A copolymer, an anionic copolymer based on methacrylic acid and methylmethacrylate wherein the ratio of free carboxyl groups to the ester groups is approximately 1:1. EUDRAGIT S is a methacrylic acid type B copolymer, an anionic copolymer based on methacrylic acid and methylmethacrylate wherein the ratio of free carboxyl groups to the ester groups is approximately 1:2. EUDRAGIT RL is a dimethylaminoethylacrylate/ethylmethacrylate copolymer, a copolymer based on acrylic and methacrylic acid esters with a low content of quaternary ammonium groups wherein the molar ratio of the ammonium groups to the remaining neutral (meth)acrylic acid esters is 1:20. EUDRAGIT RS is an ethyl methacrylate/chlorotrimethylammoniumethyl methacrylate copolymer, a copolymer based on acrylic and methacrylic acid esters with a low content of quaternary ammonium groups wherein the molar ratio of the ammonium groups to the remaining neutral (meth)acrylic acid esters is 1:40.

Although all of the four forms of EUDRAGIT are hydrophilic, it is harder to dissolve the RL/RS forms, then the L/S forms, in saliva. Thus, for oral and dental uses, it is therefore preferable to add a plasticizer (such as, for example, polyethylene glycol, dibutyl phthalate, etc.) to the RL/RS form polymers in order to increase the rate of solubility of the R forms in saliva.

In order to increase the rate of degradation, and to increase the release of drug, it is possible to add agents such as citric acid, lysine, aspartic acid, glutamic acid, glutaric acid, etc.

The EUDRAGIT S or EUDRAGIT L polymers are highly soluble in buffer solutions. Lysine, citric acid, and divalent cations of calcium, strontium, etc., are each capable of cross-linking EUDRAGIT S or EUDRAGIT L polymers. Thus, such agents can be added to such polymers in order to decrease the rate of dissolution of the polymer. For oral and dental purposes, the preferred polymers of the present invention are polymethacrylates such as EUDRAGIT ® and EUDRAGIT(L). EUDRAGIT(R) is the preferred polymer for dental and oral purposes. For dermatological purposes, any of the four EUDRAGIT polymers may be employed (i.e. (S), (L), (RL) and (RS)).

In another embodiment of the present invention, the compositions may also contain additional desirable components. For example, if desired, the adhesiveness of the composition may be improved by the incorporation within said composition of gums such as gum mastic in a formulation providing from 1-20% by weight of the gum mastic. Other suitable mastics are disclosed in U.S. Pat. No. 4,315,779 to Heyd, D., et al., and U.S. Pat. No. 4,374,844 to Wahmi, H.V.R., et al.

Likewise, the compositions may contain demulcents/humectants (i.e., plasticizers) such as polyethylene glycol 400-to-4000, glycerol, sorbitol, or mineral oil in concentrations of about 1% by weight. Other humectants, detergents, or surface-active agents will be known to those skilled in the formulation of oral compositions. Polyethylene glycols or dibutyl phthalate are the preferred optional plasticizers of the invention. Such agents play a role in enhancing the rate of degradation of the film and improving its adherence.

For application to buccal or lingual surfaces of teeth, or to mucosal tissue, the liquid polymer (containing a suitable pharmaceutical agent) may be applied by spray, soft brush, etc. Solvent may be evaporated by a gentle stream of warm air, or by other means.

For application to orthodontic appliances, a total of about 70 mg of bacteriocidal agent, dissolved in polymer may be applied per appliance with a soft brush or spray, and residual solvent removed with a gentle stream of warm air.

Those skilled in the art will, without undue experimentation, be able to produce ranges of concentrations of appropriate agents and sustained release polymers.

III. Uses for the Liquid Polymer Compositions of the Invention

A. Oral and Dental Uses

The use of antibacterial and hypersensitivity agents, for dental purposes, in certain hydrophilic or acrylic polymer based sustained release compositions is disclosed in U.S. patent applications Ser. Nos. 07/189,918, and 07/304,091 which applications are herein incorporated by reference.

The use of the above-described polymers of the present invention has the advantage of minimizing side effects such as staining of teeth and dentures and unpleasant taste (see, for example, Friedman, M., et al., *J. Dent. Res.* 64:1319-1321 (1985)). The liquid polymer compositions of the present invention are intended for use in the treatment or prevention of oral and/or dental diseases or conditions.

1. Plaque and Caries

Plaque and caries are among the dental diseases or conditions which may be treated or prevented through the use of the liquid polymer compositions of the present invention. One preferred composition of the present invention for oral use contains an anti-plaque or anti-caries agent, and is designed for oral use in the treatment of plaque or caries. An agent is an anti-plaque agent, or an anti-caries agent, if, when provided in an effective amount to a recipient, it is capable of preventing or attenuating the accumulation of plaque or caries. Preferred for such use are the cationic nitrogen-containing antibacterial materials that are well known to the art. See, for example, the section on "Quaternary-Ammonium and Related Compounds" in the article on "Antiseptics and Disinfectants" in Kirk-Othermer Encyclopedia of Chemical Technology, 2nd ed. (Vol. 2, pp. 632–5), incorporated herein by reference. Such materials have been used in oral compositions to counter plaque formation caused by bacteria in the oral cavity. Among the most common and efficacious of these antibacterial, anti-plaque quaternary ammonium compounds are cetylpyridinium chloride and benzalkonium chloride. Other cationic ammonium antibacterial agents of this type are mentioned, for instance, in U.S. Pat. Nos. 2,984,639, 3,325,402, 3,431,208, 3,703,583, and 4,339,430, British Patent No. 1,319,396, and German Patent No. 2,332,383. Most preferred is cetylpyridinium chloride, which is efficacious, compatible with the other components of the oral composition, and inexpensive by virtue of being a non-prescription drug.

In yet another embodiment, the composition may contain an oxygenating agent. Such as agent will be present in an amount capable an anti-caries, anti-plaque or antiseptic-like effect. Examples of suitable oxygenating agents include urea peroxide, hydrogen peroxide (Cameron, J.A. et al., *Austral. Dent. J.* 29:80–85 (1984); Firestone, A.R. et al., *Caries Res.* 16:112–117 (1982); Futaki, S. et al., *Shikwa Gakuho* 80:487–495 (1980)), carbamide peroxide (Ullmann, E. et al., *Somatol. DDR* 33:334–341 (1983)), peroxyborate monohydrate (Addy, M. et al., *J. Clin. Immunol.* 5:272–277 (1978); Dill, H. et al., *Int. J. Clin. Pharmacol. Biopharm.* 15:17–18 (1977)), and peroxydiphosphate (Afflitto, J. et al., *J. Dent. Res.* 67(Spec. Iss. March):401 (1988); Coleman, E.J. et. al., *J. Dent. Res.* 67(Spec. Iss. March):296 (1988); Nabi. N. et al., *J. Dent. Res.* 67(Spec. Iss. March):151 (1988)).

The compilation of the components of the aforementioned oral composition is based upon the specific properties of each of the individual components, wherein each component of the combination increases the anti-plaque effectiveness of other members of the combination.

The oral composition of the invention assists in the prevention of dental caries and periodontal disease, and in the relief of symptoms resulting from existing gingival and subgingival problems, by attacking the pathogenic bacteria responsible for plaque formation and consequent cariotic and periodontal diseases.

The composition effective for the treatment or prevention of plaque, dental caries or periodontal disease is such that the antibacterial agent can be released in a sustained, long-term fashion, and such that the antibacterial composition has the property of long-term adhesion to the gums and teeth, and such that the antibacterial composition remains plastic during the entire period of application.

It is also a feature of this invention that the aforementioned bacteriocidal anti-plaque agent is released to the sites of carious lesions and periodontal pockets in a long-term sustained release manner so as to reduce the required frequency of use.

The compositions of the invention are especially useful in the treatment of gingivitis in animals, and especially pets. The major cause of death in the U.S. of dogs and cats over four years old is starvation due to tooth loss. The composition of the invention may be formulated to contain an anti-bacterial agent, and preferably chlorhexidine, and applied to the teeth of animals with an applicator, so as to help treat or prevent against gingivitis-induced tooth loss.

2. Tooth Hypersensitivity

As indicated above, a variety of anti-hypersensitivity agents are suitable for the present invention. Preferred is the use of strontium salts. Other anti-hypersensitivity agents useful in the composition of the invention include potassium, lithium or sodium nitrate, potassium bicarbonate, potassium chloride, hydroxyapatite, fluorapatite, ammonium oxalate, EDTA with fluoride, fluoride, and ammonium glycyrrhizzinate. In a composition effective for the treatment or prevention of tooth hypersensitivity, the active anti-hypersensitivity agent is released in a sustained, long-term fashion, without a salty or metallic taste. The hypersensitivity composition has the property of long-term adhesion to the teeth, and is able to remain plastic during the entire period of application.

3. Oral Candidiasis and Other Oral Fungal Infections

The liquid polymer composition of the present invention may be employed in the treatment or prevention of oral candidiasis as well as other oral fungal diseases. The oral composition of the invention assists in the prevention of microfungal infections of the oral cavity and periodontal tissue, and in the relief of symptoms resulting from existing microfungally-caused problems, by attacking the pathogenic yeast and fungi responsible for the infection in the oral cavity. As indicated above, a variety of antifungal agents are suitable for the present invention. In addition to the treatment and prevention of oral infections, the liquid polymer compositions of the present invention may be used to treat fungal infections which affect other mucosal tissue. For example, the liquid polymer composition of the present invention may be used in the treatment of yeast, chlamydial, etc. infections of the vagina.

In another embodiment, combinations of more than one antifungal agent are used in the composition of the invention. Combinations of antifungal agents can for the purpose of providing treatment or protection against a broad spectrum of microfungal species, or for the purpose of attacking a specific microfungal species with drugs acting through different modes of action. Combination of antifungal agents may also allow a lower dose of a given antifungal agent to synergistically act with a lower dose of another antifungal agent in a manner which is efficacious in combination but not separately.

The antimycotic composition may be formulated to include other drugs such as antibacterial or antiseptic agents also known to the art.

One feature of this invention is that the aforementioned antifungal agent is released to the sites of fungal lesions and pockets in a long-term sustained release manner so as to reduce the required frequency of use. Long-term sustained release is desirable because it improves patient compliance with the treatment protocol and it is more convenient for the patient. Hence the success of the treatment is more probable. The method of the invention needs only a single or few applications of the liquid polymer composition to remain efficacious for a period of weeks. Other methods require a multi-dose application of paste every few days or ingestion of lozenges every four hours by the patient. At best, the pastes remain effective for 2–3 days and the lozenges only for hours.

In addition, by the composition and method of the invention, because of the long-term sustained release of the drug, much lower amounts of the antifungal drug are required for efficacious results. Conventional therapy uses doses of nystatin as high as $10^8$IU/dose. In contrast, substantially lower doses are efficacious when used in the liquid polymer compositions of the present invention. Because of the lower doses of nystatin, the side effects of the drug are eliminated or minimized. For example, at the efficacious concentrations of nystatin taught by the compositions and methods of the invention, the bitter taste associated with nystatin is found to be substantially less objectionable. The bitter taste of the drug is one of the major complaints of patients taking conventional nystatin therapy.

Moreover, the physical form and manner of presentation of the composition of the invention is highly advantageous for a patient with an oral microfungal infection. Often the area of the infection is so sore so as to make the direct application of a paste or even sucking lozenges, troches or pastilles very painful; rinsing with a mouthwash does not leave efficacious levels of the drug in the oral cavity. In other cases, oral treatments with mouthwashes, lozenges, pastes, troches or pastilles is very difficult or just not practical, for example with infants or animals. The compositions and methods of the invention solve this problem by applying the antifungal drug to the teeth or other orthodontic apparatus, for slow, long-term sustained release at efficacious levels into the salival fluids of the oral cavity.

4. Sterilization of Root Canals

In addition to the above-described uses, the liquid polymer compositions of the present invention can be employed as a means of sterilization for root canal procedures. For such treatment, the composition would preferably include an antiseptic agent (most preferably camphorated parachlorophenol (CPK). Use of the composition of the invention with CPK provides a highly-desired prolonged period of effectiveness for such treatment. For example, in the typical procedure wherein CPK is currently used to sterilize root canals, a paper point is dipped into CPK and inserted into the root canal which is then closed with a temporary filling. The anti-bacterial agent in that case is only effective for a few hours. However, utilizing the composition and method of the invention, wherein the liquid polymer is used as a matrix for CPK, the anti-bacterial agent is released in an active form for a period of 3-4 days, thus making the sterilization process more effective.

Further, it is possible to design a degradable polymer system simply by replacing EUDRAGIT S (polymer type B) with EUDRAGIT L (polymer type A), and injecting the liquid into the root canal.

5. Other Oral/Dental Uses

The compositions can also be used to treat or prevent infection in the socket of an excised wisdom tooth, or in a gingival abscess. The liquid polymer can be injected directly into the periodontal pocket, forming a film in situ and releases the active material in a controlled manner over a desired period of time. As described herein, the compositions of the invention may be formulated so that, simultaneous with the controlled-release, the film disintegrates. By injecting the liquid polymer in this way, the film forms in the shape of the pocket and the amount of liquid polymer needed can be determined by the pocket size. Thus, there is no need for predetermination of the amount to be administered as there is with a "chip." Also, this liquid polymer is especially appropriate to use with small pockets (those less than 4 mm in depth), rather than creating a smaller chip especially sized for the small area. For this purpose, the composition would contain an antiseptic, an antibacterial, an anti-inflammatory agent, an analgesic, and/or an antifungal agent (chlorhexidine digluconate is the preferred agent).

The invention also provides an absorbent point, gauze, or film in combination with a controlled-release composition containing a liquid polymer and an active agent, especially CPK.

The compositions may also be adapted to treat denture stomatitis (Arendorf, T.M. et al., *J. Oral Rehabil.* 14:217-227 (1987); Stohler, C., *Schweiz Monatsschr Zahnmed*, 94:187-194 (1984), which references are incorporated herein by reference), by containing an antifungal agent (most preferably nystatin). The compositions can be adapted to treat aphthous ulcers (Brazelton, F., *GMDA Bull* 50:219-220 (1983); Chawda, J.G. et al., *Ann. Dent.*:43:14-17 (1984), which references are incorporated herein by reference), canker sores, or burns (as from food such as pizza, molten cheese, etc.) by the inclusion of saccharin and ethyl alcohol and/or cetylpyridinium chloride. Chlorhexidine gluconate may alternatively be employed for this purpose (mouthrinses containing chlorhexidine gluconate have been used to treat candida infections as reported by Addy, M. et al. in *J. Clin. Periodont.* 14:267-273 (1987), which reference is incorporated herein by reference).

The composition of the invention, because of its ability to adher to gums and to deliver agents for the treatment of pain and inflammation, may also be used to treat teething pain in children.

The composition of the invention can also be used for dental esthetics, for example, tooth whitening. Such whitening can be performed by using the composition of the invention to continuously deliver low levels of a bleaching or oxidizing agent directly to the enamel surface of the tooth crown. Examples of such oxidizing and bleaching agents include chlorine peroxide, hydrogen peroxide and urea peroxide. Use of the composition of the invention for such purposes is more efficient and exposes the patient to fewer toxic risks than present methods.

In a manner analogous to the treatment of oral fungus conditions, the compositions of the invention may also be used to deliver efficacious levels of an anti-tumor agent to a tumor in the oral cavity. Such compositions may be applied as a varnish directly to the tumor and/or applied at a location wherein efficacious levels of the anti-tumor agent are released into the milieu surrounding the tumor. If desired, multiple coatings of films may be used. For example, a first layer of the anti-tumor-containing composition may be applied directly upon the site of the tumor, so that a film is formed over the site of the tumor, and the first layer then coated with a second layer which provides properties different from those of the first layer. For example, the second layer may be impermeable to the anti-tumor agent so as to only permit delivery of the anti-tumor agent from the side of the film which faces the tumor, or the second layer may provide a second active agent and/or provide for a rate of release of an active agent which is different from that of the first layer.

B. Dermatological Uses

The liquid polymer compositions of the present invention may be empolyed in the treatment or prevention of dermatological diseases or conditions. As used herein, a dermatological disease or condition is one which affects the skin. In one embodiment, the liquid polymer composition may be applied directly to the skin surface. Alternatively, the composition may be applied to a bandage, dressing, etc. and then placed in contact with the affected skin surface.

The liquid polymer of the invention can be used for the delivery of bone growth factors and tissue growth factors or alternatively to provide an occlusive membrane over damaged bone and/or tissue, thus enhancing the regenerative response.

Examples of dermatological diseases and conditions which may be treated or prevented by use of the present invention includes acne vulgaris, insect bites, impetigo, burns, ringworm, tinea versicolor, cutaneous candidiasis, molluscum contagiosum, sunburn, allergic contact dermatitis (such as a reaction to poison ivy, poison oak, bee venom, etc.), exfoliative dermatitis, eczematous dermatitis, warts, herpes simplex or zoster lesions, chicken pox lesions, rubella macules or papules, pustules, psoriasis, Lyme disease lesions, general inflammatory responses (i.e. rashes, etc.), urticaria, erythema multiforme syndrome, purpura, skin tumors, etc. Further examples of dermatological diseases or conditions which may be treated or prevented using the liquid polymer compositions of the invention are disclosed in *Harrison's Principles of Internal Medicine*, 11th Edition, Braunwald, E. et al. (eds.), McGraw-Hill, N.Y. (1987), which reference is incorporated herein by reference). The liquid polymer compositions of the present invention can be employed in the treatment of cuts, bruises, and the like, to prevent subsequent bacterial, fungal or viral infection.

The compositions of the present invention are especially well suited for dermal application since thereby are resistant to abrasion and removal by water or perspiration. Such concerns are especially significant in compositions for the treatment of burns, bruises, and sunburn. The water resistant nature of the films formed from the drying of the liquid polymer compositions of the present invention makes such liquid polymer compositions especially suitable for use in the treatment or prevention of sunburn.

Although the foregoing has exemplified the dermatological uses of the invention, it will be understood that the liquid polymer composition of the present invention may be used in the topical treatment of any mucosal surface. Thus, for example, liquid polymer compositions which contain antibiotics or anti-viral agents may be applied to the vagina or penis in the treatment of venereal disease (such as gonorrhea, syphilis, herpes infections, etc.).

In addition to the aforementioned uses, the liquid polymer compositions of the present invention may be used in cosmetics (as by formulating them to contain moisturizing agents, retinoid A (or other anti-wrinkle agents), etc.).

Having now generally described the invention, the same will become better understood by reference to certain specific examples which are included herein for purposes of illustration only and are not intended to be limiting unless otherwise specified.

EXAMPLE 1

Since toothbrushing generally proves to be sufficient in preventing plaque, the use of chemicals which reduce plaque and could be delivered in forms likely to be widely accepted by the general public have been assiduously sought by dental scientists. Many quaternary ammonium salts in the form of mouthwashes, dentifrice, solutions and gels have proven successful in preventing periodontal diseases. Among them, chlorhexidine and cetylpyridinium chloride (CPC) are the most effective against plaque.

Sustained release drug treatment is expected to be efficacious in local and prolonged action rather than the conventional antibacterial therapy (mouthrinse and dentifrice). Thus, a CPC liquid polymer solution which can be spread on the teeth to form a drug-containing film is desirable. The drug is expected to be released into the mouth cavity and into plaque substance which accumulates on teeth. The release should be terminated after a night's sleep (average: 5-6 hours), while at the same time, the film degrades.

In an attempt to assess the in vitro release of CPC from liquid polymer films composed of acrylic polymers, a broad series of experiments were performed in which different polymers and plasticizers and several additives were formulated and tested.

1. Liquid polymer Preparation—General Description

The formulations were all prepared by the same general procedure, described as follows: the polymer (EUDRAGIT®, Roehm Pharma Gmbh, Darmstadt, W. Germany), polyethylen glycol (PEG), and the CPC were dissolved in ethanol. After complete dissolution of these ingredients, additional components in aqueous solution were added, while continuously stirring. The ratio of film components to solvents (water/alcohol) was 1:3.

2. In-vitro evaluation

Liquid polymer solutions containing the requisite weights of CPC and polymer were poured on Teflon plates. The films were generated after allowing the solvent to evaporate for 12-15 hours at room temperature. The films (containing 1-5% water) were cut to rectangular forms of $1 \times 1$ cm in an area and accurately weighed. The films were then placed in vials containing 5 ml phosphate buffer (0.02 M, pH 6.8) previously warmed to 37° C. and incubated for 6 hours. Samples were taken at time intervals of 5, 15, 30, 60, 90, 210, 270, 330, and 360 minutes. The concentration of CPC released was determined by UV spectrophotometer (UVIKON 930, Kontron Instruments) at 254 nm against standard calibration curve.

In these experiments, EUDISPERT mv or EUDRAGIT L was added to the formulations containing CPC and EUDRAGIT RL. EUDISPERT mv and EUDRAGIT L are relatively water-soluble polymers. Table I shows the weight percent of components in films prepared from 5 liquid polymer compositions (i.e. MM42, MM43, MM44, MM47, and MM48). The liquid compositions were dried, and the cumulative percentage of released CPC was determined. FIG. 1 shows the cumulative release percentage of CPC from the films produced by the drying of the 5 liquid polymer compositions.

TABLE I

| Weight percent of components in film formulations | | | | | |
|---|---|---|---|---|---|
| Exp. No. | MM42 | MM43 | MM44 | MM47 | MM48 |
| CPC | 30 | 30 | 30 | 30 | 30 |
| EUDRAGIT RL | 35 | 32.5 | 30 | 40 | 55 |
| PEG 400 | 25 | 25 | 25 | — | — |
| EUDRAGIT L | — | — | — | 30 | — |

TABLE I-continued

| | Weight percent of components in film formulations | | | | |
|---|---|---|---|---|---|
| Exp. No. | MM42 | MM43 | MM44 | MM47 | MM48 |
| EUDISPERT mv | 10 | 12.5 | 15 | — | 15 |

EXAMPLE 2

Figure 2:
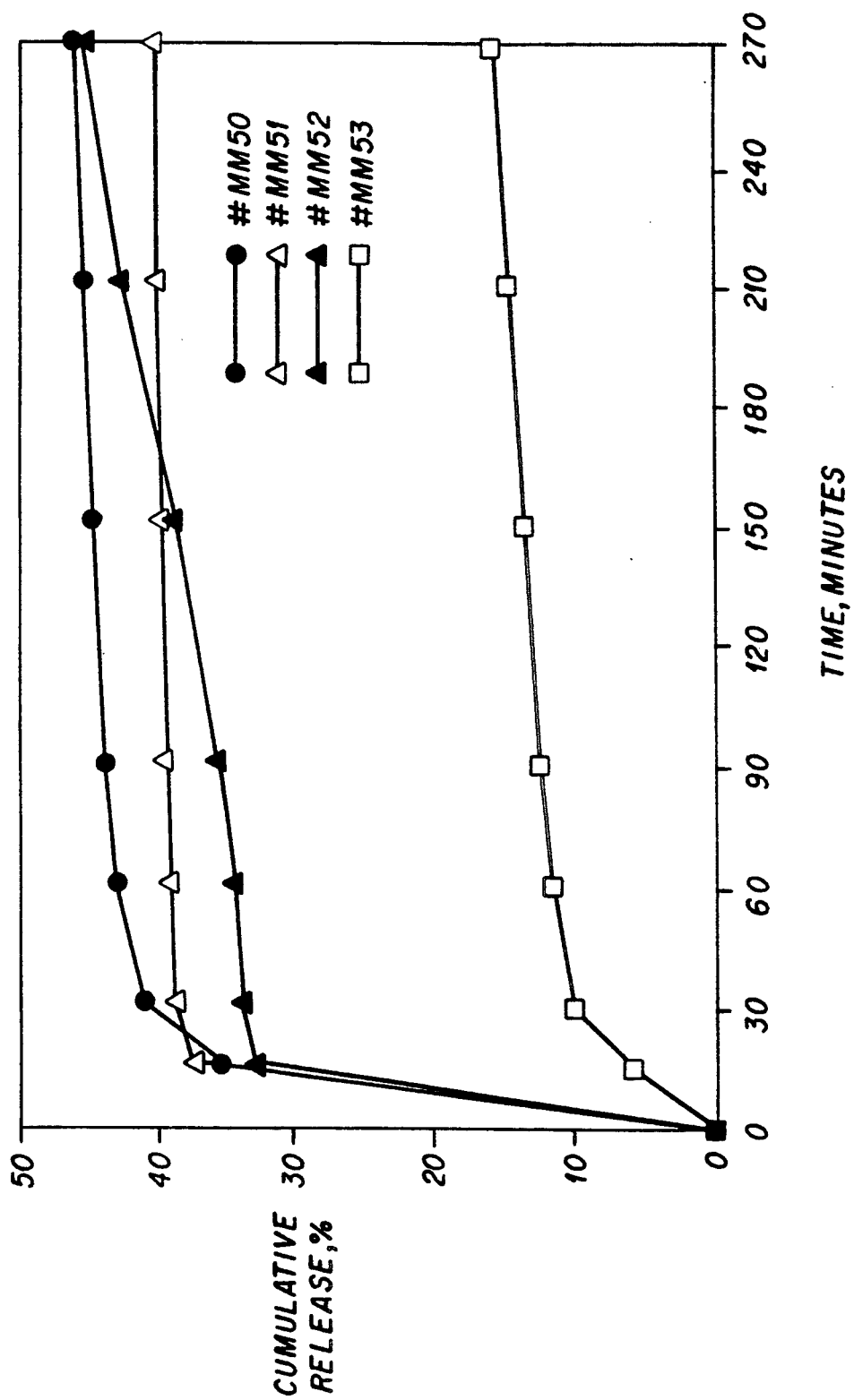
FIG. 2 shows the cumulative release percentage of CPC from the films produced by the drying of 4 liquid polymer compositions.

In these experiments EUDISPERT mv or EUDRAGIT L were added to formulations containing a combination of 50:50 EUDRAGIT RL/EUDRAGIT RS either with PEG 400 or without it. Table II shows the weight percent of components in films prepared from 4 liquid polymer compositions (i.e. MM50, MM51, MM52, and MM53). The liquid compositions were dried, and the cumulative percentage of released CPC was determined. FIG. 2 shows the cumulative release percentage of CPC from the films produced by the drying of the 4 liquid polymer compositions.

TABLE II

| | Weight percent of components in film formulations | | | |
|---|---|---|---|---|
| Exp. No. | MM50 | MM51 | MM52 | MM53 |
| CPC | 30 | 30 | 30 | 30 |
| EUDRAGIT RL | 15 | 25 | 20 | 30 |
| EUDRAGIT RS | 15 | 25 | 20 | 30 |
| PEG 400 | 10 | 10 | 20 | 30 |
| EUDRAGIT L | 30 | — | 30 | — |
| EUDISPERT mv | — | 10 | — | 10 |

EXAMPLE 3

Figure 3:
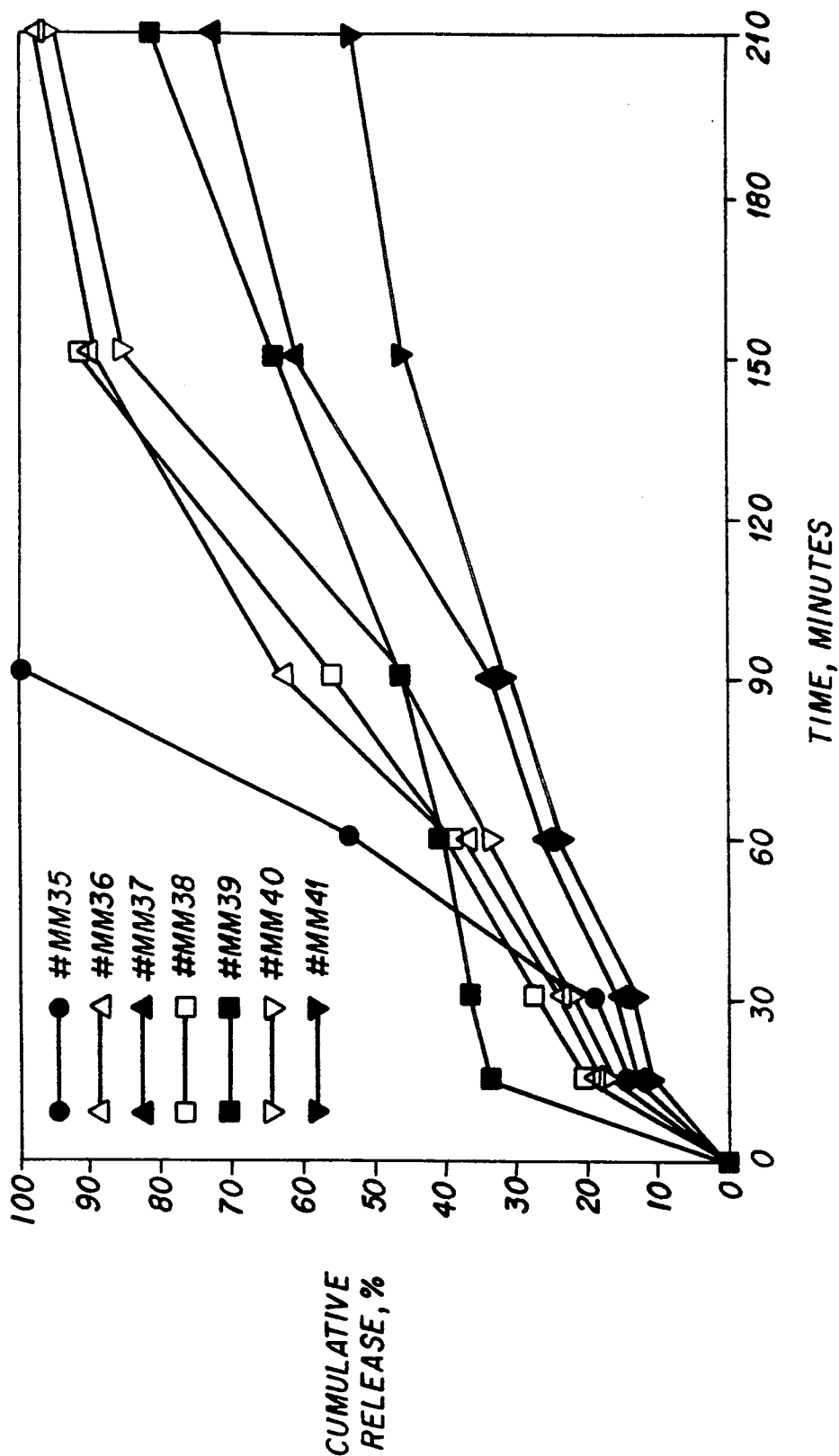
FIG. 3 shows the cumulative release percentage of CPC from the films produced by the drying of 7 liquid polymer compositions.

This example involved various Eduispert mv concentrations in formulations containing CPC, EUDRAGIT L and PEG 400. Table III shows the weight percent of components in films prepared from 7 liquid polymer compositions (i.e. MM35, MM36, MM37, MM38, MM39, MM40 and MM41). The liquid compositions were dried, and the cumulative percentage of released CPC was determined. FIG. 3 shows the cumulative release percentage of CPC from the films produced by the drying of the 7 liquid polymer compositions.

TABLE III

| Exp. No. | MM35 | MM36 | MM37 | MM38 | MM39 | MM40 | MM41 |
|---|---|---|---|---|---|---|---|
| CPC | 30 | 30 | 30 | 30 | 30 | 30 | 30 |
| EUDRAGIT L | 45 | 42.5 | 40 | 37.5 | 35 | 32.5 | 30 |
| PEG 400 | 25 | 25 | 25 | 25 | 25 | 25 | 25 |
| EUDISPERT mv | — | 2.5 | 5 | 7.5 | 10 | 12.5 | 15 |

EXAMPLE 4

Figure 4:
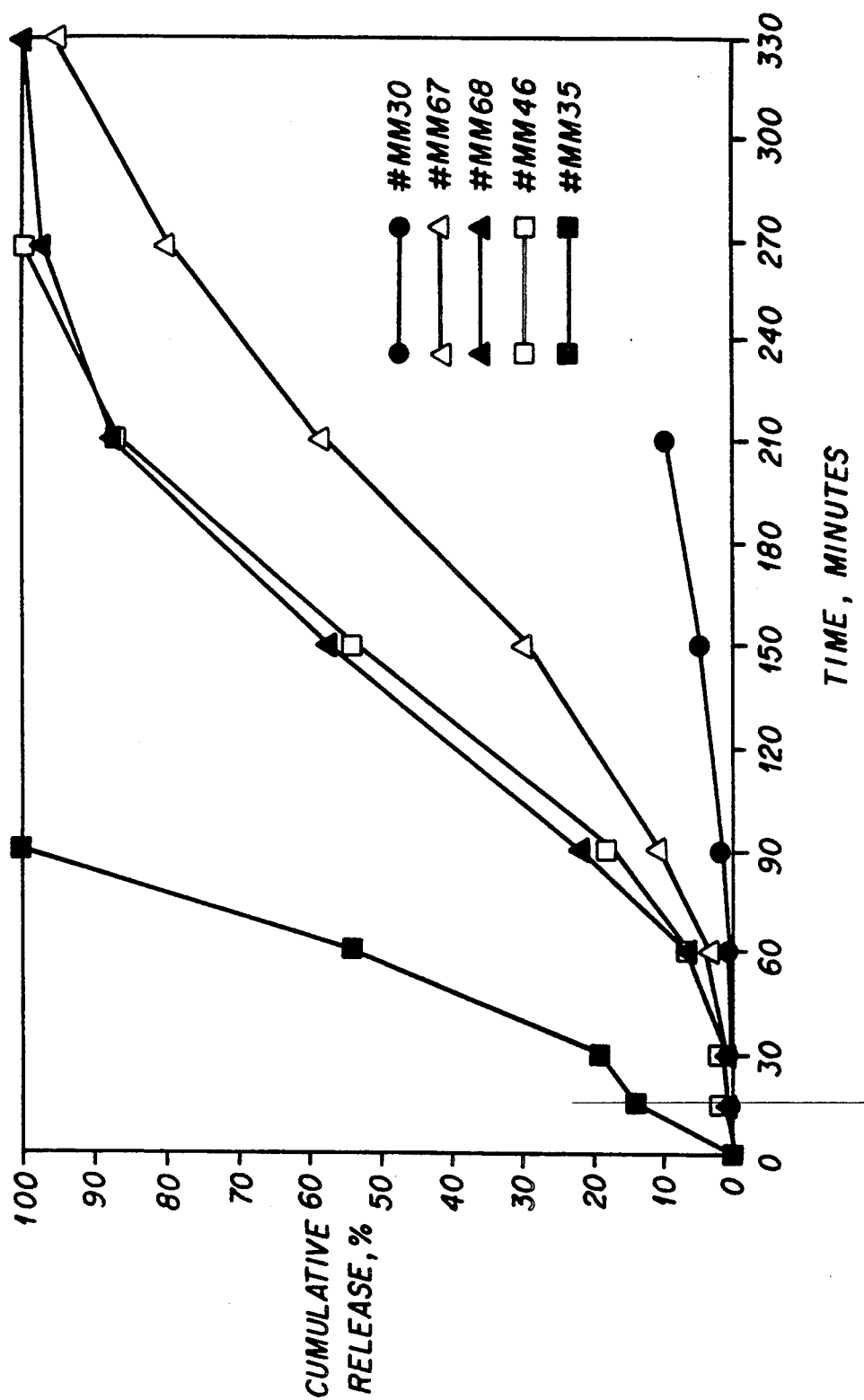
FIG. 4 shows the cumulative release percentage of CPC from the films produced by the drying of 5 liquid polymer compositions.

CPC and EUDRAGIT L preparations were made containing various PEG 400 concentrations. Table IV shows the weight percent of components in films prepared from 5 liquid polymer compositions (i.e. MM30, MM67, MM68, MM46 and MM35). The liquid compositions were dried, and the cumulative percentage of released CPC was determined. FIG. 4 shows the cumulative release percentage of CPC from the films produced by the drying of the 5 liquid polymer compositions.

TABLE IV

| Exp. No. | MM30 | MM67 | MM68 | MM46 | MM35 |
|---|---|---|---|---|---|
| CPC | 30 | 30 | 30 | 30 | 30 |
| EUDRAGIT L | 70 | 65 | 60 | 55 | 45 |
| PEG 400 | — | 5 | 10 | 15 | 25 |

EXAMPLE 5

Figure 5:
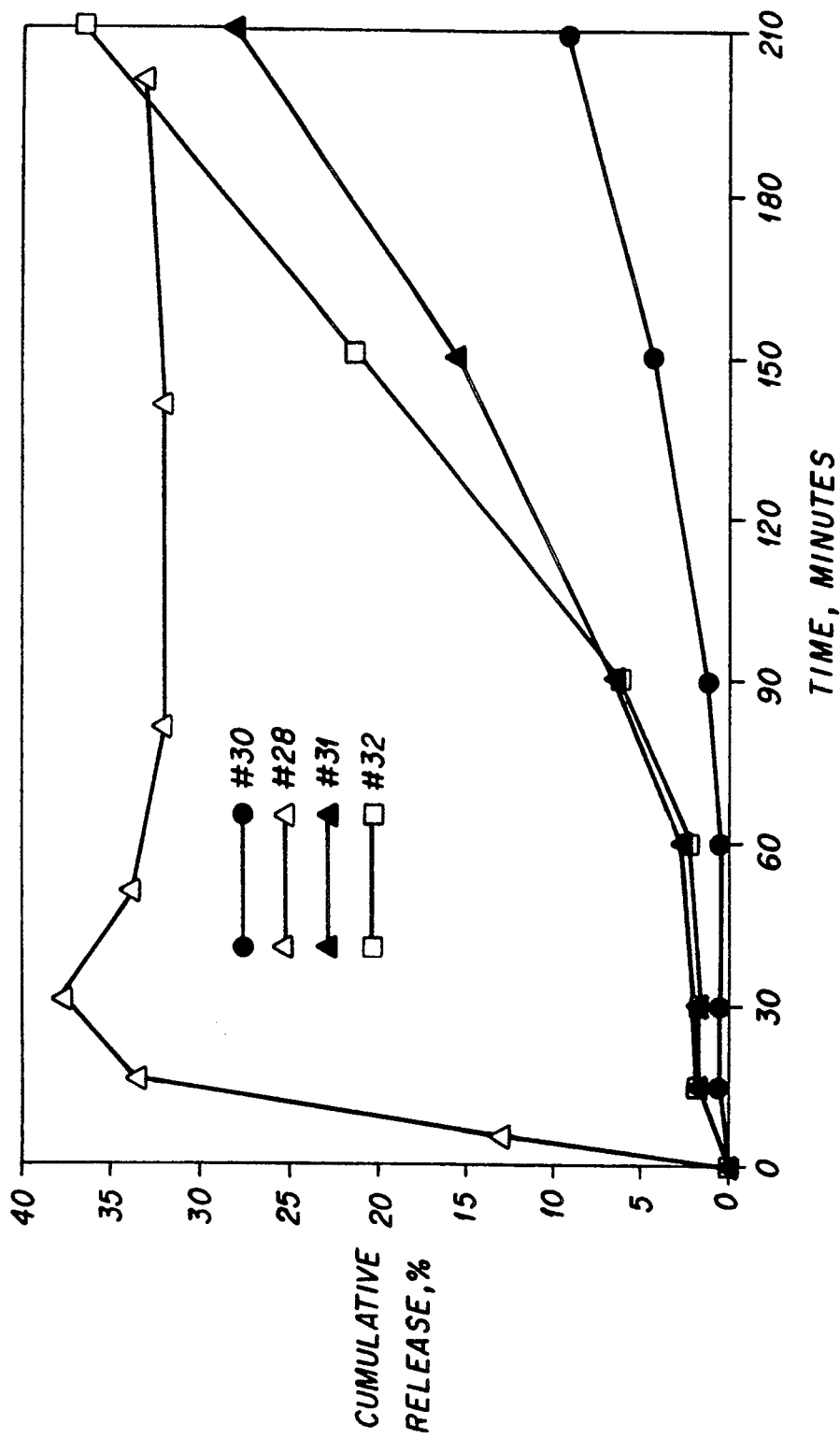
FIG. 5 shows the cumulative release percentage of CPC from the films produced by the drying of 4 liquid polymer compositions.

These experiments included an addition of various concentrations of citric acid as release enhancers. Table V shows the weight percent of components in films prepared from 4 liquid polymer compositions (i.e. MM30, MM28, MM31, and MM32). The liquid compositions were dried, and the cumulative percentage of released CPC was determined. FIG. 5 shows the cumulative release percentage of CPC from the films produced by the drying of the 4 liquid polymer compositions.

TABLE V

| Exp. No. | MM30 | MM28 | MM31 | MM32 |
|---|---|---|---|---|
| CPC | 30 | 30 | 30 | 30 |
| EUDRAGIT L | 70 | 60 | 65 | 67.5 |
| CITRIC ACID | — | 10 | 5 | 2.5 |

EXAMPLE 6

Figure 6:
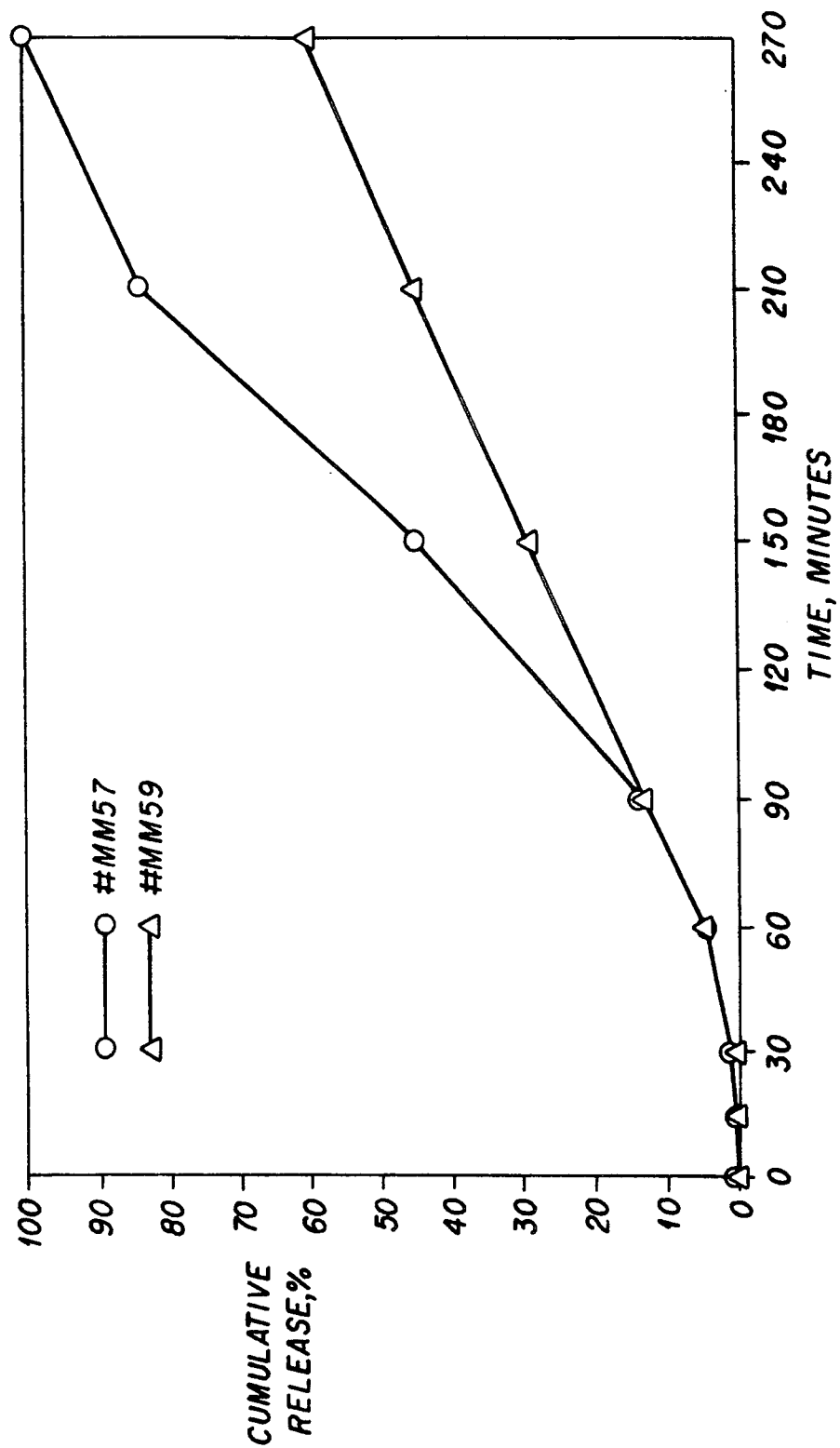
FIG. 6 shows the cumulative release percentage of CPC from the films produced by the drying of 4 liquid polymer compositions.

Two formulations containing 0.3% lysine (in film), EUDRAGIT L, and CPC were prepared. Only one was prepared with PEG 400. The ability of these preparations to mediate drug release was determined. Table VI shows the weight percent of components in films prepared from 2 liquid polymer compositions (i.e. MM57 and MM59). The liquid compositions were dried, and the cumulative percentage of released CPC was determined. FIG. 6 shows the cumulative release percentage of CPC from the films produced by the drying of the 4 liquid polymer compositions.

TABLE VI

| Exp. No. | MM57 | MM59 |
|---|---|---|
| CPC | 30 | 30 |
| EUDRAGIT L-100 | 54.7 | 69.7 |
| LYSINE HCl | 0.3 | 0.3 |
| PEG 400 | 15 | — |

Figure 7:
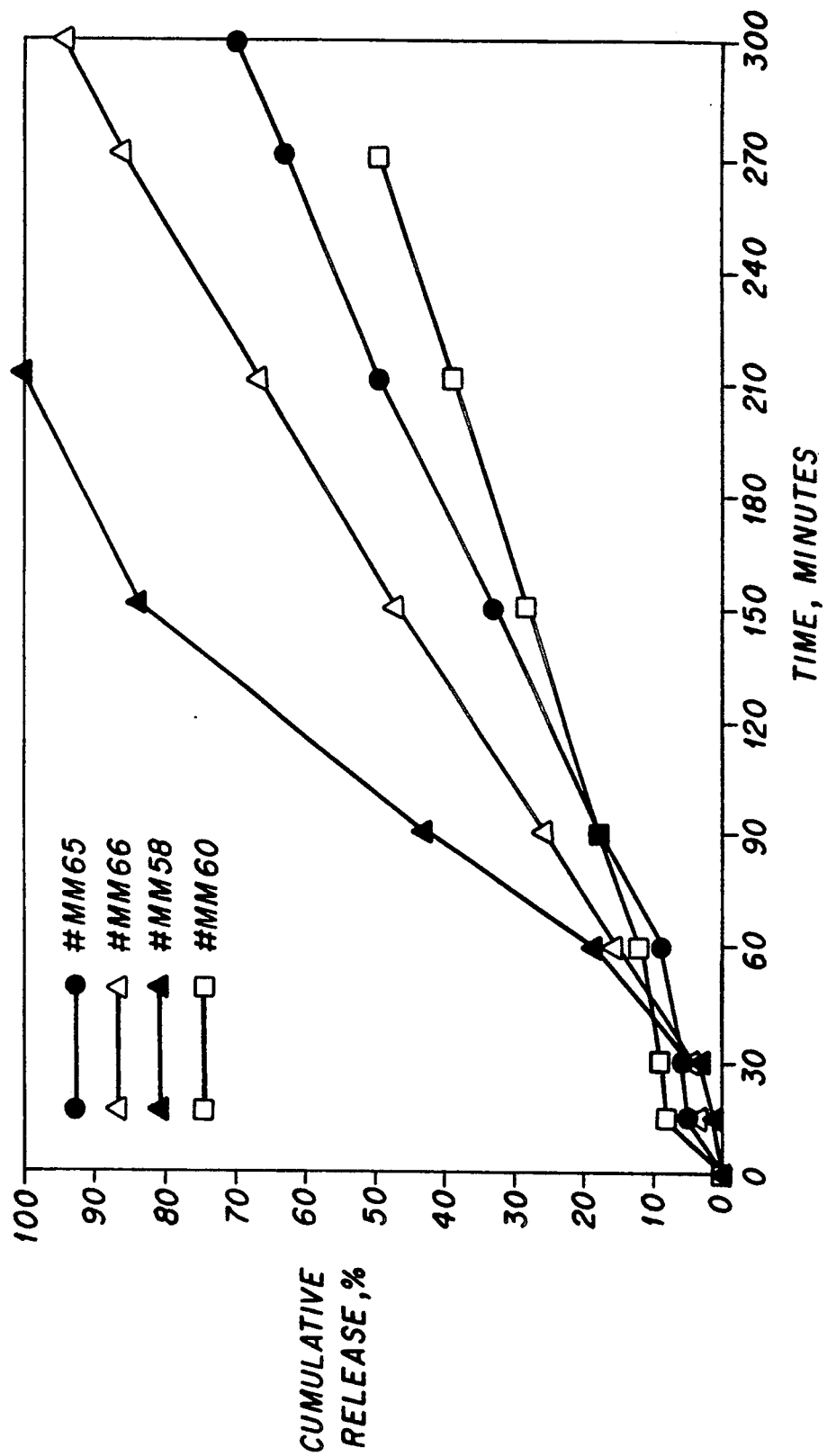
FIG. 7 shows the cumulative release percentage of CPC from the films produced by the drying of 4 liquid polymer compositions.

These formulations were prepared with 0.5% lysine (in film) EUDRAGIT L, CPC and various concentrations of PEG 400. Table VII shows the weight percent of components in films prepared from 4 liquid polymer compositions (i.e. MM60, MM65, MM66, and MM58). The liquid compositions were dried, and the cumulative percentage of released CPC was determined. FIG. 7 shows the cumulative release percentage of CPC from the films produced by the drying of the 4 liquid polymer compositions.

TABLE VII

| Exp. No. | MM60 | MM65 | MM66 | MM58 |
|---|---|---|---|---|
| CPC | 30 | 30 | 30 | 30 |
| EUDRAGIT L | 69.5 | 64.5 | 59.5 | 54.5 |
| LYSINE HCl | 0.5 | 0.5 | 0.5 | 0.5 |
| PEG 400 | — | 5 | 10 | 15 |

EXAMPLE 8

Figure 8:
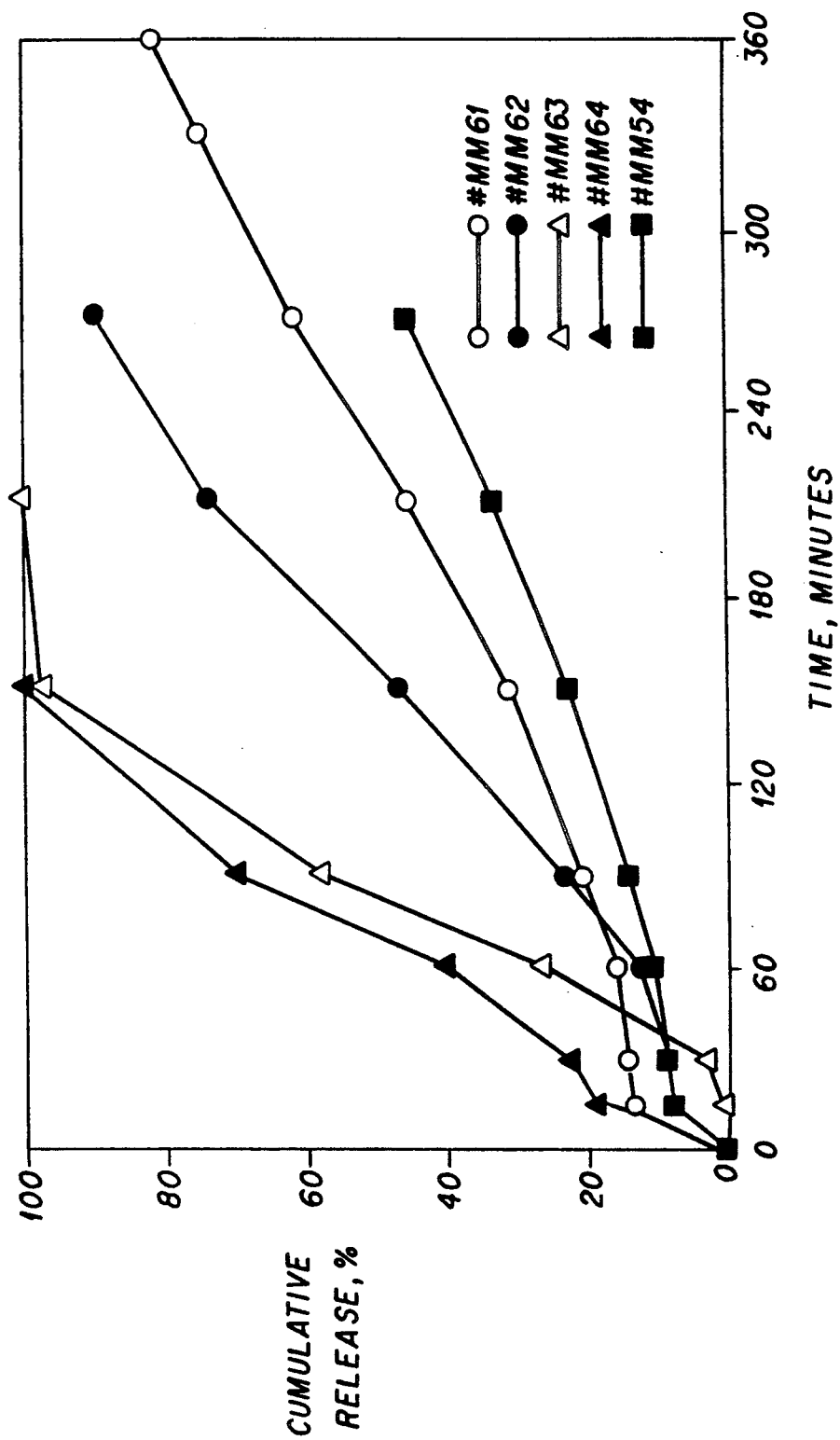
FIG. 8 shows the cumulative release percentage of CPC from the films produced by the drying of 5 liquid polymer compositions.

Formulations were prepared with 1% of lysine (in film), EUDRAGIT L, CPC and various concentrations of PEG 400. Table VIII shows the weight percent of components in films prepared from 5 liquid polymer compositions (i.e. MM54, MM61, MM62, MM63 and MM64). The liquid compositions were dried, and the cumulative percentage of released CPC was determined. FIG. 8 shows the cumulative release percentage of CPC from the films produced by the drying of the 5 liquid polymer compositions.

TABLE VIII

| Exp. No.   | MM54 | MM61 | MM62 | MM63 | MM64 |
|------------|------|------|------|------|------|
| CPC        | 30   | 30   | 30   | 30   | 30   |
| EUDRAGIT L | 69   | 64   | 59   | 54   | 49   |
| LYSINE HCl | 1    | 1    | 1    | 1    | 1    |
| PEG 400    | —    | 5    | 10   | 15   | 20   |

EXAMPLE 9

Figure 9:
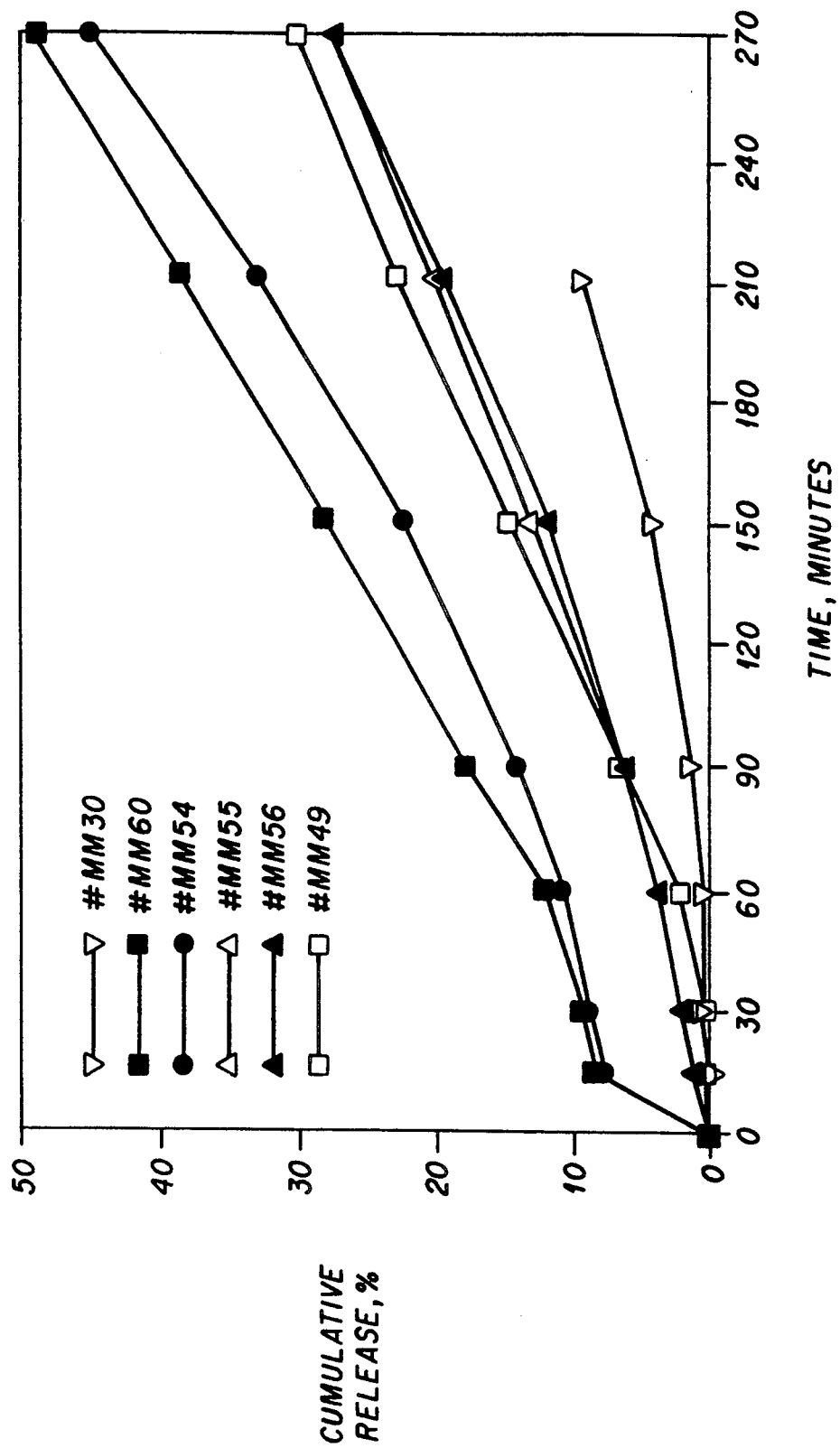
FIG. 9 shows the cumulative release percentage of CPC from the films produced by the drying of 6 liquid polymer compositions.

In these experiments, no PEG was included. They were prepared with CPC, EUDRAGIT L and various concentrations of lysine. Table IX shows the weight percent of components in films prepared from 6 liquid polymer compositions (i.e. MM30, Mm60, Mm54, MM55, Mm56 and MM49). The liquid compositions were dried, and the cumulative percentage of released CPC was determined. FIG. 9 shows the cumulative release percentage of CPC from the films produced by the drying of the 6 liquid polymer compositions.

TABLE IX

| Exp. No.   | MM30 | MM60 | MM54 | MM55 | MM56 | MM49 |
|------------|------|------|------|------|------|------|
| CPC        | 30   | 30   | 30   | 30   | 30   | 30   |
| EUDRAGIT L | 70   | 69.5 | 69   | 68   | 67   | 65   |
| LYSINE HCl | —    | 0.5  | 1    | 2    | 3    | 5    |

EXAMPLE 10

Figure 10:
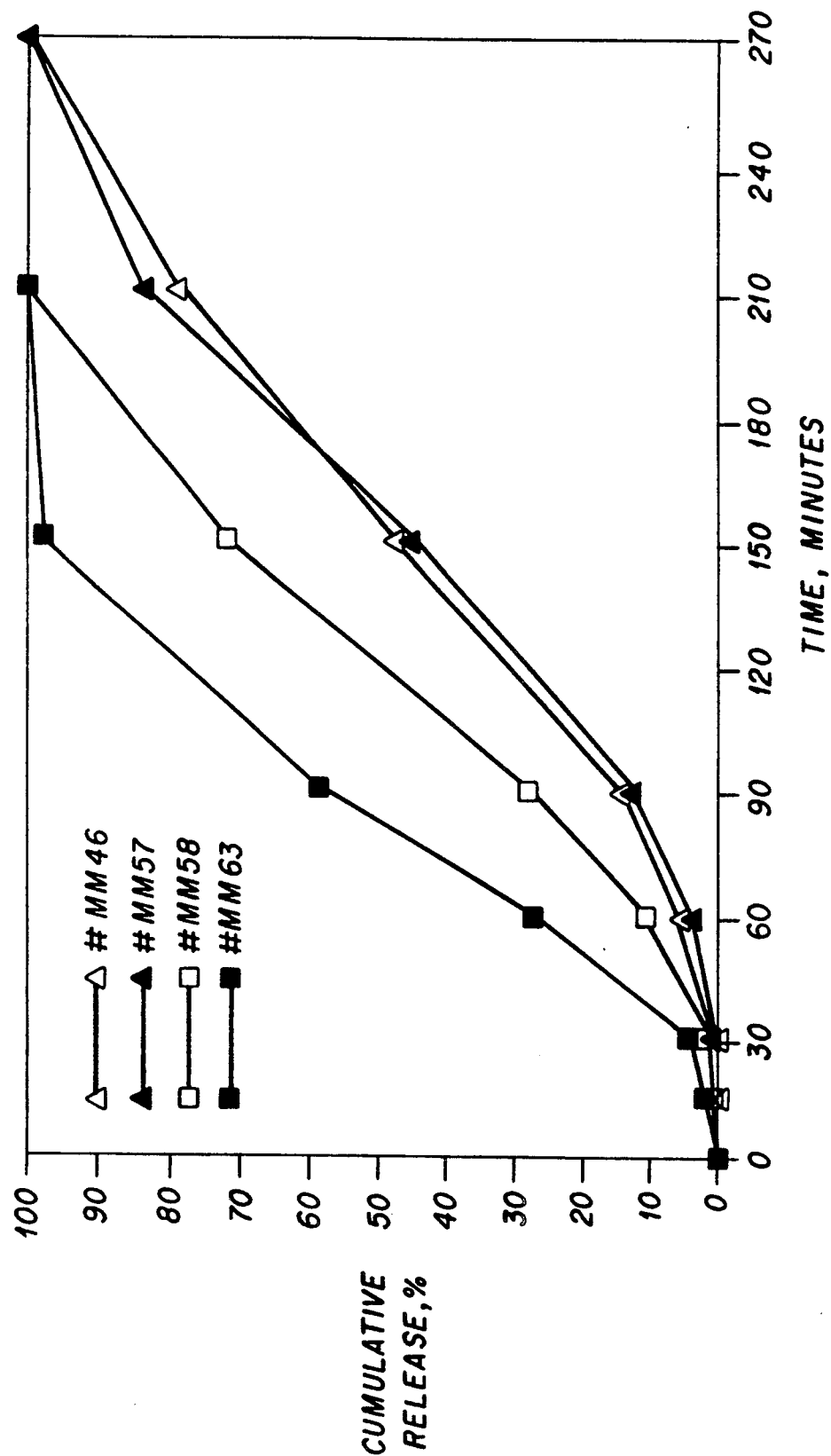
FIG. 10 shows the cumulative release percentage of CPC from the films produced by the drying of 4 liquid polymer compositions.

Formulations were prepared containing 15% PEG 400 (in film). They were prepared with CPC, EUDRAGIT L, PEG 400 and various concentrations of lysine. Table X shows the weight percent of components in films prepared from 4 liquid polymer compositions (i.e. MM46, MM57, MM58, and MM63). The liquid compositions were dried, and the cumulative percentage of released CPC was determined. FIG. 10 shows the cumulative release percentage of CPC from the films produced by the drying of the 4 liquid polymer compositions.

TABLE X

| Exp. No.   | MM46 | MM57 | MM58 | MM63 |
|------------|------|------|------|------|
| CPC        | 30   | 30   | 30   | 30   |
| EUDRAGIT L | 55   | 54.7 | 54.5 | 54   |
| PEG 400    | 15   | 15   | 15   | 15   |
| LYSINE HCl | —    | 0.3  | 0.5  | 1    |

EXAMPLE 11

Figure 11:
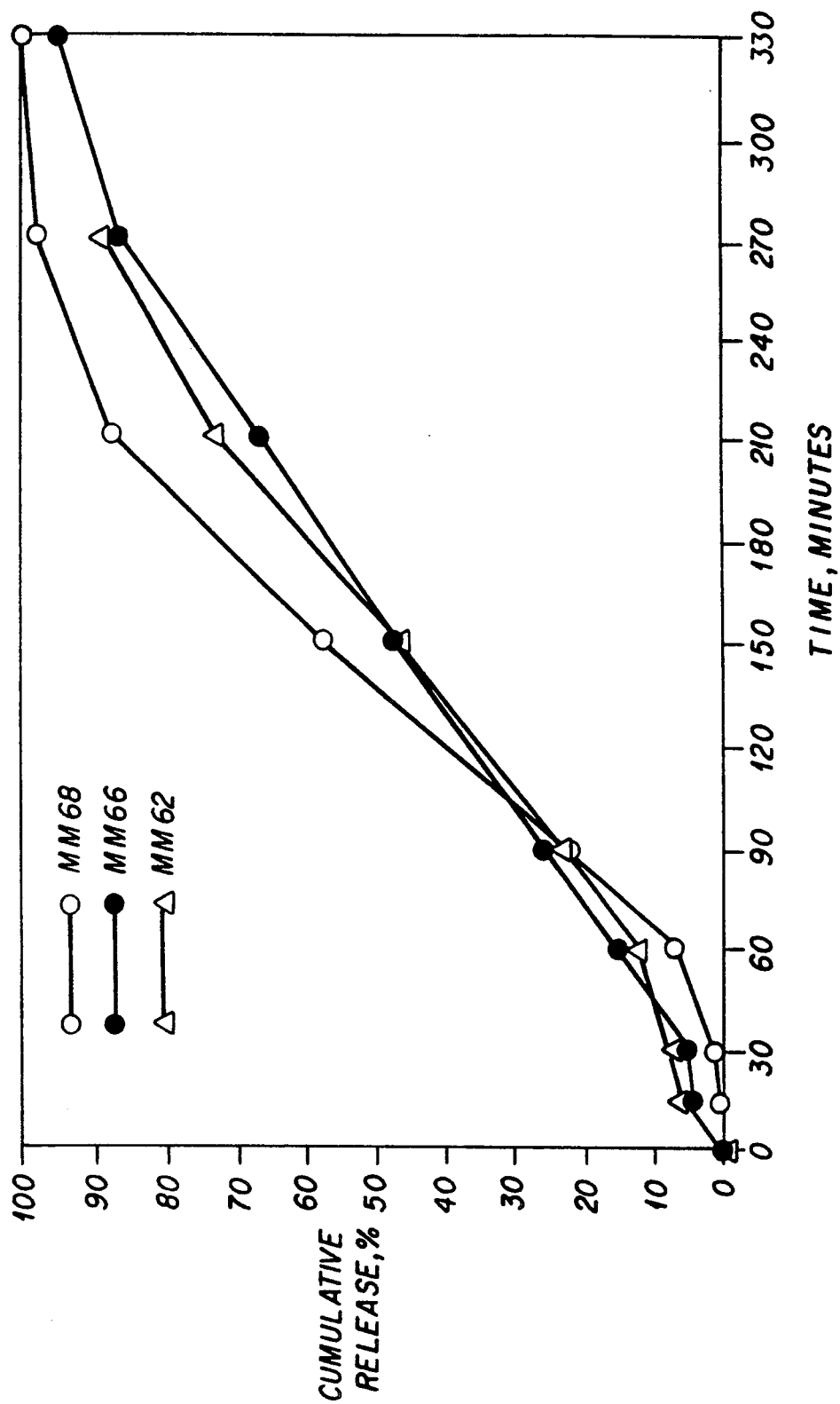
FIG. 11 shows the cumulative release percentage of CPC from the films produced by the drying of 3 liquid polymer compositions.

Formulations were prepared containing 10% PEG 400 (in film). They were prepared with CPC, EUDRAGIT L, PEG 400 and various concentrations of lysine. Table XI shows the weight percent of components in films prepared from 3 liquid polymer compositions (i.e. MM68, MM66, and MM62). The liquid compositions were dried, and the cumulative percentage of released CPC was determined. FIG. 11 shows the cumulative release percentage of CPC from the films produced by the drying of the 3 liquid polymer compositions.

TABLE XI

| Exp. No.   | MM68 | MM66 | MM62 |
|------------|------|------|------|
| CPC        | 30   | 30   | 30   |
| EUDRAGIT L | 60   | 59.5 | 59   |
| PEG 400    | 10   | 10   | 10   |
| LYSINE HCl | —    | 0.5  | 1    |

EXAMPLE 12

A summary of formulations containing various amounts of PEG 400 and lysine with their degradation times in buffer solution (0.02M, pH 6.8) was determined. Table XII shows the affect on degradation caused by altering the percent PEG 400 and % lysine components in films prepared from 14 liquid polymer compositions. The liquid compositions were dried, and the time of disappearance of the film was determined.

TABLE XII

| Exp. No. | % PEG | % lysine | Time of disappearance |
|----------|-------|----------|-----------------------|
| A. MM35  | 25    | —        | 90                    |
| MM46     | 15    | —        | 270                   |
| MM66     | 10    | —        | 300                   |
| MM67     | 5     | —        | 330                   |
| MM30     | —     | —        | >360                  |
| B. MM64  | 20    | 1        | 150                   |
| MM63     | 15    | 1        | 210                   |
| MM62     | 10    | 1        | 330                   |
| MM61     | 5     | 1        | >360                  |
| MM54     | —     | 1        | >360                  |
| C. MM58  | 15    | 0.5      | 210                   |
| MM66     | 10    | 0.5      | 330                   |
| MM65     | 5     | 0.5      | >360                  |
| MM60     | —     | 0.5      | >360                  |

EXAMPLE 13

Sustained release of CPC from film matrices was achieved with an array of formulations possessing a broad range of kinetic profiles (FIGS. 1–10). Films which were prepared with EUDRAGIT RL/RS were not homogeneously formed unless EUDISPERT mv was added. Moreover, by incorporating EUDISPERT polymer in the matrices, a partially degradable film could be achieved, however, these films released the drug within 15–20 minutes and a plateau was then observed.

FIG. 1 shows a drastic decrease in the total amount of drug released (after the short burst) when EUDISPERT concentrations increase by small increments (10%, 12.5%, and 15%). This exhibits a possible interaction between drug, EUDISPERT and EUDRAGIT RL polymers, or a presence of some sort of cross-linking which can form between the polymeric chains, resulting in drug trapping in the matrix. The use of EUDRAGIT L, which contains lower molar concentration of carboxylic acid groups than EUDISPERT, thoroughly changes the release profile of CPC (see FIGS. 1 and 2).

By adding PEG 400 to the formulations (MM50 and MM51), the difference in the release patterns were significantly diminished (FIG. 2). Films which were prepared with EUDRAGIT L were quite different in their features. FIG. 4 shows the release of CPC from EUDRAGIT L films containing elevating concentrations of PEG. In addition to the influence of PEG on the release kinetics, the disintegration time was also dependant upon its concentration as can be seen in Table XII-A. In comparison, citric acid changes the release kinetics (FIG. 5), but does not affect the solubility or the degradability of the films.

FIGS. 6-10 demonstrate the contribution of lysine hydrochloride to the release of CPC from EUDRAGIT L films. When no PEG was used in the formulations (FIG. 9), the addition of 0.5 to 5% of lysine significantly increased the rate of CPC release, but no substantive difference between the various lysine concentrations was observed. When 15% PEG 400 was added to the formulations (see FIG. 10), the rate of CPC release was also increased with the rise of lysine content from 0.5% and above. No significant change in the release kinetics was noticed in a formulation containing 0.3 of lysine. In contrast to this phenomenon, the addition of 10% PEG or less did not increase the release rate but significantly changed the kinetic profile of CPC release. As can be seen in FIG. 11, the addition of 0.5% and 1% lysine smoothed the curve and formed a constant rate of release.

The disintegration rate of CPC-EUDRAGIT L films is also affected by lysine, as is indicated in Table XII. The addition of 0.5% or 1% lysine hydrochloride to the film increased the time taken for the film to disappear by approximately 30 minutes (300 to 330 minutes and 330 to over 360 minutes). There was one exception in a formulation which contained 15% PEG, where a decrease in time was observed (270 to 210 minutes). This exception might correspond to the abovementioned phenomenon of different release kinetics between formulations containing 15% PEG and various lysine concentrations and formulations with 10% PEG and less. It is postulated that two ion-exchange mechanisms of lysine action exist in order to explain the different release patterns: 1. a delay in the polymer solubilization by cross-linking interaction, and 2. a competition of lysine with the quaternary ammonium drug on the polymer's active sites.

For anti-plaque compositions, EUDRAGIT L and RL are the preferred polymers. EUDRAGIT L is the most preferred polymer for an anti-plaque composition. EUDRAGIT L was found appropriate for the preferred mode of application. If forms a homogeneous film which can disintegrate in a few hours, releasing CPC in a sustained manner. The use of PEG, citric acid, and lysine hydrochloride aid in controlling the release of the drug. PEG, and probably citric acid as well, acts as a plasticizer within the polymeric matrix. These agents act to reduce crystallinity and increasing the accessibility to water diffusion. Citric acid, which contains three carboxylic acid salts, can act also as a drug carrier by interact with the CPC's quaternary ammonium group. This interaction, which results in a soluble complex, actually competes with a similar interaction involving the polymer and the drug. The latter interaction, however, does not result in a soluble complex and it actually causes a delay in the drug release.

Lysine, in contrast, has the ability to form cross-linking bonds between the polymer backbone chains and delay the release by reducing the polymer's permeability. In fact we found the opposite, when the release rate increased with elevation of lysine concentrations (see FIGS. 9, 10). This suggests that the cross-linking mechanism is not as dominant as another mechanism of action involving interference of drug-polymer interaction by competing on the polymer's active sites. Nevertheless, the cross-linking mechanism is postulated to occur when relatively low concentrations of PEG (10% and less) are used, forming an appropriate space for the cross interaction. As has already been noted above, the delay in the disappearance of the films which contain 10% or 5% PEG may indicate cross-linking rather than a competition mechanism.

The preferred anti-plaque composition of the present invention is formulation MM66 (FIG. 7, Table VII). This preparation contains 30% CPC, 0.5% lysine hydrochloride, 10% PEG, and 59.5% EUDRAGIT L in the dried film.

There are two advantages in using this liquid polymer preparation:
1. It releases the drug at a constant rate and in a prolonged manner,
2. It degrades or disintegrates completely (in buffer solutions) after 5.5 hours, which corresponds to overnight application.

EXAMPLE 14

Hypersensitivity of the teeth to heat, cold, sweet food or mechanical stimulation is caused by decay of the enamel or gum recession. Exposure of the dentin results in increased movement of calcium in the ion channels, which in turn causes painful stimulation of the nerve endings.

Strontium chloride has been shown to be effective in the treatment of hypersensitive teeth. It is believed to act either by entering the calcium channels and displacing calcium at the nerve endings, or by blocking the channels at the dentin surface by deposition as insoluble salts. Sensodyne toothpaste has strontium chloride as the active ingredient. Its effectiveness is limited, however, by its very short contact time, the toothpaste being washed away after a minute or two.

To overcome this limitation, a sustained-release formulation has been developed for strontium chloride by incorporating it into a biodegradable acrylic polymer. The polymer, dissolved in aqueous alcohol, is preferably "painted" on the teeth (as by soft brush, spray, etc.) to form a quickly drying film or liquid polymer. Preferably the film will release its strontium steadily over a few hours and will itself be slowly degraded overnight. The patient will thus be able to apply the film in the evening before going to sleep and by morning it will have disappeared.

Formulation of Films

Formulations were prepared in 70% alcohol by the dissolution of EUDRAGIT L and PEG 400 (where applicable) in alcohol followed by the slow addition of aqueous solutions of strontium chloride and other salts (as applicable) to the stirred mixture. 70% alcohol was chosen as the best balance between the conflicting requirements of a film that is quick-drying but does not cause undue pain upon oral application. The ratio of total film components to total solvents in the formulations was in the range of 1:3 to 1:4 (w/v), an alcoholic polymer solution of the highest workable viscosity (c.a. 0.33 g/ml) being used every time. High concentration is a necessary requirement for a quick-drying film that can be spread or painted on the teeth, but if too viscous, the components cannot be mixed in well. Formulations containing trisodium citrate were white suspensions and those without this salt were opaque solutions.

Films were prepared by spreading each formulation over a 6.5 cm diameter teflon dish and allowing to dry overnight at room temperature. The use of a weight of formulation calculated to produce approximately 0.5 g of dry film resulted in films with a mean thickness of 194μ (standard deviation 34μ).

In Vitro Release

The release of strontium from films in the mouth was simulated in vitro. A 1.5-cm square (34-44 mg) was cut and placed in 3 ml of pH 6.8 phosphate buffer (0.04M) in a thermostatically controlled water bath at 37° C. with gentle shaking. At suitable intervals until the film had totally dissolved, the film was transferred to a fresh vial containing another 3 ml of buffer. This crudely simulated the continuous renewal of saliva in the mouth and also enabled the amount of strontium released at each time interval to be measured. The film was also weighed at hourly intervals to obtain an indication of its disintegration profile. More frequent weighings were precluded by the need to dry the film in air for at least 5 minutes before weighing.

Release of strontium and disintegration of the film are expected to be slower in vivo than in this model because of the very limited movement of saliva in the mouth during sleep. We therefore aimed for a film that would release strontium steadily over 1-2 hours and disintegrate in 2-4 hours under these experimental conditions.

Analysis for Strontium

The samples of buffer from the release experiments were analyzed for strontium content by atomic absorption with an air-acetylene flame and detection of the 460.7 nm line. Standard solutions of strontium chloride in the buffer were used to construct a calibration curve, which was found to be linear in the range of 0.5-8 μg/ml of strontium, and the samples were further diluted in the release buffer accordingly. From the weights of wet formulation on the plate, dry film, and film square, the weight of strontium in the film square could be calculated, and thus the concentrations of strontium in the samples were translated into percent strontium released. As the total calculated recovery of strontium from the films generally differed somewhat from 100%, the results were normalized to 100% total release, the films having been totally degraded.

To ensure that no other component of the films absorbed at the strontium absorption wavelength, a number of blank formulations without strontium were prepared in parallel with the strontium formulations and films were made in an identical manner. Then for the in vitro release experiments, parallel experiments on squares of the blank films were carried out as well and the samples read by atomic absorption after dilutions similar to those of the positive samples. The readings were zero in every instance, and after a number of such experiments, the preparation of blank films was discontinued.

EXAMPLE 15

The strontium-release and degradation profiles for the array of formulations tested are shown graphically in FIGS. 12-18. Accompanying each figure or pair of figures is a table (below) detailing the composition of the relevant films, expressed as weight percent of the components. It should be noted that these values include water of crystallization of hydrated salts, which was found to be retained in the fried films. In fact, the films contained 0-10% additional entrapped water, as revealed by their dry weights which were generally slightly higher than calculated from the weights of the components. This additional water has not been taken into account for the composition data.

Figure 12:
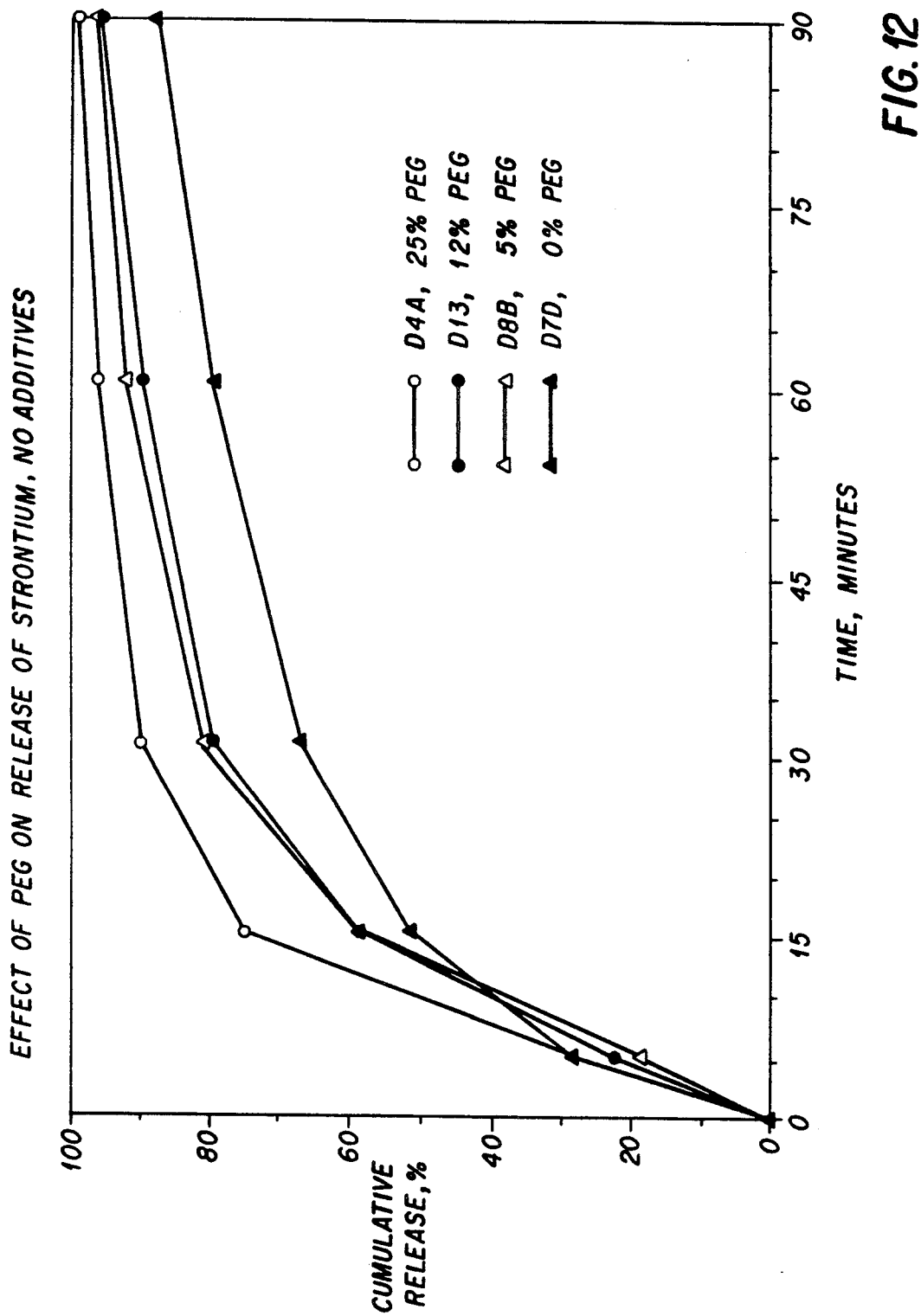
FIG. 12 shows the effect of polyethylene glycol ("PEG") on the release of strontium chloride from a film produced by the drying of a liquid polymer composition.
Figure 13:
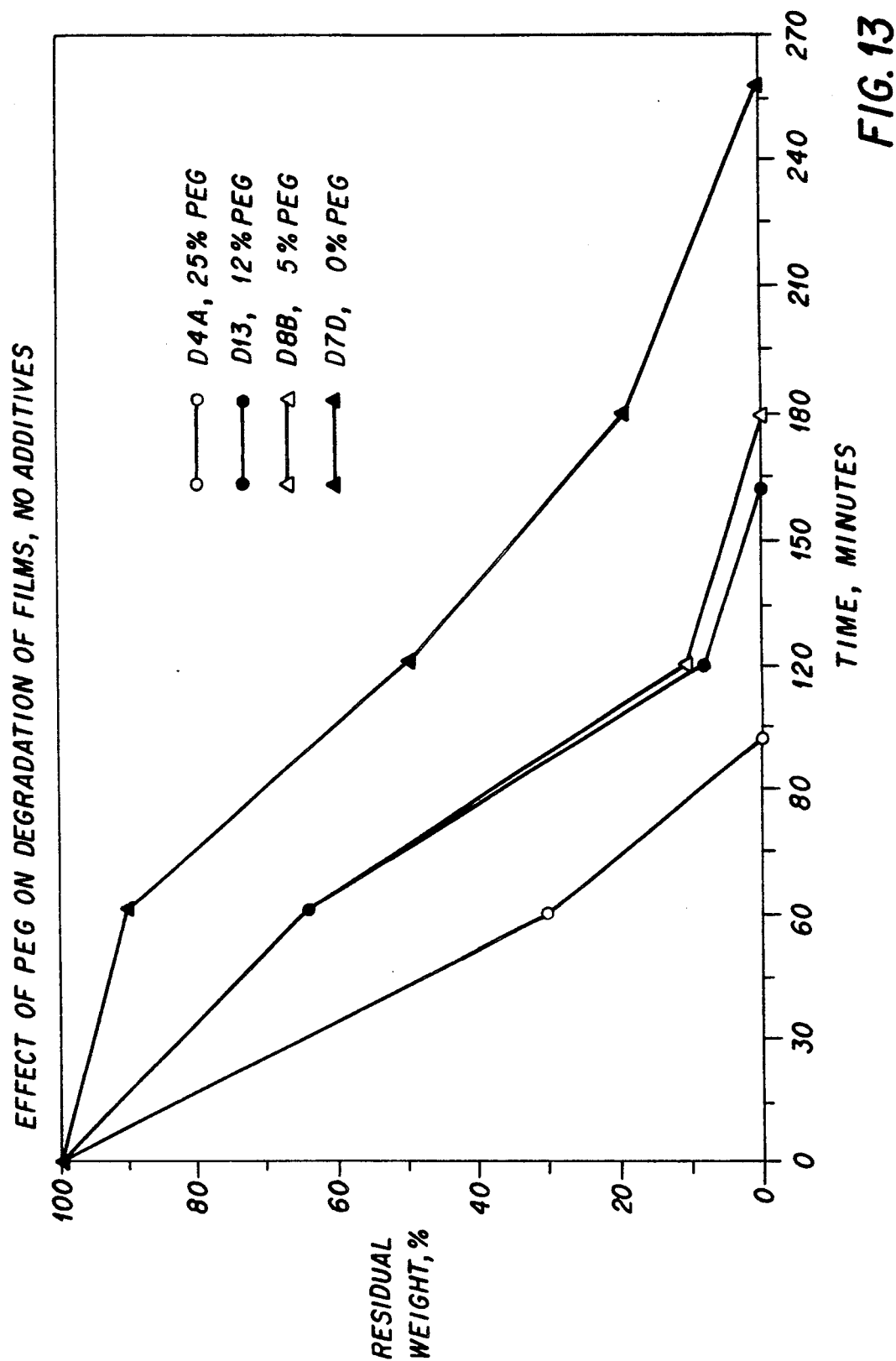
FIG. 13 shows the effect of polyethylene glycol ("PEG") on the degradation of 4 films produced by the drying of a liquid polymer composition.

Films containing only the polymer, strontium chloride and various concentrations of PEG 400 released 50-70% of the strontium in the first 15 minutes (FIG. 12) while it took between 1.5 and 4 hours for the films to be totally degraded (FIG. 13). The composition of these films is shown in Table XIII.

TABLE XIII

| Component | Weight % of Components of Film | | | |
|---|---|---|---|---|
| | D4A | D13 | D8B | D7D |
| Strontium Chloride Hexahydrate | 10 | 10 | 10 | 10 |
| EUDRAGIT L | 65 | 78 | 85 | 90 |
| PEG 400 | 25 | 12 | 5 | — |
| Trisodium Citrate Dihydrate | — | — | — | — |
| Calcium Chloride Dihydrate | — | — | — | — |

The different time scales of the two graphs should be noted. The rates of both strontium release and degradation increase with increasing concentrations of the plasticizer.

Figure 14:
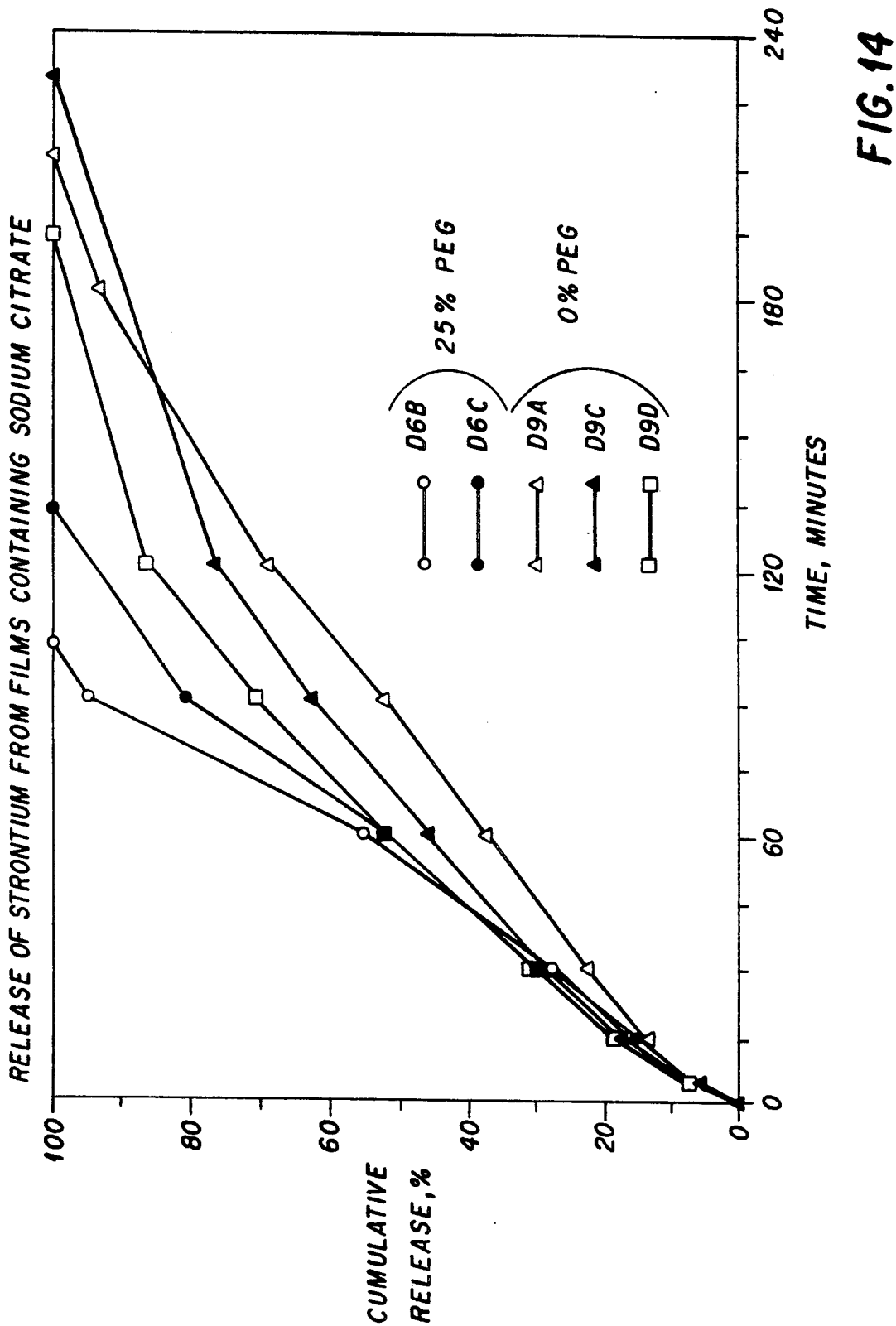
FIG. 14 shows the effect of trisodium citrate on the ability of a film to release strontium.

The addition of 7.4% trisodium citrate to the films dramatically reduced the rate of strontium release (FIG. 14). The composition of these films is shown in Table XIV.

TABLE XIV

| Component | Weight % of Components of Film | |
|---|---|---|
| | D6C | D9C |
| Strontium Chloride Hexahydrate | 10 | 10 |
| EUDRAGIT L | 57.6 | 82.6 |
| PEG 400 | 25 | — |
| Trisodium Citrate Dihydrate | 7.4 | 7.4 |
| Calcium Chloride Dihydrate | — | — |

Almost linear, zero-order kinetics prevail with only 13-19% release in the first 15 minutes. FIG. 14 also illustrates the range of results from replicate in vitro release experiments. Both replicate squares from the same film and squares from replicate films were tested, and replicates were neither prepared nor tested on the same day.

Figure 15:
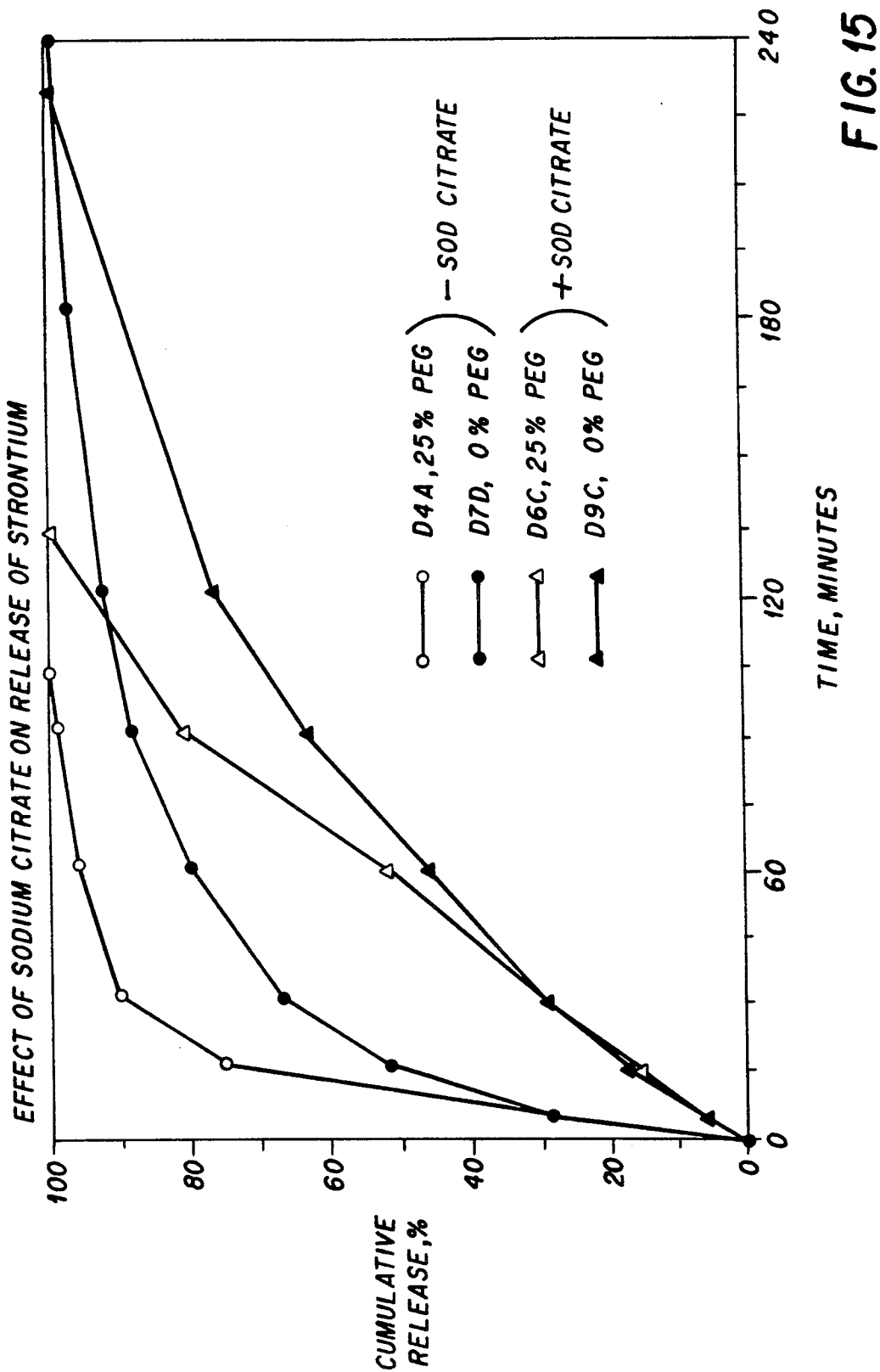
FIG. 15 highlights the effect of the addition of trisodium citrate and also shows that the inclusion of PEG increased the rate of strontium release from citrate-containing films as it did for films without citrate.
Figure 16:
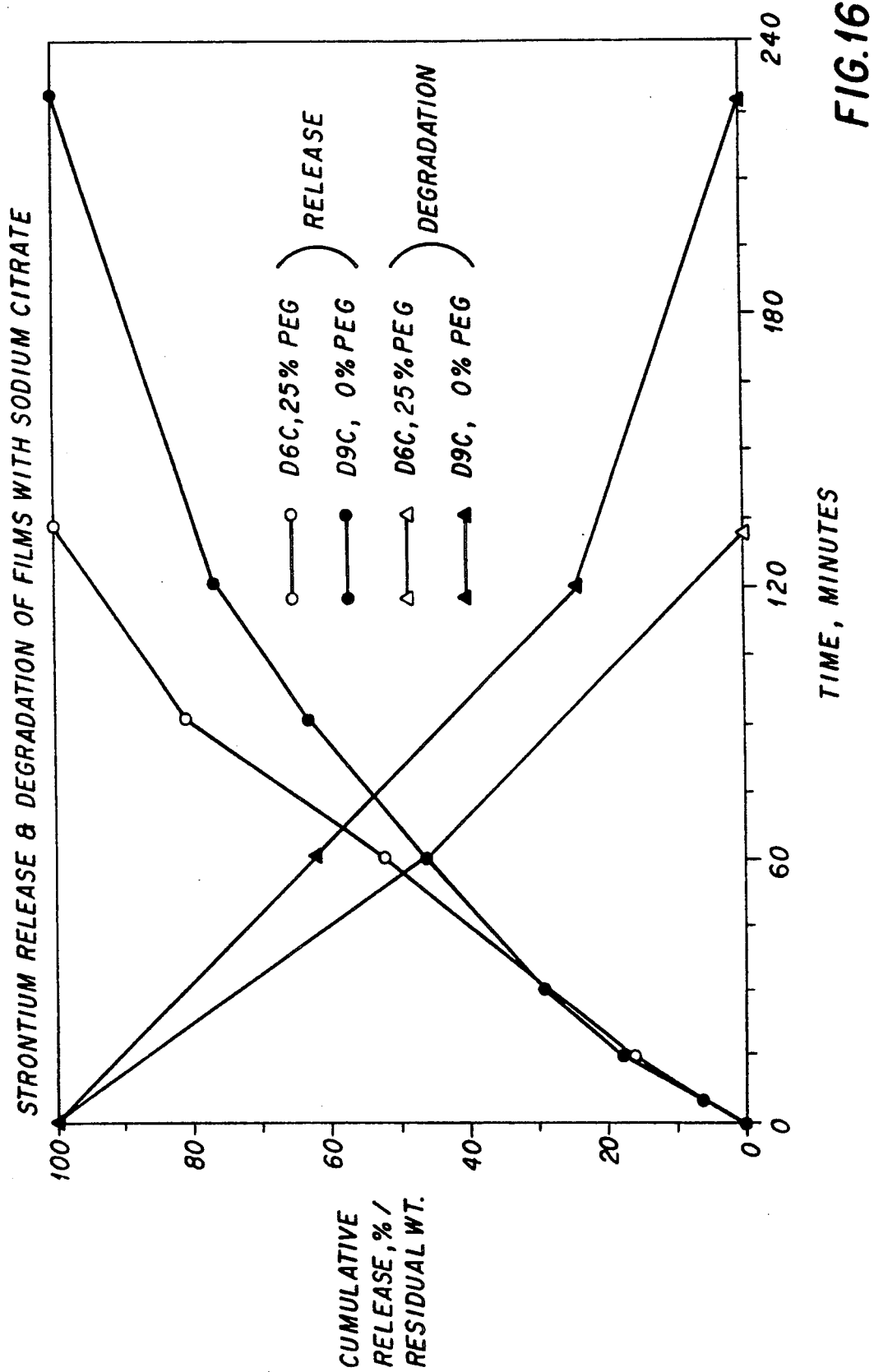
FIG. 16 shows that the degradation rate of a film was increased by PEG, but appeared to be unaffected by trisodium citrate.

FIG. 15 highlights the effect of the addition of trisodium citrate and also shows that the inclusion of PEG increased the rate of strontium release from citrate-containing films as it did for films without citrate. The degradation rate was similarly increased by PEG (FIG. 16), but appeared to be unaffected by trisodium citrate. The composition of these films is shown in Table XV.

TABLE XV

| Component | Weight % of Components of Film | | | |
|---|---|---|---|---|
| | D4A | D7D | D6C | D9C |
| Strontium Chloride Hexahydrate | 10 | 10 | 10 | 10 |
| EUDRAGIT L | 65 | 90 | 57.6 | 82.6 |
| PEG 400 | 25 | — | 25 | — |
| Trisodium Citrate Dihydrate | — | — | 7.4 | 7.4 |
| Calcium Chloride | — | — | — | — |

TABLE XV-continued

| Component | Weight % of Components of Film | | | |
|---|---|---|---|---|
| | D4A | D7D | D6C | D9C |
| Dihydrate | | | | |

The symmetry between the release and degradation profiles of films with trisodium citrate (FIG. 16) indicates that the strontium was released steadily over the entire period of degradation of these films, quite different from the behavior of films without citrate (FIGS. 12 and 13).

Figure 17:
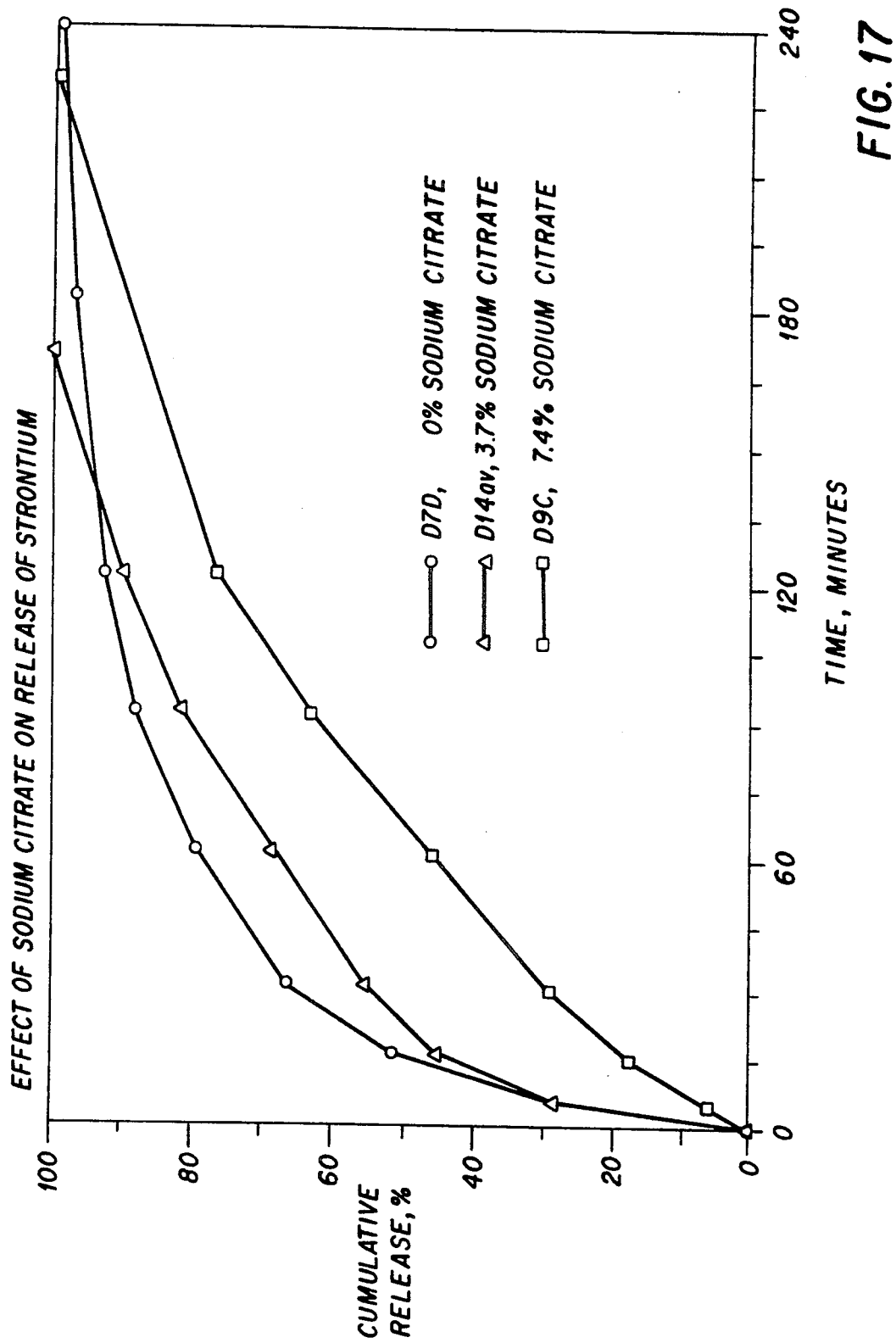
FIG. 17 shows the effect of the concentration of trisodium citrate in a film on the strontium release profile.
Figure 18:
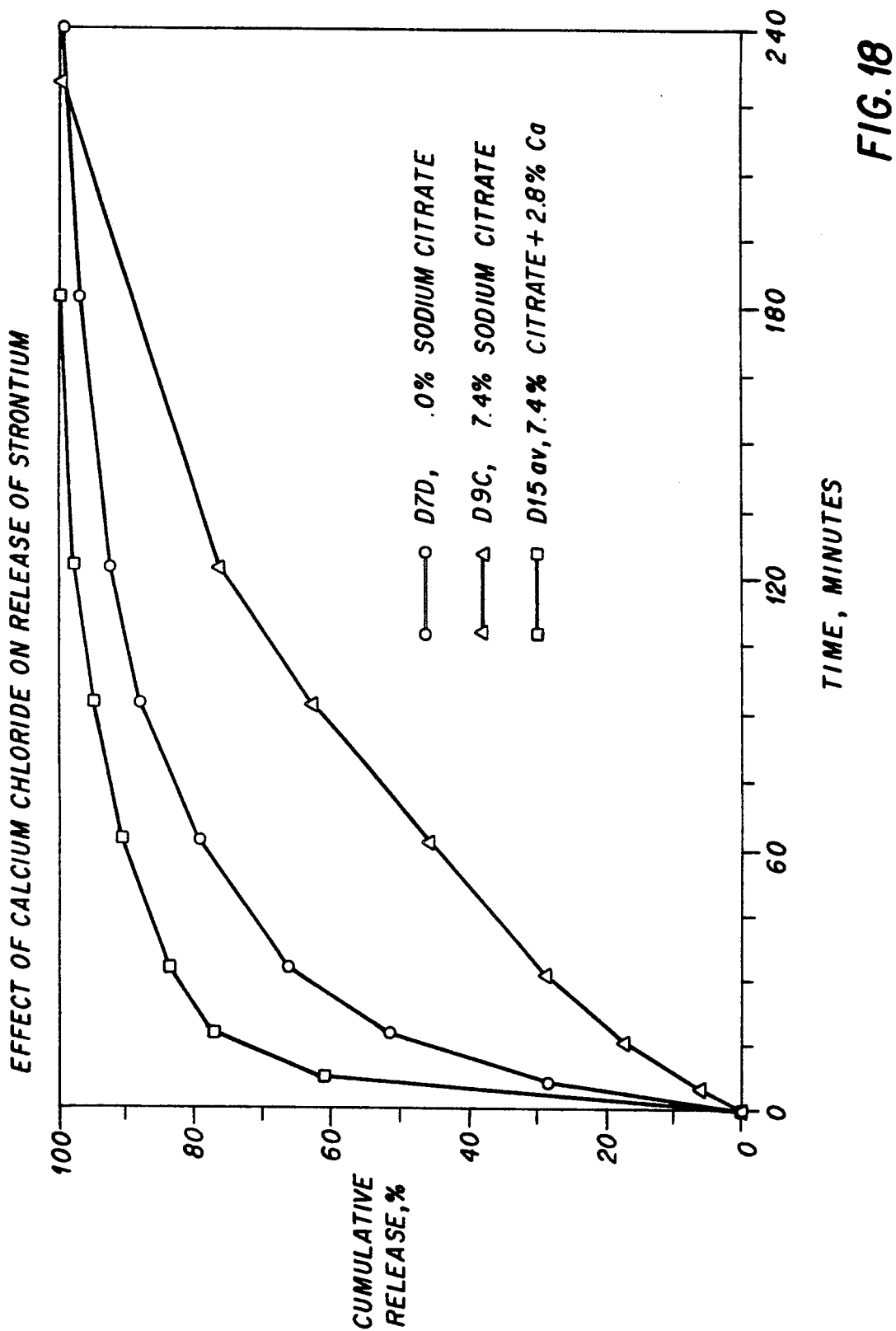
FIG. 18 shows the effect of the concentration of trisodium citrate in a film which additionally contains calcium chloride on the strontium release profile.

When the concentration of trisodium citrate in the film was reduced to half, a strontium release profile of intermediate rate was obtained (FIG. 17). The opposite effect was displayed by a formulation containing calcium chloride in addition to trisodium citrate. The initial release rate was even faster than films without additives, reaching 60% in the first 5 minutes (FIG. 18). No effect on the degradation profile was observed for either additive. The composition of these films is shown in Table XVI.

TABLE XVI

| Component | Weight % of Components of Film | | | |
|---|---|---|---|---|
| | D7D | D14av | D9C | D15av |
| Strontium Chloride Hexahydrate | 10 | 10 | 10 | 10 |
| EUDRAGIT L | 90 | 86.3 | 82.6 | 79.8 |
| PEG 400 | — | — | — | — |
| Trisodium Citrate Dihydrate | — | 3.7 | 7.4 | 7.4 |
| Calcium Chloride Dihydrate | — | — | — | 2.8 |

EXAMPLE 16

The introduction of strontium chloride into a matrix of EUDRAGIT L without additives imparts a limited measure of sustained release. Initial release is rapid, however, and appears to be diffusion controlled, being much faster than the dissolution of the polymer. This increased rates of release and degradation when polyethylene glycol is added to the formulation are possibly due to its action as a plasticizer, increasing the separation between layers of the polymer and thus allowing easier penetration of the buffer.

A different mechanism may be responsible for the zero order release kinetics observed in the presence of 7.4% trisodium citrate. At this concentration the divalent strontium ions in the formulation are exactly balanced by two equivalents of carboxyl groups, and indeed, the appearance of a voluminous precipitate in the formulation on addition of the citrate implicates the formation of strontium citrate (or more precisely tristrontium dicitrate), which is only slightly soluble. Being a larger molecule than strontium chloride, strontium citrate may be effectively entrapped within the polymer and its low solubility may further limit its ability to diffuse out until the polymer surrounding it dissolves. An alternative explanation is that the divalent strontium ions are linked on one side to citrate carboxyl groups and on the other side to carboxyl groups of the polymer and as such can only enter solution together with the polymer.

The difference between the mechanisms of strontium release with and without sodium citrate was further highlighted by in vitro release experiments done in pure water, which does not dissolve the polymer. Without sodium citrate a release profile similar to that in buffer was observed. In the presence of sodium citrate, however, 12% of the strontium in the film square was released within the first half hour and only a further 1% subsequently; the remaining 87% was not released at all. The small proportion released was either non-entrapped strontium on the surface of the film of free strontium not bound to the polymer. Hence, the rates of release and degradation of films containing 7.4% sodium citrate may be similar (FIG. 16) because the former is dependent on the latter and is controlled by it.

If strontium is bound to the polymer in the film, the possibility was considered that it remains bound after dissolution of the polymer and as such would not be effective for the treatment of hypersensitive teeth. This was discounted by dialysis of dissolved citrate-containing films against the same buffer. After 48 hours and one change of buffer, atomic absorption revealed only 0.1% of the strontium remaining in the polymer solutions. Thus even if the strontium is bound to the polymer in the dry film, it is released as free ionic strontium and ought to be therapeutically effective.

The addition of 2.8% calcium chloride, half the molar quantity of the strontium chloride, to citrate-containing films was expected to increase the release rate by competition with strontium for the available citrate, giving a release profile similar to that from the film with half the quantity of sodium citrate (FIG. 17). The result, however, was surprising (FIG. 18). Calcium appears to expel strontium from citrate-containing films at a rate faster even than the release of strontium from films containing no citrate or calcium.

In conclusion, the film D9 (containing strontium chloride hexahydrate, EUDRAGIT L, and trisodium citrate dehydrate) is the preferred anti-hypersensitivity composition of the present invention, releasing strontium and being degraded steadily over 3-4 hours. Although this formulation contains a precipitate, it settles only slightly over a period of a few days. If a slightly faster initial release is desired, the amount of trisodium citrate can be reduced (as in film D14), or if the degradation in vivo is found to be too prolonged, polyethylene glycol may be added (as in film D6). The precipitates in D6 and D14 settled within one day, but it should be possible to prolong settling by an increase in the viscosity of the formulation (reduction of the solvent volume) or by the addition of a suitable detergent.

EXAMPLE 17

Potassium ion has been used in a variety of dentifrice formulations designated to treat dentin hypersensitivity. The compositions of two anti-hypersensitivity compositions are shown in Table XVII. Composition 1 contains a plasticizer which also acts as an ionic surfactant forming a homogeneous potassium phase. Composition 2 contains an ion-pair agent, which is a relatively water insoluble substance.

TABLE XVII

| | Composition (% w/w) | |
|---|---|---|
| | 1 | 2 |
| Potassium Chloride | 2.25 | — |
| Potassium Hydrogen Tartrate | — | 4.5 |
| Methacrylic acid copolymer | 18.02 | 18.02 |
| Sodium docusate | 2.25 | — |
| Alcohol | 50.45 | 50.45 |
| Water | 27.03 | 27.03 |

EXAMPLE 18

The ability of the anti-plaque liquid polymer of the present invention to prevent or attenuate the accumulation of plaque on tooth surfaces was evaluated using 50 human volunteers. The teeth of the volunteers were cleaned (by scaling) to remove accumulated plaque. The volunteers were then divided into two groups. One group received daily treatment with formula MM66 CPC-containing, anti-plaque liquid polymer (discussed in Example 13); the other group received daily treatment with a placebo. At various times after the scaling, the teeth of the volunteers were examined and the plaque indices (PI) of the tooth surface were ascertained. A low PI value indicates less plaque accumulation than a higher PI value. The results of this experiment are shown in Table XVIII.

TABLE XVIII

| Time in Days | Percent of Tooth Surface[1] Scored as: | | | |
|---|---|---|---|---|
| | PI = 0 | | PI = 3 | |
| | Active | Placebo | Active | Placebo |
| 0[2] | 12.1 | 10.6 | 31.4 | 27.3 |
| 8 | 38.7 | 27.0 | 6.8 | 6.4 |
| 22 | 45.2 | 22.2 | 11.4 | 17.6 |
| 26 | 49.3 | 32.1 | 6.2 | 13.1 |

[1] Distal, mesial, buccal, lingual, and palatial surfaces on the anterior teeth were scored.
[2] Day of scaling; PI determined prior to scaling

EXAMPLE 19

Formulations of liquid polymer compositions were prepared for various uses. The formulations are the preferred compositions for the respective uses. Values are presented in percent weight by weight (% w/w).

| A. LIQUID POLYMER COMPOSITION FOR DENTURE STOMATITIS | |
|---|---|
| Methacrylic acid copolymer type A | 10.0 |
| Methacrylic acid copolymer type A | 9.0 |
| Nystatin | 2.4 |
| Polyethylene glycol 400 | 2.4 |
| Ethyl alcohol | 76.2 |
| B. LIQUID POLYMER COMPOSITION FOR ORAL CANDIDIASIS | |
| Methacrylic acid copolymer type A | 19.0 |
| Polyethylene glycol 400 | 2.4 |
| Amphotericin B | 2.4 |
| Ethyl alcohol | 76.2 |
| C. LIQUID POLYMER COMPOSITION FOR ROOT CANAL STERILIZATION | |
| Methacrylic acid copolymer type A | 6.9 |
| Chlorhexidine digluconate (20% aqueous solution) | 22.9 |
| Polyethylene glycol 400 | 11.5 |
| Ethyl alcohol | 58.7 |
| D. LIQUID POLYMER COMPOSITION FOR APHTHOUS ULCERS AND FOOD (i.e. PIZZA) BURNS | |
| Methacrylic acid copolymer type A | 20.0 |
| Sodium saccharin | 0.1 |
| Polyethylene glycol 400 | 2.2 |
| Ethyl alcohol | 58.7 |
| Purified water | 19.0 |
| E. LIQUID POLYMER COMPOSITION FOR APHTHOUS ULCERS | |
| Methacrylic acid copolymer type A | 21.9 |
| Cetylpyridinium chloride | 11.0 |
| Lysine hydrochloride | 0.2 |
| Sodium saccharin | 0.1 |
| Polyethylene glycol 400 | 3.7 |
| Ethyl alcohol | 43.6 |
| Purified water | 19.5 |
| F. LIQUID POLYMER COMPOSITION FOR | |
| WISDOM TOOTH EXTRACTION | |
| Methacrylic acid copolymer type B | 15.1 |
| Chlorhexidine digluconate (20% aqueous solution) | 23.3 |
| Glycine | 0.1 |
| Polyethylene glycol 400 | 2.2 |
| Sodium saccharin | 0.1 |
| Ethyl alcohol | 58.7 |
| Purified water | 0.5 |

EXAMPLE 20

Sustained Release of Camphorated p-Chlorophenol For Root Canal Sterilization

Experimental Method—Basic Components

Camphor (BP)—Merck
Chlorophenol (AR)—Fluka
EUDRAGIT S (Methacrylic acid copolymer, type B)—Roehm Pharma
Ethyl cellulose N100 (NF)—Hercules
Ethanol (USP)—Bio Lab
Absorbent points—Dentsply Methods 1. Preparation of Camphorated p-Chlorophenol (CPK)

6.5 g camphor and 3.5 g chlorophenol were mixed together in a mortar and crushed with a pestle until all the solids were liquified.

2. CPK Liquid Polymer Preparation—General Description

The formulations were all prepared by the same general procedure described as follows: camphorated p-chlorophenol was dissolved in ethanol and EUDRAGIT S was added slowly while stirring until all the polymer dissolved. Additional components were added while stirring continuously.

3. Release of p-chlorophenol

NOTE: Since p-chlorophenol is the active antibacterial agent in CPK, it was chosen to be the release marker in this system.

The release of chlorophenol was measured from film, coated absorbent points, and coated paper tissues (Kimwipes brand).

A. Film 3 g of the formulation was poured onto a teflon plate. The film was generated after allowing the solvent to evaporate for 5 hours. The film was cut and accurately weighed.

B. Coated absorbent points

An absorbent point was placed in the liquid polymer solution for 2 sec and allowed to dry. The amount of coating added to the absorbent point was accurately weighed.

C. Coated paper tissues

A paper tissue was placed in the liquid polymer solution and allowed to dry. It was then cut into pieces and accurately weighed.

The film, coated absorbent point and/or coated paper tissue were then placed in vials containing 5 ml phosphate buffer (0.02M, pH 6.8) and incubated at 37° C. They were then transferred at specific time intervals to other vials containing buffer solution. The concentration of p-chlorophenol released was determined by a UV spectrophotometer (UVIKON 930, Kontron Instruments) at 223.2 nm against a standard calibration curve.

4. Microbiological Testing

Two absorbent points were placed in the liquid polymer solution for 2 sec and allowed to dry. The amount of film absorbed by the absorbent points was accurately weighed. The absorbent points were placed in vials containing 1 ml sterile phosphate buffer (0.02M, pH 6.8) each and incubated at 37° C. They were then transferred after 0.5, 1, 2, 5, 24 and 48 hours to other vials containing buffer solution. 0.2 ml was taken at each stage for determination of chlorophenol concentration by HPLC against a standard calibration curve, and 0.8 ml was transferred to the microbiology lab for bacteriological testing.

A. Materials and Methods

Bacterial strain—Streptococcus mutans 1895 was studied.

Growth conditions—The test organism was grown aerobically at 37° C. overnight in Brain Heart Infusion broth (BHI, Difco, Detroit, Mich.) and then diluted with BHI to contain approximately $10^3$ colony-forming units (CFU) per ml.

Susceptibility test—The test was performed in test tubes, according to the broth dilution method. The volume of 0.8 ml of each tested solution was added to 1 ml of BHI. One (1) ml of the inoculum was added to each test tube. After 24 h of aerobic incubation at 37° C. the optical density was measured against BHI at 540 nm, in a Klett instrument.

Results

1. The Effect of Polymer and Plasticizer on the Release Profile from Film and a Coated Absorbent Point The release of p-chlorophenol from film matrices and absorbent points coated with CPK was tested with a variety of formulations (Table XIX). No film was formed from formulation RK25.1, and very soft films were formed from other formulations containing polyethylene glycol 400 (PEG 400) (RK25.2-4). In general the release profiles reveal a burst effect (extreme or moderate depending on the formulation) followed by very slow release over an extended period of time.

Figure 19:
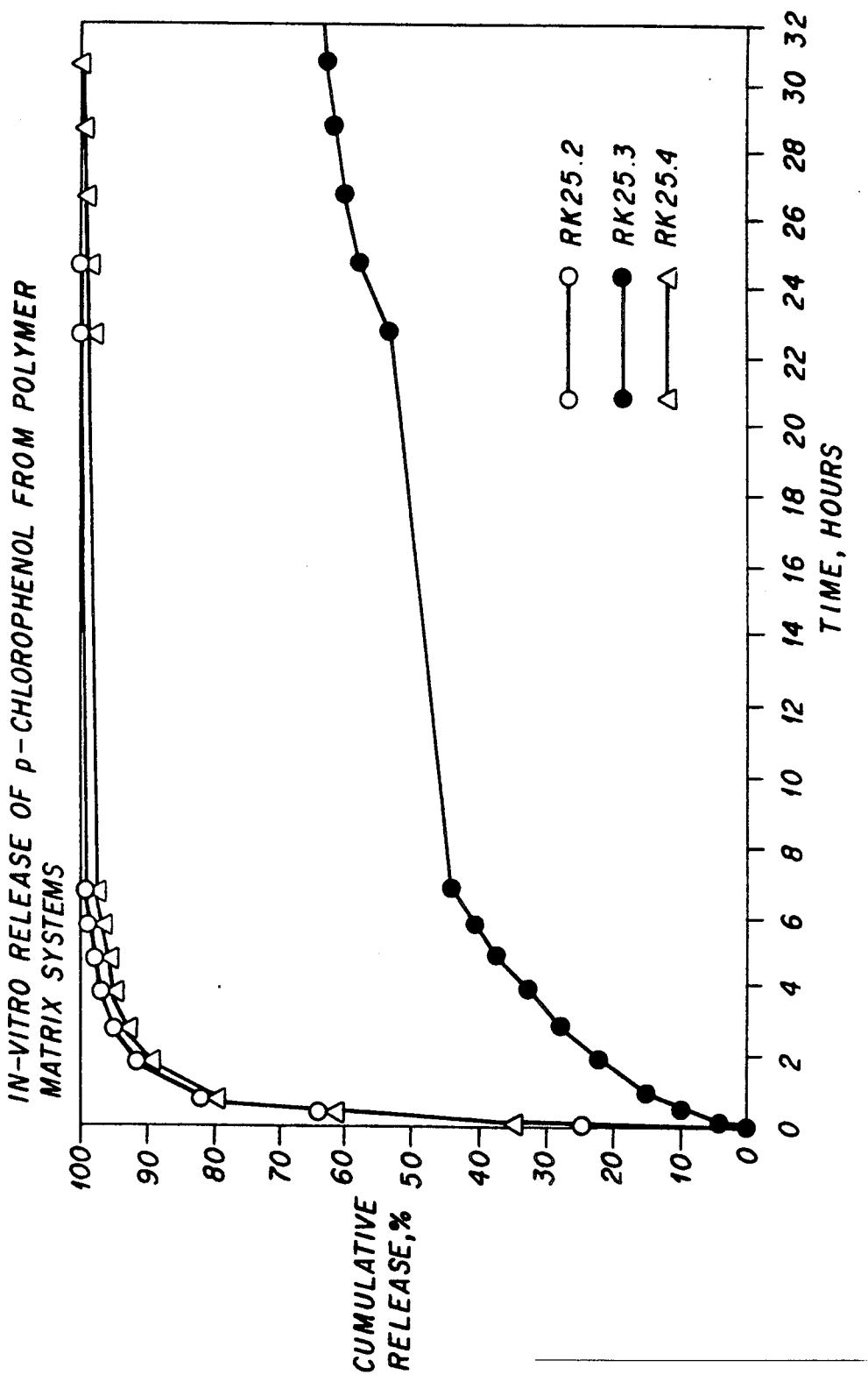
FIG. 19 shows the in vitro release of p-chlorophenol from film cast from formulations RK25.2-4.

The chlorophenol release from film cast from formulations RK25.2-4 is presented in FIG. 19. It shows that a formulation containing EUDRAGIT S (RK25.3) possesses better properties of longer release than formulations with ethyl cellulose.

Figure 20:
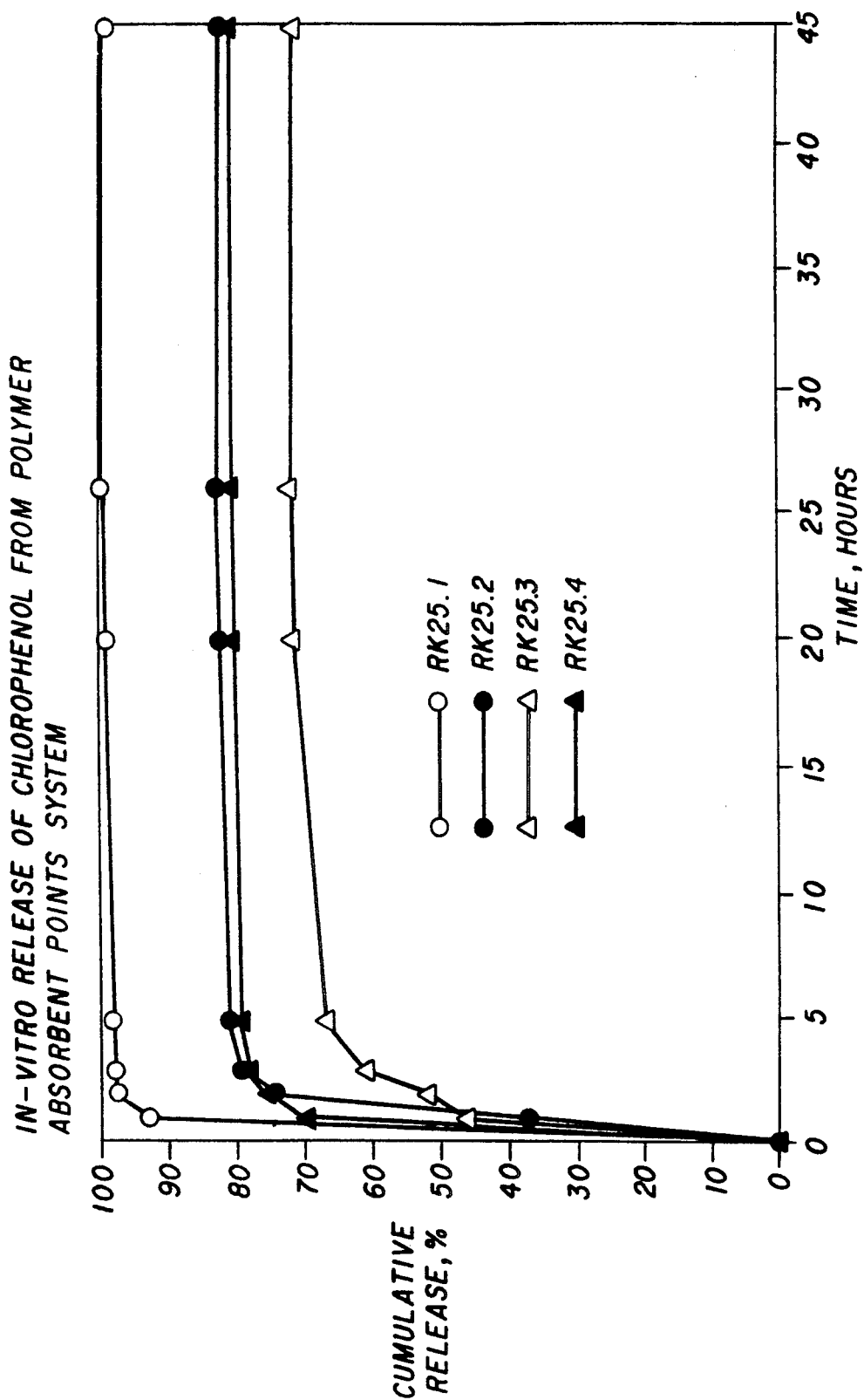
FIG. 20 shows the in vitro release of p-chlorophenol from formulations RK25.1-4 from coated absorbent points.

FIG. 20 shows the release of formulations RK25.1-4 from coated absorbent points. As is shown, formulation RK25.1 containing 11.3% PEG 400 released the chlorophenol rapidly and completely, as in the absence of polymer. Formulation RK25.3, containing less PEG 400, releases chlorophenol at a much slower rate than RK25.1, and similar to the film (FIG. 19) releases slower than RK25.2 and RK25.1 as well.

It should be noted that the recovery of the drug from ethyl cellulose-coated absorbent points was incomplete.

Formulations RK25.5 and RK25.6, which do not contain PEG 400, demonstrate very slow release profiles for CPK (FIGS. 21 and 22) although they parallel those of formulations containing PEG 400 and either ethyl cellulose or EUDRAGIT S.

Figure 21:
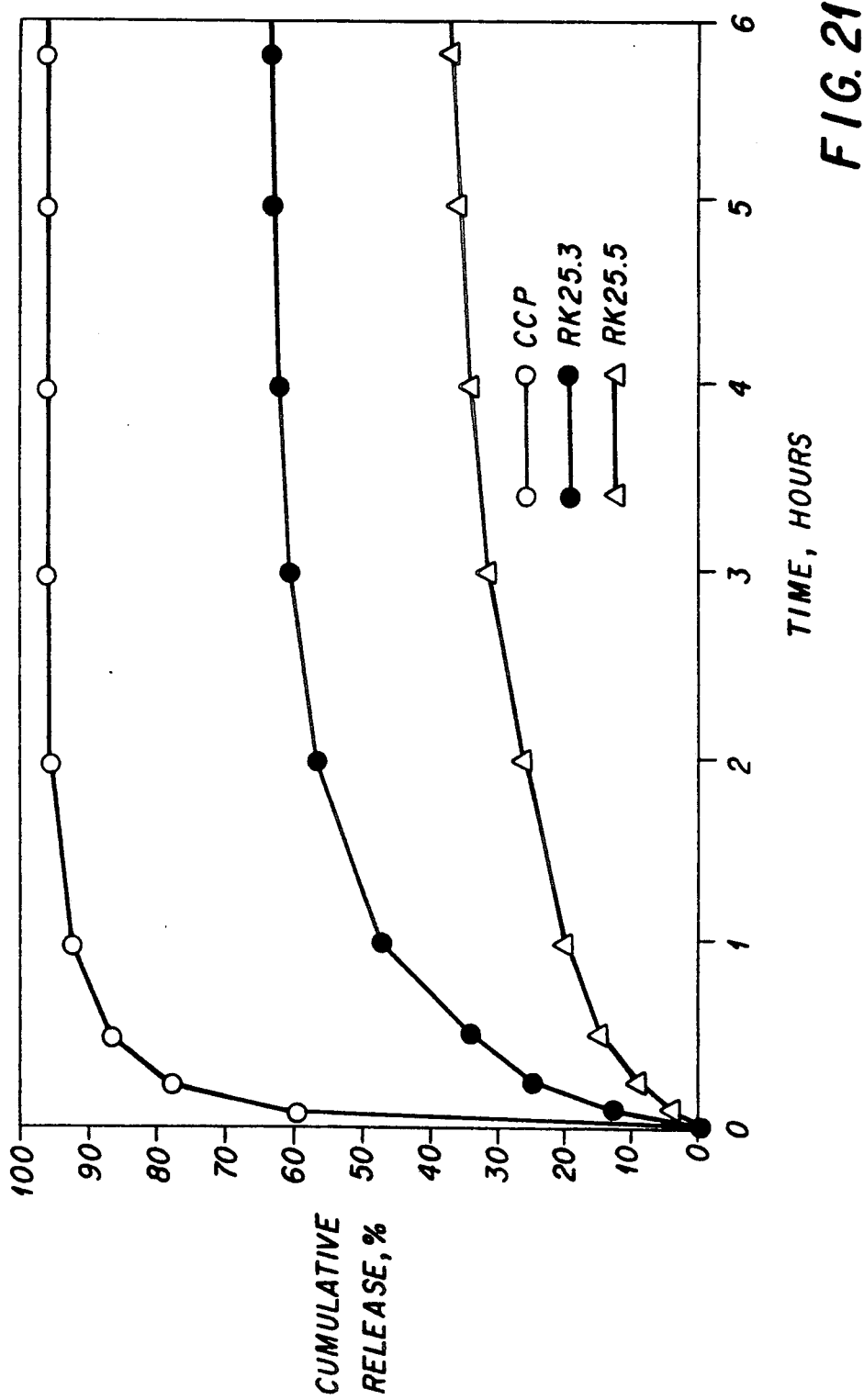
FIG. 21 shows the in vitro release of p-chlorophenol from absorbent points-polymer systems RK25.3 and RK25.5.

Chlorophenol was released from films prepared from formulations containing only camphorated parachlorophenol and polymer (RK25.5) for a period of two weeks, however only 50% of the total amount of the drug was released. Nevertheless, the in vitro release from absorbent points was much faster (FIG. 21). FIG. 21 shows that most of the drug was released within 6 hours. The effect of PEG 400 on the release profile was also demonstrated using the coated absorbent point, as also seen in FIG. 21.

TABLE XIX

| Exp. No. | Weight percent of components in formulations | | | | | |
|---|---|---|---|---|---|---|
| | RK25.1 | RK25.2 | RK25.3 | RK25.4 | RK25.5 | RK25.6 |
| CPK | 22.6 | 22.6 | 22.6 | 11.8 | 4.7 | 4.7 |
| EUDRAGIT S | 6.8 | — | 11.3 | — | 11.8 | — |
| ETHYL CELLULOSE | — | 6.8 | — | 5.9 | — | 7.1 |
| PEG 400 | 11.3 | 11.3 | 6.8 | 3.5 | — | — |
| ETHANOL | 59.3 | 59.3 | 59.3 | 78.8 | 83.5 | 85.2 |

2. The effect of $CaCl_2$, $MgCl_2$, and Tween 80 on the Release Profile of p-Chlorophenol from Matrices containing Ethyl Cellulose or EUDRAGIT S.

Figure 22:
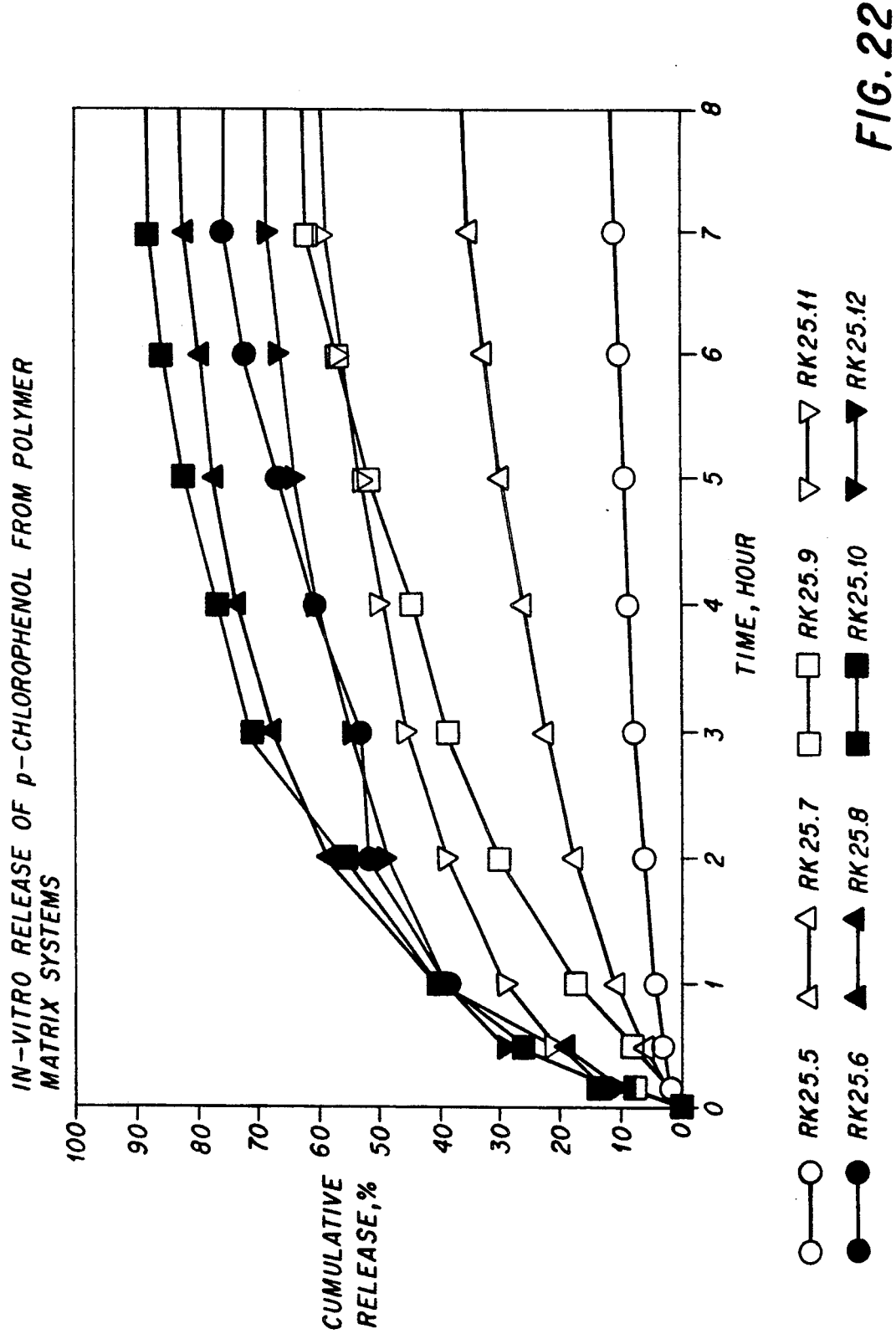
FIG. 22 shows the in vitro release of p-chlorophenol from polymer matrix systems.

The effect of the addition of $CaCl_2$, $MgCl_2$ and Tween 80 (Table XX) on the in vitro release profile is shown in FIG. 22. Addition of these components cause increase in the burst release in both EUDRAGIT S and ethyl cellulose-containing formulations (ethyl cellulose RK25.8 and 10 compared to RK25.6, EUDRAGIT S RK25.7, 9 and 11 compared to RK25.5).

Figure 23:
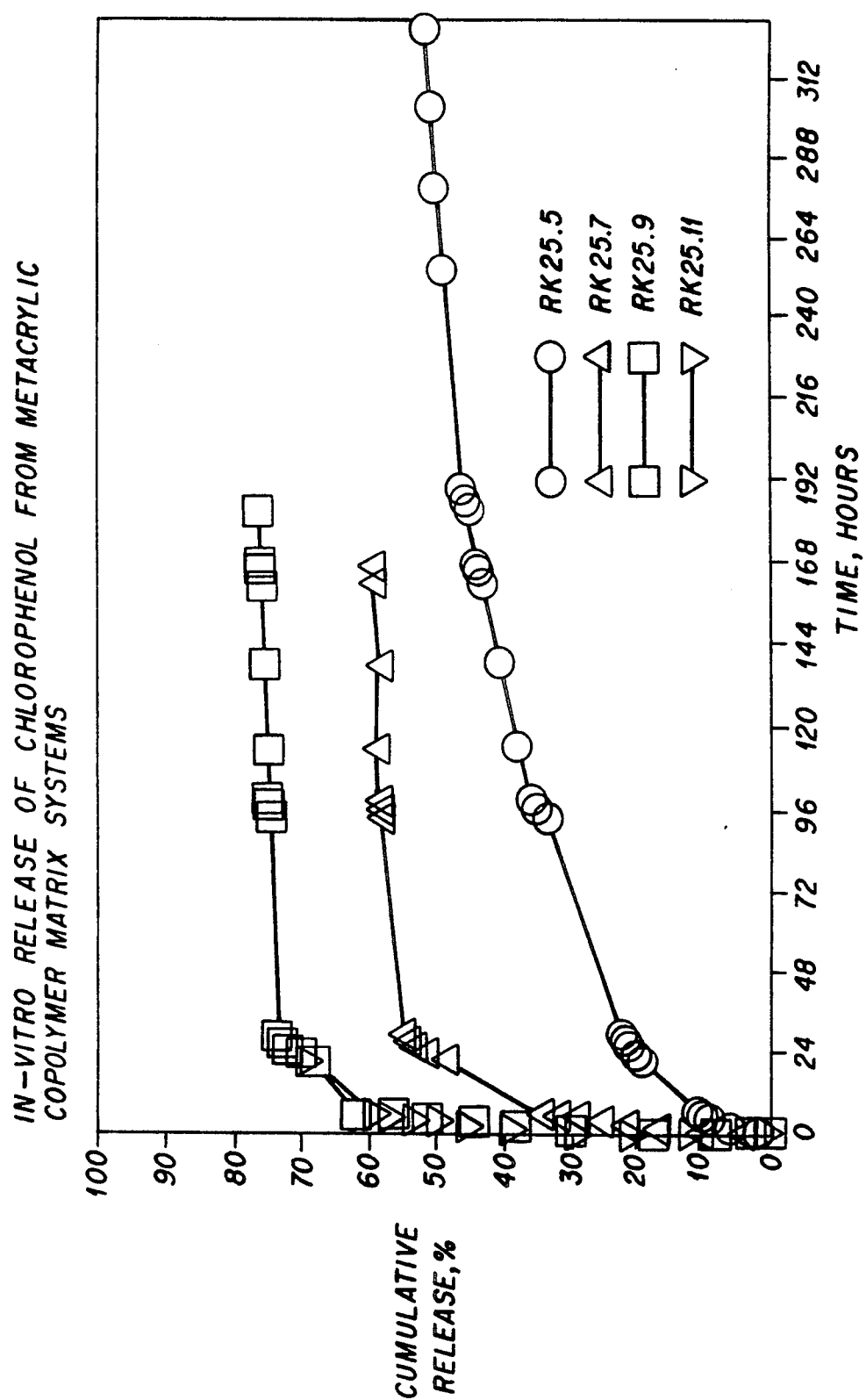
FIG. 23 shows the in vitro release of p-chlorophenol from metacrylic copolymer matrix systems.

Formulations RK25.5 (without PEG 400), RK25.7 (with $CaCl_2$), RK25.9 (with Tween 80), and RK25.11 (with $MgCl_2$) were compared over a long period of time (see FIG. 23). This comparison shows that only the formulation with no additive shows a prolonged release profile, whereas other release profiles diminished to zero after 24 hours, with incomplete recovery.

TABLE XX

| Exp. No. | Weight percent of components in formulations | | | | | |
|---|---|---|---|---|---|---|
| | RK25.7 | RK25.8 | RK25.9 | RK25.10 | RK25.11 | RK25.12 |
| CPK | 4.7 | 4.7 | 4.7 | 4.7 | 4.7 | 4.7 |
| EUDRAGIT S | 11.8 | — | 11.8 | — | 11.8 | — |
| ETHYL CELLULOSE | — | 7.1 | — | 7.1 | — | 7.1 |
| $CaCl_2$ | 2.4 | 2.4 | — | — | — | — |
| TWEEN 80 | — | — | 4.7 | 4.7 | — | — |
| $MgCl_2$ | — | — | — | — | 2.4 | 2.4 |
| ETHANOL | 81.1 | 85.8 | 78.8 | 83.54 | 81.1 | 85.8 |

Figure 24A:
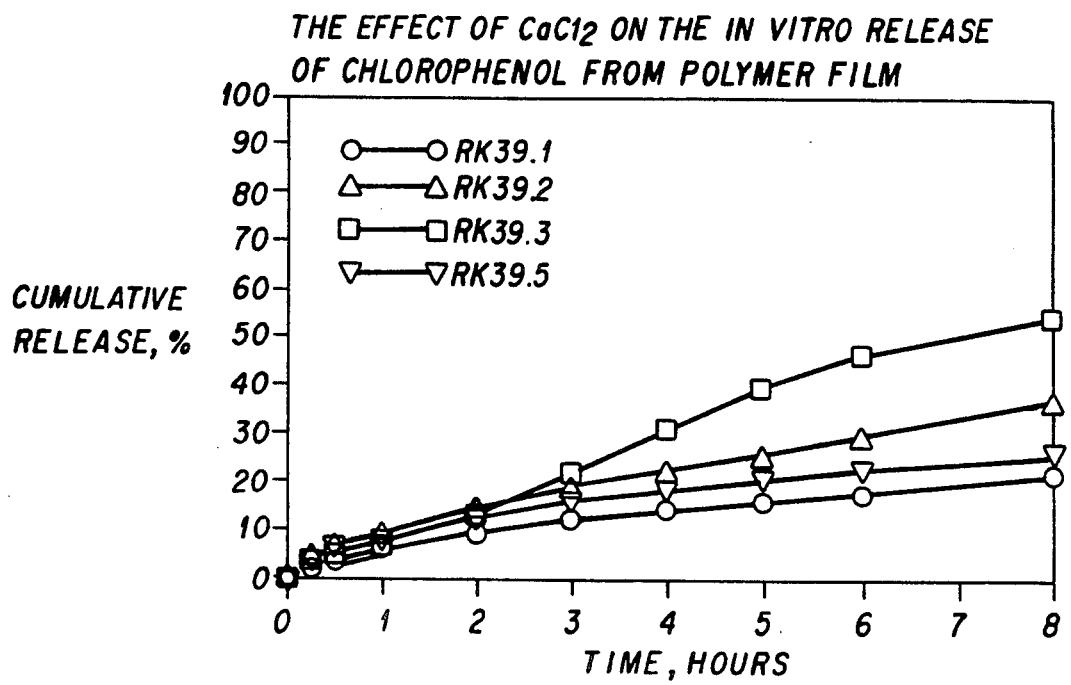
FIG. 24a shows the effect of $CaCl_2$ on the in vitro release of chlorophenol from polymer film.
Figure 24B:
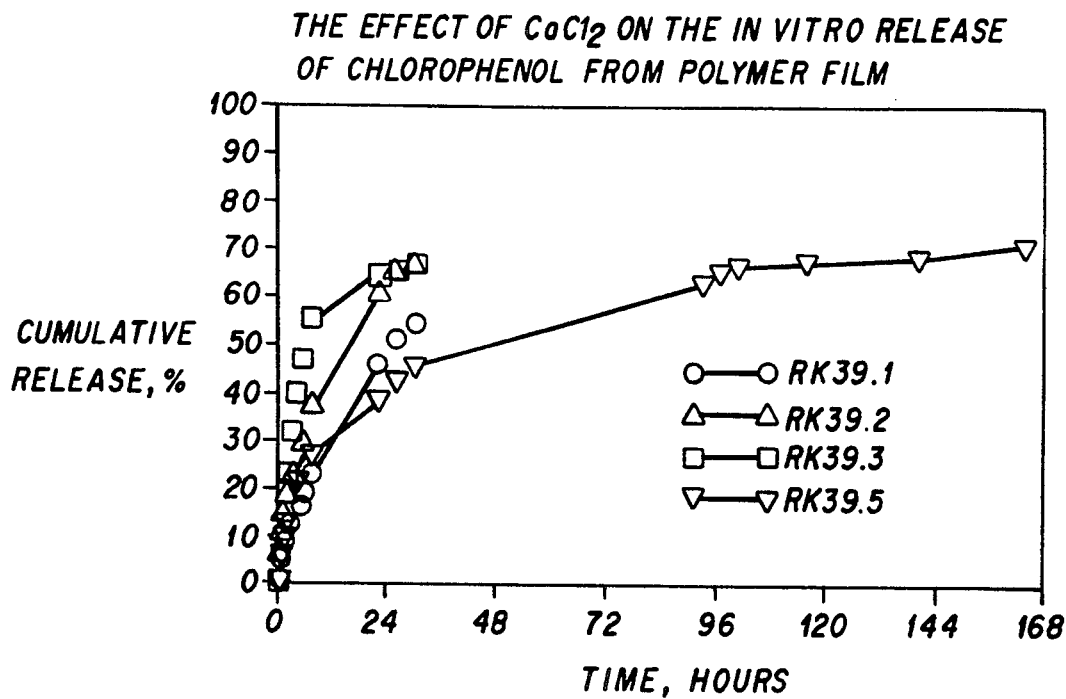
FIG. 24b shows the effect of $CaCl_2$ on the in vitro release of chlorophenol from polymer film.

By adding increasing amount of $CaCl_2$ to the formulations (Table XXI), the release patterns from the films were diminished (FIG. 24 a-b).

No significant change in the release kinetics from the paper tissue was observed (FIG. 25).

TABLE XXI

| | Weight percent of components in formulations | | | |
|---|---|---|---|---|
| Exp. No.: | RK39.1 | RK39.2 | RK39.3 | RK39.5 |
| CPK | 4.7 | 4.7 | 4.7 | 4.7 |
| EUDRAGIT S | 11.8 | 11.8 | 11.8 | 11.8 |
| $CaCl_2$ | 0.2 | 1.2 | 2.4 | — |
| ETHANOL | 83.3 | 82.3 | 81.1 | 83.54 |

Figure 26A:
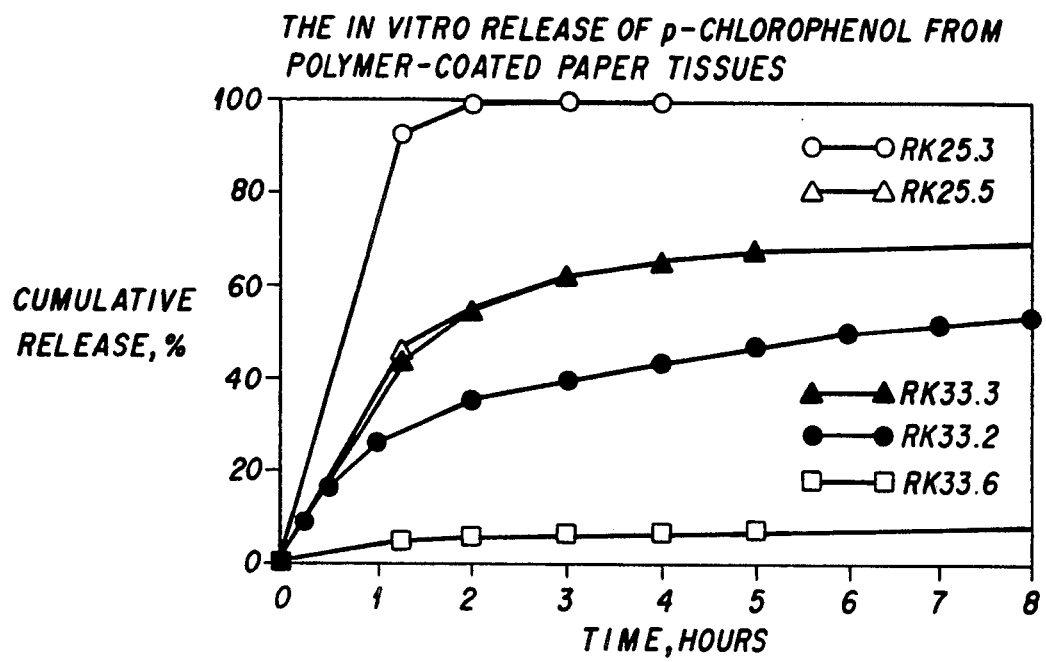
FIG. 26a shows the in vitro release of p-chlorophenol from polymer-coated paper tissues.
Figure 26B:
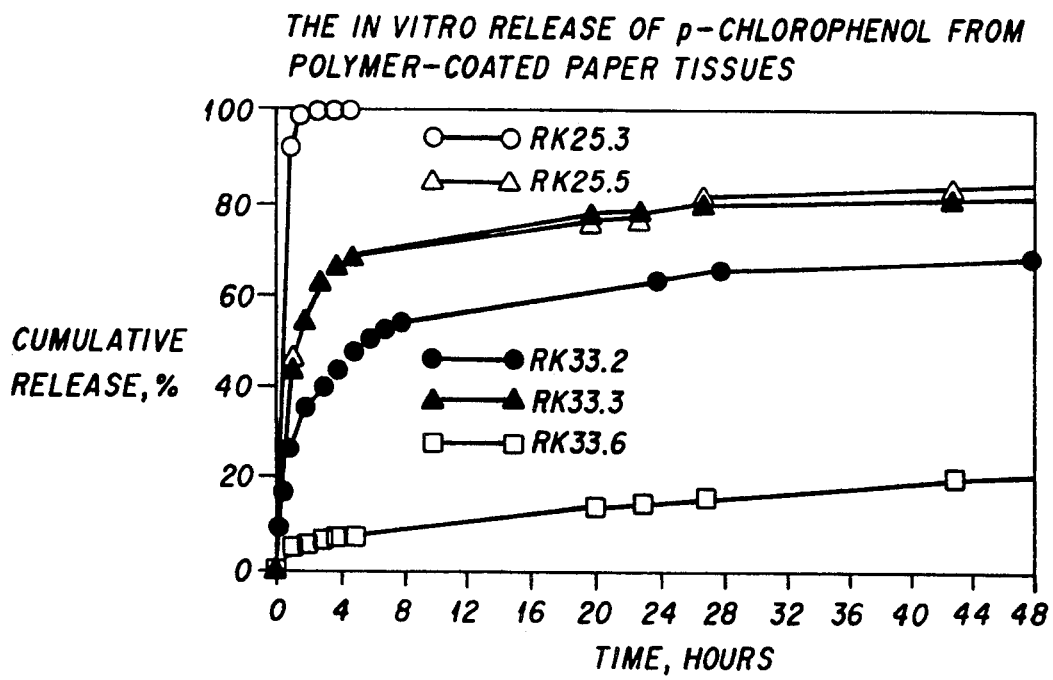
FIG. 26b shows the in vitro release of p-chlorophenol from polymer-coated paper tissues.

FIGS. 26a–b show that the release profiles from paper tissues are affected by the ratio between camphorated parachlorophenol and the polymer. As the ratio rises, the burst effect is higher, and the second phase of release begins sooner. It should be emphasized that formulations RK25.5 and RK33.3 had the same composition in the dry film (Tables XIX and XXII) and their release kinetics were practically the same, even though the ethanol content and viscosity of the formulation was different.

TABLE XXII

The effect of various concentrations of camphorated parachlorophenol and EUDRAGIT S weight percent of components in formulations

| Exp. No.: | RK33.2 | RK33.3 | RK33.6 |
|---|---|---|---|
| CPK | 22.5 | 9.2 | 4.6 |
| EUDRAGIT S | 22.5 | 23.0 | 23.0 |
| ETHANOL | 45.0 | 67.8 | 73.4 |

3. Detailed Analysis of the Release Profile and Antibacterial Effect of RK33.2

Figure 27:
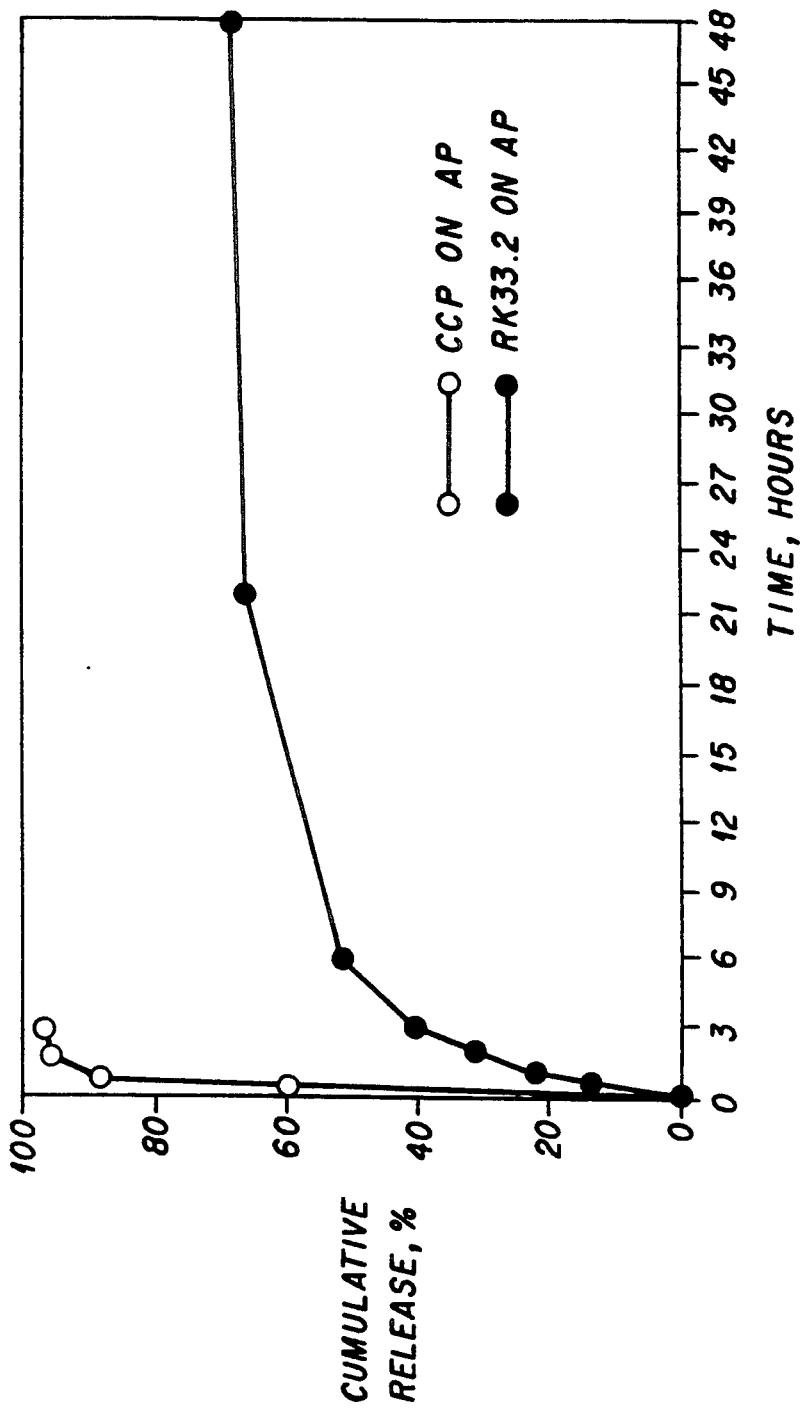
FIG. 27 shows the in vitro release of p-chlorophenol from polymer-absorbent point (AP) systems.

The release rate of CPK from absorbent points coated with formulation RK33.2 was compared to that of CPK liquid alone. The results are shown in Table XXIII and FIG. 27. It can be seen that the total amount of CPK released was almost identical in both, with a substantial difference in the length of the release time. For CPK alone the release time was about 1 hour, whereas the CPK liquid polymer lasted for up to 48 hours.

TABLE XXIII

Controlled Release of Camphorated Parachlorophenol (CPK) from Absorbent Points (AP) for Root Canal Sterilization.

| | CPK loading on AP (mg) | 1 hr release ($\mu g$/AP) | 6 hr release ($\mu g$/AP) | 22 hr release ($\mu g$/AP) | 48 hr release ($\mu g$/AP) |
|---|---|---|---|---|---|
| CPK | 3.0 | 3016.0 | 3130.0 | 3130.0 | 3130.0 |
| CPK-polymer coating system (RK33.2) | 3.8 | 922.5 | 2154.2 | 2776.5 | 3078.2 |

Figure 28A:
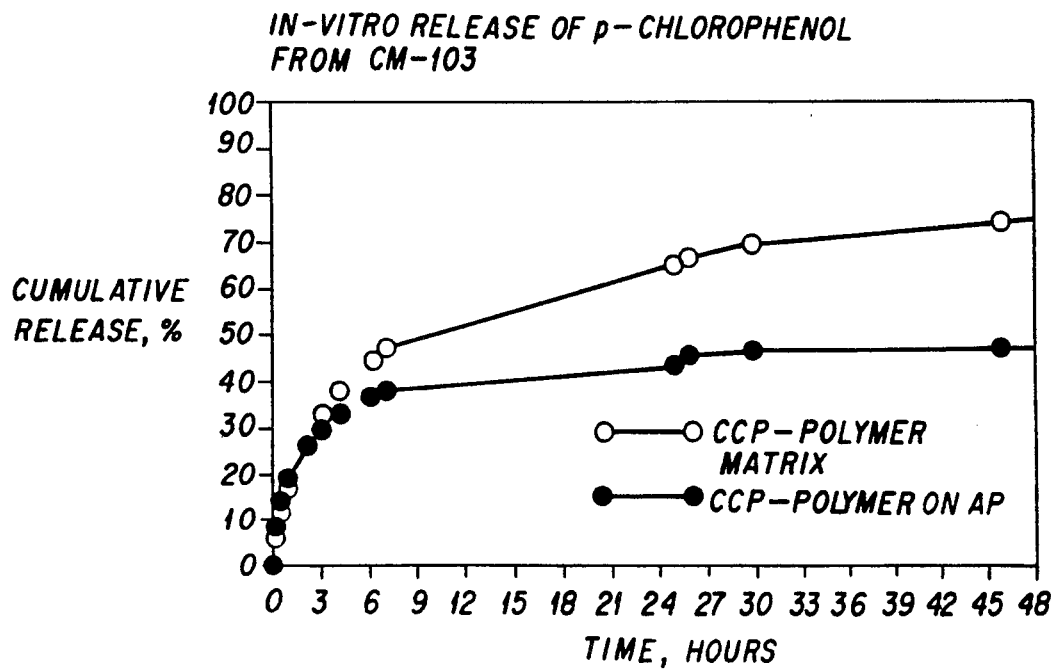
FIG. 28a shows the in vitro release of p-chlorophenol from CM-103.
Figure 28B:
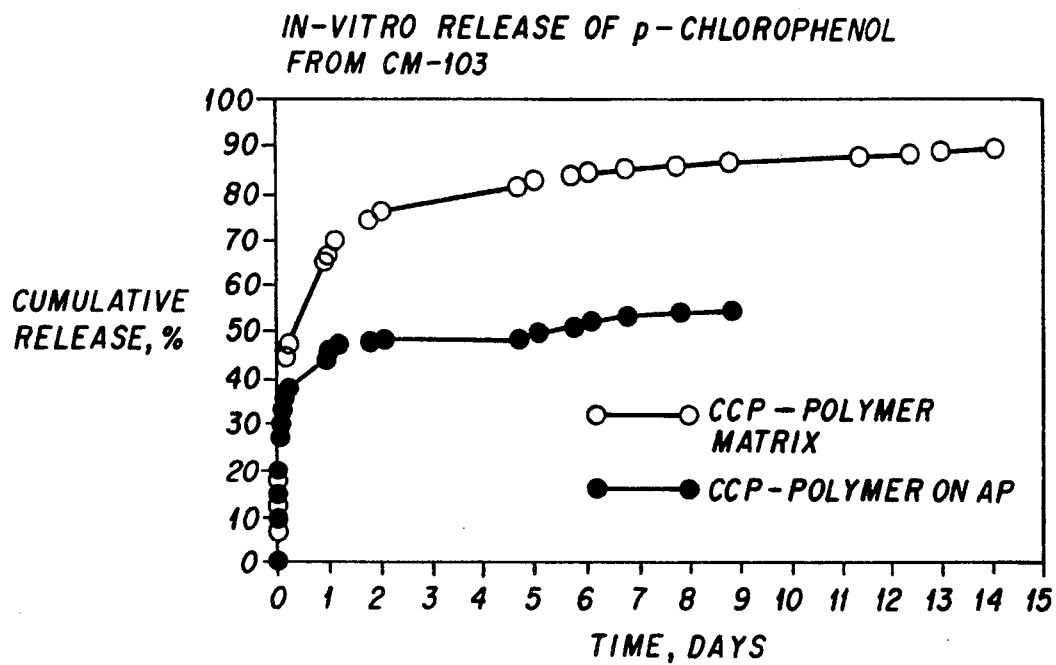
FIG. 28b shows the in vitro release of p-chlorophenol from CM-103.

Formulation RK33.2 was transferred to the pilot plant for 2.5 Kg production. The in vitro release of the product (CM-103) is presented in FIG. 28. Table XXIV demonstrates that EUDRAGIT S is practically a non-degradable polymer. EUDRAGIT S is non-soluble in a buffer solution of pH 6.8. It is concluded, therefore, that the film formed would not degrade in the root canal.

TABLE XXIV

| | Weight in mg |
|---|---|
| CPK-polymer matrix | 64 |
| Polymer matrix after 14 day release | 34 |
| CPK released in 14 days | 28.7 (89.6%) |
| Polymer lost | 1.3 |

Figure 29:
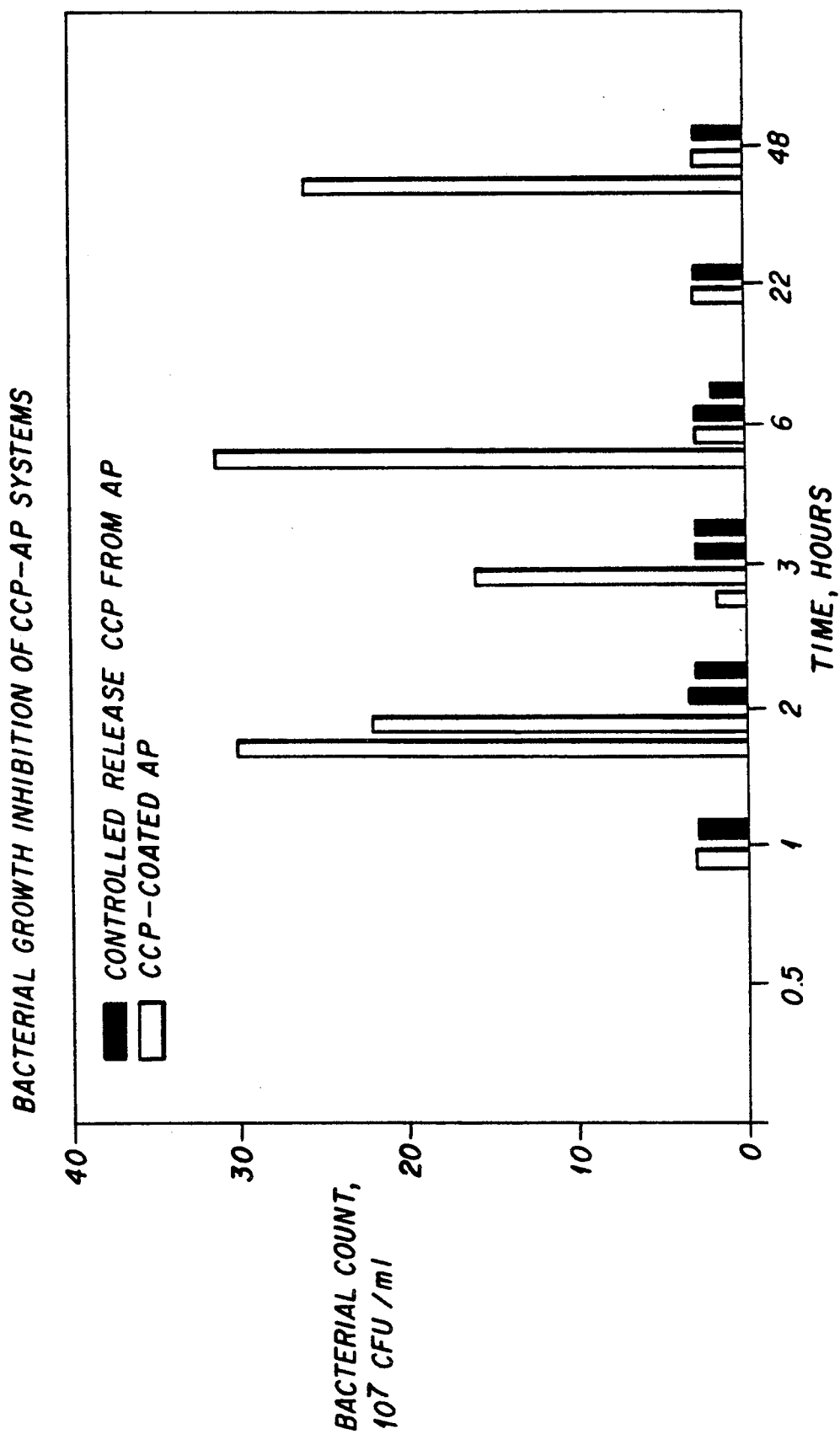
FIG. 29 shows the bacterial growth inhibition of CPK-AP (labeled as CCP-AP) systems.

The bacterial growth inhibition by the absorbent points coated with the formulation was studied. FIG. 29 shows results which were achieved from formulation RK33.2 (CPK-polymer 1:1). The release kinetics profile of CPK and RK33.2 from the absorbent points (FIG. 29) indicate that while the release from CPK-loaded absorbent points is completed within 3 hours, a sustained release for 48 hours is achieved when using formulation RK33.2.

Summary of the Root Canal Studies

Camphorated parachlorophenol was formulated with two types of polymer: ethyl cellulose and EUDRAGIT S. These two polymers were chosen because they are hydrophobic in nature and not easily degradable by body fluids. EUDRAGIT S has been definitely found to be the better polymer in terms of controlling the CPK release for longer periods of time.

The figures and data show that:

1. The release kinetics include a short burst followed by a lower rate of prolonged release. This phenomenon is an advantageous property of formulation designated for antibacterial treatments.

2. The use of film-coated absorbent points (using a formulation containing EUDRAGIT S) is better than the use of plain CPK liquid sorbed in absorbent points.

3. The release of chlorophenol from coated absorbent points is significantly faster than from film alone.

4. Additives to the formulations significantly increase the burst effect and almost eliminate the sustained-release patterns. $MgCl_2$ and Tween 80 also increase the total amount of drug released. The additives are soluble in the buffer solution, probably causing the formation of pores in the film that facilitate release.

5. Film or coated absorbent points containing the plasticizer PEG 400 enhance the release rate to a very large extent. It seems that CPK is a plasticizer by itself and the addition of PEG 400 is unnecessary.

6. The ratio between the active material and the polymer changed the release kinetics. Formulations containing high concentrations of CPK release larger portions of the active material. However the kinetics are much faster, the short burst is large, and the release is finished sooner. The formulations containing 1:1 polymer to CPK have been found to have the optimal ratio both by in vitro release kinetics and by the microbiology study.

Therefore, in summary, the best formulation for absorbent points was found to be RK33.2, which showed an antibacterial effect for at least 48 hours in the in vitro studies. The amount of coated polymer that was lost in the in vitro studies did not exceed 3%, demonstrating the non-degradable feature of the coated absorbent point. The burst effect demonstrated in this particular formulation was sufficient to eliminate the majority of bacteria in the root canal. The prolonged CPK release assured a low degree of bacteria, and that no reinfection of the root canal could take place.

EXAMPLE 21

Use of RAA to Alter the Release Rates of Active Agents

In the following Table XXV, unless otherwise noted, amounts are in grams:

TABLE XXV

| Exp. No.: | C-176 | C-184 | C-187 |
|---|---|---|---|
| Tween 80 | 0.5 | 0.5 | 0.5 |
| Sorbitol | 4.5 | 2.5 | — |
| EUDRAGIT L | 4.4 | 4.4 | 4.4 |
| CHDG 20% | 3 ml | 3 ml | 3 ml |
| L-Arginine | — | 2.0 | 2.0 |
| Alcohol 95% | 21 ml | 21 ml | 21 ml |
| Sodium polyphosphate | — | — | 2.5 |
| Water, purified | 9 ml | 9 ml | 9 ml |

Figure 30:
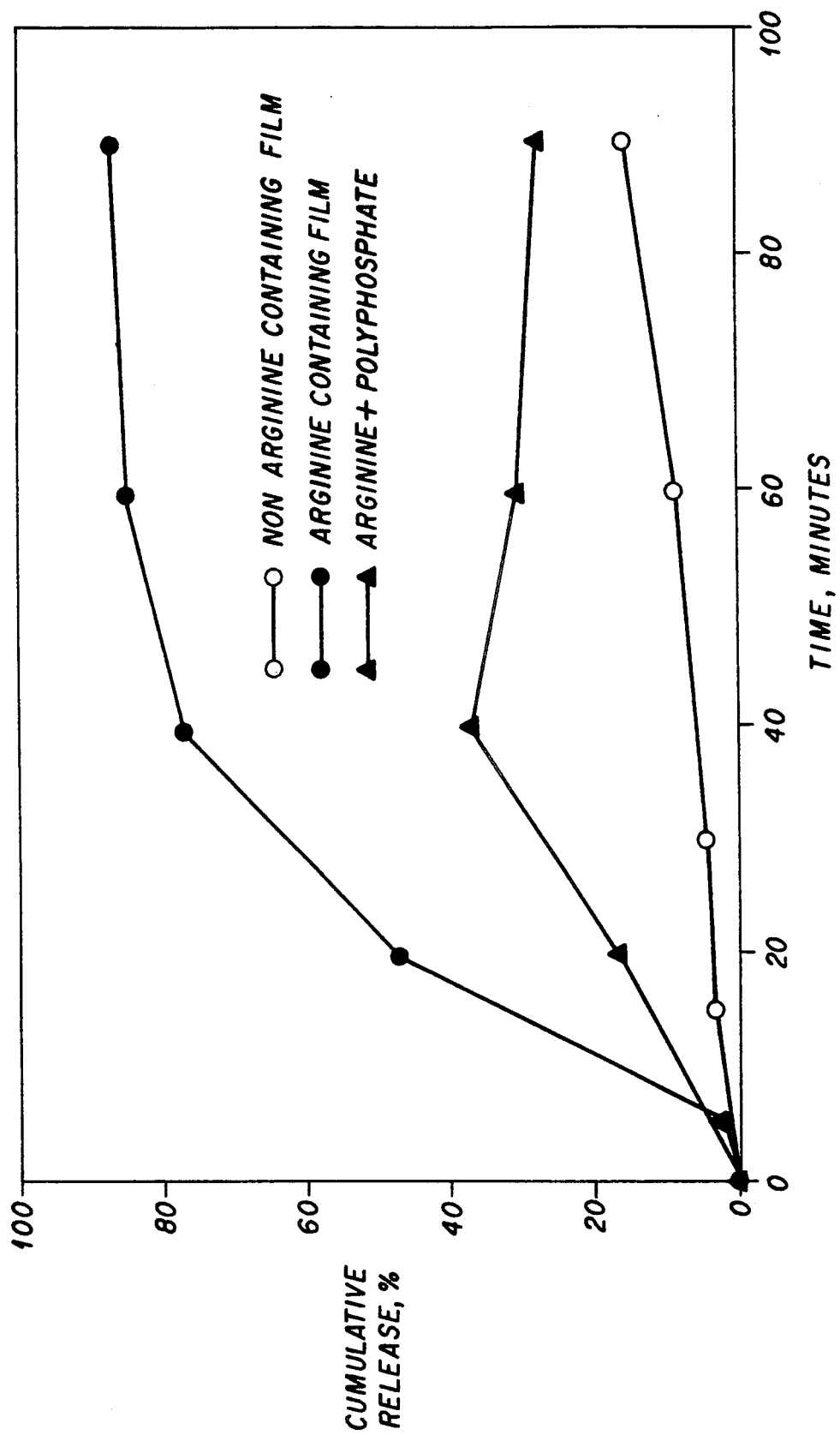
FIG. 30 shows the cumulative release of cetylpyridinium chloride (CPC) from liquid polymer films as a function of the presence of arginine.

As shown in FIG. 30, when no arginine was added to the preparation, the release occured very slowly with a maximum recovery of 20–30% even though the film eventually degraded. As arginine was incorporated, the release was dramatically increased with almost complete recovery. Moreover, the film was more hydrophilic than usual and its degradation was fitted more to the term dissolution than to the other examples. However, the rate of release can be further adjusted by using agents such as sodium polyphosphate at different concentrations.

Having now fully described the invention, it will be understood by those with skill in the art that the scope may be performed with a wide and equivalent range of conditions, parameters, and the like, without affecting the spirit or scope of the invention or any embodiment thereof.

What is claimed is:

1. A sustained-released liquid polymer composition which consists essentially of:
   (a) one or more sustained release acrylic polymers;
   (b) a pharmacological agent;
   (c) a release adjusting agent selected from the group consisting of a cross-linking agent, a polysaccharide, a lipid, a protein, a sodium citrate, sodium docusate, an amino acid and sodium polyphosphate; and
   (d) a pharmaceutically acceptable vehicle selected from the group consisting of water; ethyl alcohol; and ethyl alcohol and water, wherein said sustained release acrylic polymers are selected from the group consisting of:
   (1) a methacrylic acid type A copolymer, an anionic copolymer based on methacrylic acid and methylmethacrylate wherein the ratio of free carboxyl groups to the ester groups is approximately 1:1;
   (2) a methacrylic acid type B compolymer, an anionic copolymer based on methacrylic acid and methylmethacrylate wherein the ratio of free carboxyl groups to the ester groups is approximately 1:2,
   (3) a dimethylaminoethylacrylate/ethylmethacrylate copolymer, a copolymer based on acrylic and methacrylic acid esters with a low content of quaternary ammonium groups wherein the molar ratio of the ammonium groups to the remaining neutral (meth)acrylic acid esters is 1:20; and
   (4) an ethyl methacrylate/chlorotrimethylammoniumethyl methacrylate copolymer, a copolymer based on acrylic and methacrylic acid esters with a low content of quaternary ammonium groups wherein the molar ratio of the ammonium groups to the remaining neutral (meth)acrylic acid esters is 1:40.

2. The liquid polymer composition of claim 1, wherein said amino acid is selected from the group consisting of: arginine, lysine, aspartic acid, and glutaric acid.

3. The liquid polymer composition of claim 1, wherein said pharmacological agent is selected from the group consisting of: an antibiotic, an antiseptic, an anti-fungal agent, an anti-viral agent, and a hypersensitivity agent.

4. The liquid polymer composition of claim 1, wherein said pharmacological agent is a bacteriocidal quaternary ammonium salt.

5. The liquid polymer composition of claim 4 wherein said bacteriocidal quaternary ammonium salt is selected from the group consisting of cetylpyridinium chloride and benzalkonium chloride.

6. The liquid polymer composition of claim 5, wherein said bacteriocidal quaternary ammonium salt is cetylpyridinium chloride.

7. The liquid polymer composition of claim 5, wherein said bacteriocidal quaternary ammonium salt is benzalkonium chloride.

8. The liquid polymer composition of claim 3, wherein said pharmacological agent is a hypersensitivity agent.

9. The liquid polymer composition of claim 8, wherein said hypersensitivity agent is selected from the group consisting of a strontium salt, a potassium salt, a fluoride and an oxylate.

10. The liquid polymer composition of claim 9, wherein said strontium salt is selected from the group consisting of strontium chloride and strontium citrate.

11. The liquid polymer composition of claim 9, wherein said potassium salt is selected from the group consisting of potassium chloride, potassium hydrogen tartrate and potassium nitrate.

12. The liquid polymer composition of claim 9, wherein said fluoride is stannous fluoride.

13. The liquid polymer composition of claim 9, wherein said oxylate is potassium hydrogen oxylate.

14. A sustained-released liquid polymer composition which consists essentially of:
   (a) one or more sustained release acrylic polymers;
   (b) a pharmacological agent;
   (c) a release adjusting agent selected from the group consisting of a cross-linking agent, a polysaccharide, a lipid, a protein, a sodium citrate, sodium docusate, an amino acid and sodium polyphosphate;
   (d) a pharmaceutically acceptable vehicle selected from the group consisting of water; ethyl alcohol; and ethyl alcohol and water; and
   (e) a plasticizer;

wherein said sustained release acrylic polymers are selected from the group consisting of:
   (1) a methacrylic acid type A copolymer, an anionic copolymer based on methacrylic acid and methylmethacrylate wherein the ratio of free carboxyl groups to the ester groups is approximately 1:1;
   (2) a methacrylic acid type B copolymer, an anionic copolymer based on methacrylic acid and methylmethacrylate wherein the ratio of free carboxyl groups to the ester groups is approximately 1:2;
   (3) a dimethylaminoethylacrylate/ethylmethacrylatecopolymer, a copolymer based on acrylic and methacrylic acid esters with a low content of quaternary ammonium groups wherein the molar ratio of the ammonium groups to the remaining neutral (meth)acrylic acid esters is 1:20; and (4) an ethyl methacrylate/chlorotrimethylammoniumethyl methacrylate copolymer, a copolymer based on acrylic and methacrylic acid esters with a low content of quaternary ammonium groups wherein the molar ratio of the ammonium groups to the remaining neutral (meth)acrylic acid esters is 1:40.

15. The liquid polymer composition of claim 14, wherein said plasticizer is selected from the group consisting of: polyethylene glycol and dibutyl phthalate.

16. The liquid polymer composition of claim 1, wherein said cross-linking agent is selected from the group consisting of glutaraldehyde, citric acid, lysine, aspartic acid, and glutaric acid.

17. The liquid polymer composition of claim 1, wherein said polysaccharide is dextran.

18. The liquid polymer composition of claim 1, wherein said lipid is sodium docusate.

* * * * *